(12) United States Patent
Bird et al.

(10) Patent No.: US 8,501,262 B2
(45) Date of Patent: Aug. 6, 2013

(54) METHOD AND MEANS FOR IMPROVING BOWEL HEALTH

(75) Inventors: Anthony Richard Bird, North Brighton (AU); Gulay Saygat Mann, Page (AU); Sadequr Rahman, Nicholls (AU); Ahmed Regina, Palmerston (AU); Zhongyi Li, Kaleen (AU); David Lloyd Topping, Victor Harbor (AU); Matthew Kennedy Morell, Aranda (AU)

(73) Assignee: Commonwealth Scientific and Industrial Research Organisation, Campbell (AU)

(*) Notice: Subject to any disclaimer, the term of this patent is extended or adjusted under 35 U.S.C. 154(b) by 241 days.

(21) Appl. No.: 12/799,013

(22) Filed: Apr. 16, 2010

(65) Prior Publication Data

US 2011/0212916 A1    Sep. 1, 2011

Related U.S. Application Data

(62) Division of application No. 11/324,063, filed on Dec. 30, 2005, now Pat. No. 7,700,139.

(60) Provisional application No. 60/688,944, filed on Jun. 8, 2005.

(30) Foreign Application Priority Data

Dec. 30, 2004    (AU) ................ 2004907350

(51) Int. Cl.
*A21D 13/00*    (2006.01)

(52) U.S. Cl.
USPC ........ 426/549; 800/320.3; 424/750; 435/419; 435/410

(58) Field of Classification Search
USPC .................................... 426/549, 658
See application file for complete search history.

(56) References Cited

U.S. PATENT DOCUMENTS

| | | | |
|---|---|---|---|
| 3,690,896 | A | 9/1972 | Maxwell et al. |
| 4,770,710 | A | 9/1988 | Friedman et al. |
| 5,051,271 | A | 9/1991 | Iyengar et al. |
| 6,013,861 | A | 1/2000 | Bird et al. |

(Continued)

FOREIGN PATENT DOCUMENTS

| | | |
|---|---|---|
| GB | 2 360 521 | 9/2001 |
| WO | WO 94/14342 | 7/1994 |

(Continued)

OTHER PUBLICATIONS

U.S. Appl. No. 13/243,747, filed Sep. 23, 2011, Regina et al.

(Continued)

*Primary Examiner* — Elizabeth Gwartney
(74) *Attorney, Agent, or Firm* — John P. White; Gary J. Gershik; Cooper & Dunham LLP

(57) ABSTRACT

A method and composition for improving one or more indicators of bowel health or metabolic health in a mammalian animal. This comprises the delivering to the gastrointestinal tract of the animal an effective amount of an altered wheat starch in the form of or derived from the grain of a wheat plant. The proportion of amylose in the starch of the grain is at least 30% and/or the grain comprises a reduced level of SBEIIa enzyme activity and/or protein relative to wild-type grain.

15 Claims, 12 Drawing Sheets

(56) References Cited

U.S. PATENT DOCUMENTS

| | | | |
|---|---|---|---|
| 6,303,174 B1 | 10/2001 | McNaught et al. | |
| 6,307,125 B1 | 10/2001 | Block et al. | |
| 6,376,749 B1 | 4/2002 | Broglie et al. | |
| 6,483,009 B1 | 11/2002 | Poulsen et al. | |
| 6,730,825 B1 | 5/2004 | Goldsbrough et al. | |
| 6,734,339 B2 | 5/2004 | Block et al. | |
| 6,897,354 B1 * | 5/2005 | Yamamori | 800/266 |
| 6,903,255 B2 | 6/2005 | Yamamori et al. | |
| 6,916,976 B1 | 7/2005 | Li et al. | |
| 7,001,771 B1 | 2/2006 | Morell et al. | |
| 7,009,092 B1 | 3/2006 | Jane et al. | |
| 7,041,484 B1 | 5/2006 | Baga et al. | |
| 7,365,189 B2 | 4/2008 | Block et al. | |
| 7,521,593 B2 | 4/2009 | Regina et al. | |
| 7,667,114 B2 | 2/2010 | Morell et al. | |
| 7,700,139 B2 | 4/2010 | Bird et al. | |
| 7,700,826 B2 | 4/2010 | Morell et al. | |
| 7,790,955 B2 | 9/2010 | Li et al. | |
| 7,812,221 B2 | 10/2010 | Regina et al. | |
| 7,888,499 B2 | 2/2011 | Morell et al. | |
| 7,919,132 B2 | 4/2011 | Regina et al. | |
| 7,993,686 B2 | 8/2011 | Bird et al. | |
| 8,115,087 B2 | 2/2012 | Regina et al. | |
| 8,178,759 B2 | 5/2012 | Morell et al. | |
| 8,188,336 B2 | 5/2012 | Li et al. | |
| 2003/0035857 A1 * | 2/2003 | Sroka | 426/19 |
| 2004/0060083 A1 | 3/2004 | Regina et al. | |
| 2004/0199942 A1 | 10/2004 | Morell et al. | |
| 2004/0204579 A1 | 10/2004 | Block et al. | |
| 2005/0071896 A1 | 3/2005 | Regina et al. | |
| 2006/0010517 A1 | 1/2006 | Li et al. | |
| 2006/0035379 A1 | 2/2006 | Morell et al. | |
| 2006/0204597 A1 | 9/2006 | Bird et al. | |
| 2006/0286186 A1 | 12/2006 | Bird et al. | |
| 2007/0300319 A1 | 12/2007 | Li et al. | |
| 2009/0226592 A1 | 9/2009 | Regina et al. | |
| 2010/0330253 A1 | 12/2010 | Morell et al. | |
| 2011/0010807 A1 | 1/2011 | Morell et al. | |
| 2011/0059225 A1 | 3/2011 | Li et al. | |
| 2011/0070352 A1 | 3/2011 | Regina et al. | |
| 2012/0074247 A1 | 3/2012 | Regina et al. | |
| 2012/0266267 A1 | 10/2012 | Li et al. | |

FOREIGN PATENT DOCUMENTS

| | | |
|---|---|---|
| WO | WO 97/22703 | 6/1997 |
| WO | WO 97/34591 | 9/1997 |
| WO | WO 00/15810 | 3/2000 |
| WO | WO 00/66745 | 9/2000 |
| WO | WO 01/32886 | 5/2001 |
| WO | WO 01/62934 | 8/2001 |
| WO | WO 02/37955 | 5/2002 |
| WO | WO 02/101059 | 12/2002 |
| WO | WO 03/023024 | 3/2003 |
| WO | WO 03/094600 A1 | 11/2003 |
| WO | WO 2005/001098 | 1/2005 |
| WO | WO 2005/040381 | 6/2005 |

OTHER PUBLICATIONS

File History of U.S. Patent No. 7,812,221, Regina et al., issued Oct. 12, 2010 (U.S. Appl. No. 10/881,808, filed Jun. 20, 2004).
File History of U.S. Patent Application Publication No. 2011-0070352, Regina et al., published Mar. 24, 2011 (U.S. Appl. No. 12/881,040, filed Sep. 13, 2010).
File History of U.S. Patent Application Publication No. 2006-028686, Bird et al., published Dec. 21, 2006 (U.S. Appl. No. 11/417,330, filed May 2, 2006).
File History of U.S. Patent No. 7,790,955, Li et al., issued Sep. 7, 2010 (U.S. Appl. No. 10/577,564, filed Apr. 27, 2006).
File History of U.S. Patent Application Publication No. 2011-0059225, Li et al., published Mar. 10, 2011 (U.S. Appl. No. 12/806,167, filed Aug. 6, 2010).
File History of U.S. Patent No. 7,888,499, Morell et al., issued. Feb. 15, 2011 (U.S. Appl. No. 10/416,439, filed Dec. 5, 2003).
File History of U.S. Patent No. 7,001,771, Morell et al., issued Feb. 21, 2006 (U.S. Appl. No. 10/018,418, filed May 9, 2002).
File History of U.S. Patent No. 7,700,826, Morell et al., issued Apr. 20, 2010 (U.S. Appl. No. 11/231,599, filed Sep. 21, 2005).
File History of U.S. Patent No. 7,521,593, Regina et al., issued Apr. 21, 2009 (U.S. Appl. No. 10/434,893, filed May 9, 2003.
File History of U.S. Patent No. 7,919,132, Regina et al., issued Apr. 5, 2011 (U.S. Appl. No. 12/384,823, filed Apr. 9, 2009).
File History of U.S. Patent No. 7,667,114, Morell et al., issued Feb. 23, 2010 (U.S. Appl. No. 10/204,347, filed Feb. 20, 2002).
File History of U.S. Patent Application Publication No. 2011-0010807, Morell et al., published Jan. 13, 2011 (U.S. Appl. No. 12/707,437, filed Feb. 17, 2010).
Amendment, submitted Jan. 30, 2008 in connection with U.S. Appl. No. 11/324,063.
Amendment, submitted Jul. 16, 2008 in connection with U.S. Appl. No. 11/324,063.
Amendment, submitted Mar. 2, 2009 in connection with U.S. Appl. No. 11/324,063.
Amendment, submitted May 18, 2006 in connection with U.S. Appl. No. 11/324,063.
Office Action, issued May 30, 2008 in connection with U.S. Appl. No. 11/324,063.
Office Action, issued Oct. 16, 2007 in connection with U.S. Appl. No. 11/324,063.
Office Action, issued Oct. 29, 2008 in connection with U.S. Appl. No. 11/324,063.
Response to Restriction Requirement, submitted Aug. 1, 2007 in connection with U.S. Appl. No. 11/324,063.
Restriction Requirement, issued Jul. 13, 2007 in connection with U.S. Appl. No. 11/324,063.
Terminal Disclaimer Approval, issued Aug. 21, 2008 in connection with U.S. Appl. No. 11/324,063.
Amendment, submitted Nov. 22, 2010 in connection with U.S. Appl. No. 11/417,330.
Office Action, issued Jul. 21, 2010 in connection with U.S. Appl. No. 11/417,330.
Amendment, submitted Jan. 22, 2010 in connection with U.S. Appl. No. 11/417,330.
Terminal Disclaimer approval issued Aug. 28, 2009 in connection with U.S. Appl. No. 11/417,330.
Office Action, issued Jul. 22, 2009 in connection with U.S. Appl. No. 11/417,330.
Amendment, submitted Mar. 17, 2009 in connection with U.S. Appl. No. 11/417,330.
Office Action, issued Nov. 17, 2008 in connection with U.S. Appl. No. 11/417,330.
Communication, submitted Nov. 14, 2008 in connection with U.S. Appl. No. 11/417,330.
Response to Office Action, submitted Jul. 16, 2008 in connection with U.S. Appl. No. 11/417,330.
Office Action, issued May 14, 2008 in connection with U.S. Appl. No. 11/417,330.
Amendment, submitted Jan. 30, 2008 in connection with U.S. Appl. No. 11/417,330.
Office Action, issued Oct. 3, 2007 in connection with U.S. Appl. No. 11/417,330.
Response to Restriction Requirement, submitted Sep. 7, 2007 in connection with U.S. Appl. No. 11/417,330.
Restriction Requirement, issued Aug. 7, 2007 in connection with U.S. Appl. No. 11/417,330.
Notice of Allowance, issued Mar. 24, 2011 in connection with U.S. Appl. No. 11/417,330.
U.S. Appl. No. 13/289,884, filed Nov. 4, 2011, Regina et al.
Communication Regarding Observations by Third Parties, issued Mar. 8, 2011 by the European Patent Office in connection with corresponding European Patent Application No. 05821526.0.
Third Party Observations, filed Feb. 21, 2011 in connection with corresponding European Patent Application No. 05821526.0.
Supplemental European Search Report, issued Mar. 12, 2012 by the European Patent Office in connection with corresponding European Patent Application No. 05821526.0.

Wasserman et al. (2004) "Microstructure, Thermal properties and susceptibility of the high amylose wheat starch to enzymatic hydrolysis: A new material for resistant starch (SRIII) production," Polish Journal of Food and Nutrition Sciences vol. 13-54, No. 2, pp. 151-156.

First Examination Report, dated Dec. 22, 2011 issued by the Japan Patent Office in connection with corresponding Japanese Patent Application No. 2007-548646.

Japanese Patent Laid Open No. H10-279487, (1998).

Japanese Patent Laid Open No. H10-195105, (1998).

Ayano et al., (1978) "Energy Assessment for Breads Containing Amylomaize V Starch," Nutrition and Food vol. 31, No. 5, pp. 449-457.

Jun. 8, 2012 Office Action, issued in connection with corresponding Canadian Patent Application No. 2,594,155.

Jun. 22, 2012 Response filed in connection with corresponding Japanese Patent Application No. 2007-548646.

Dec. 22, 2011 Examination Report, issued in connection with corresponding Japanese Patent Application No. 2007-548646 (English Language Translation).

Jan. 18, 2012 Notice of Acceptance, issued in connection with corresponding Australian Patent Application No. 2005321754.

Mar. 12, 2012 European Search Report, issued in connection with corresponding European Patent Application No. 05821526.0.

U.S. Appl. No. 13/462,629, filed May 2, 2012, Li et al.

U.S. Appl. No. 13/466,772, filed May 8, 2012, Morell et al.

Slade et al., "Development of High Amylose Wheat Through Tilling," BMC Plant Biology, 12:69-100, May 14, 2012.

Liu et al. (2003) "Stable Inheritance of the Antisense Waxy Gene in Transgenic Rice with Reduced Amylose Level and Improved Quality," Transgenic Research, 12:71-82.

Wei et al. (2010) "C-Type Starch from High-Amylose Rice Resistant Starch Granules Modified by Antisense RNA Inhibition of Starch Branching Enzyme," Journal of Agricultural and Food Chemistry, 58: 7383-7388.

File History of U.S. Patent Application Publication No. 2010-0330253, Morell et al., published Dec. 20, 2010 (U.S. Appl. No. 12/800,143, filed May 10, 2010).

File History of U.S. Patent Application Publication No. 2012-0074247, Regina et al., published Mar. 29, 2012 (U.S. Appl. No. 13/243,220).

File History of U.S. Patent Application Publication No. 2012-0114770, Regina at el., published May 10, 2012.

File History of U.S. Patent Application Publication No. 2012-0266267, Li et al., published Oct. 18, 2012.

* cited by examiner

```
agaaacacct ccattttaga tttttttttt gttcttttcg gacggtgggt
cgtggagaga ttagcgtcta gttttcttaa aagaacaggc catttaggcc
ctgctttaca aaaggctcaa ccagtccaaa acgtctgcta ggatcaccag
ctgcaaagtt aagcgcgaga ccaccaaaac aggcgcattc gaactggaca
gacgctcacg caggagccca gcaccacagg cttgagcctg acagcggacg
tgagtgcgtg acacatgggg tcatctatgg gcgtcggagc aaggaagaga
gacgcacatg aacaccatga tgatgctatc aggcctgatg gagggagcaa
ccatgcacct tttcccctct ggaaattcat agctcacact tttttttaat
ggaagcaaga gttggcaaac acatgcattt tcaaacaagg aaaattaatt
ctcaaaccac catgacatgc aattctcaaa ccatgcaccg acgagtccat
gcgaggtgga aacgaagaac tgaaaatcaa catcccagtt gtcgagtcga
gaagaggatg acactgaaag tatgcgtatt acgatttcat ttacatacat
gtacaaatac ataatgtacc ctacaatttg tttttggag cagagtggtg
tggtcttttt tttttacacg aaaatgccat agctggcccg catgcgtgca
gatcggatga tcggtcggag acgacggaca atcagacact caccaactgc
ttttgtctgg gacacaataa atgtttttgt aaacaaaata aatacttata
aacgagggta ctagaggccg ctaacggcat ggccaggtaa acgcgctccc
agccgttggt ttgcgatctc gtcctcccgc acgcagcgtc gcctccaccg
tccgtccgtc gctgccacct ctgctgtgcg cgcgcacgaa gggaggaaga
acgaacgccg cacacacact cacacacgcc acactccccg tgggtcccct
ttccggcttg gcgtctatct cctctccccc gcccatcccc atgcactgca
ccgtacccgc cagcttccac ccccgccgca cacgttgctc cccctttctca
tcgcttctca attaatatct ccatcactcg ggttccgcgc tgcatttcgg
ccggcgggtt gagtgagatc tgggcgactg gctgactcaa tcactacgcg
gggatggcga cgttcgcggt gtccggcgcg actctcggtg tggcgcgggc
cggcgtcgga gtggcgcggg ccggctcgga gcggagggggc ggggcggact
tgccgtcgct gctcctcagg aagaaggact cctctcgtac gcctcgctct
ctcgaatctc ccccgtctgg ctttggctcc ccttctctct cctctgcgcg
cgcatggcct gttcgatgct gttccccaat tgatctccat gagtgagaga
gatagctgga ttaggcgatc gcgcttcctg aacctgtatt ttttcccccg
cggggaaatg cgttagtgtc acccaggccc tggtgttacc acggctttga
tcattcctcg tttcattctg atatatattt tctcattctt tttcttcctg
ttcttgctgt aactgcaagt tgtggcgttt tttcactatt gtagtcatcc
ttgcattttg caggcgccgt cctgagccgc gcggcctctc cagggaaggt
cctggtgcct gacggcgaga gngacgactt ggcaagtccg gcgcaacctg
aagaattaca ggtacacaca ctcgtgccgg taaatcttca tacaatcgtt
attcacttac caaatgccgg atgaaaccaa ccacggatgc gtcaggtttc
gagcttcttc tatcagcatt gtgcagtact gcactgcctt gttcattttg
ttagccttgg ccccgtgctg gctcttgggc cactgaaaaa atcagatgga
tgtgcattct agcaagaact tcacaacata atgcaccgtt tggggtttcg
tcagtctgct ctacaattgc tattttcgt gctgtagata cctgaagata
tcgaggagca aacggcggaa gtgaacatga cagggggac tgcagagaaa
cttcaatctt cagaaccgac tcagggcatt gtggaaacaa tcactgatgg
tgtaaccaaa ggagttaagg aactagtcgt ggggagaaa ccgcgagttg
tcccaaaacc aggagatggg cagaaaatat acgagattga cccaacactg
aaagattttc ggagccatct tgactaccgg taatgcctac ccgctgcttt
cgctcatttt gaattaaggt ccttttcatca tgcaaatttg gggaacatca
aagagacaaa gactagggac caccatttca tacagatccc ttcgtggtct
gagaatatgc tgggaagtaa atgtataatt gatgctaca atttgctcaa
aattgcaata cgaataactg tctccgatca ttacaattaa agagtggcaa
actgatgaaa atgtggtgga tgggttatag attttacttt gctaattcct
ctaccaaatt cctagggggg aaatctacca gttgggaaac ttagtttctt
atctttgtgg ccttttgtt ttggggaaaa cacattgcta aattcgaatg
attttgggta tacctcggtg gattcaacag atacagcgaa tacaagagaa
ttcgtgctgc tattgaccaa catgaaggtg gattggaagc attttctcgt
ggttatgaaa agcttggatt tacccgcagg taaatttaaa gctttattat
tatgaaacgc ctccactagt ctaattgcat atcttataag aaaatttata
attcctgttt tcccctctct ttttccagt gctgaaggta tcgtctaatt
gcatatctta taagaaaatt tatattcctg ttttccccta ttttccagtg
```

FIGURE 1

```
ctgaaggtat cacttaccga gaatgggctc cctggagcgc atgttatgtt
cttttaagtt ccttaacgag acaccttcca atttattgtt aatggtcact
attcaccaac tagcttactg gacttacaaa ttagcttact gaatactgac
cagttactat aaatttatga tctggctttt gcaccctgtt acagtctgca
gcattagtag gtgacttcaa caattggaat ccaaatgcag atactatgac
cagagtatgt ctacagcttg gcaattttcc acctttgctt cataactact
gatacatcta tttgtattta tttagctgtt tgcacattcc ttaaagttga
gcctcaacta catcatatca aaatggtata atttgtcagt gtcttaagct
tcagcccaaa gattctactg aatttagtcc atctttttga gattgaaaat
gagtatatta aggatgaatg aatacgtgca acactcccat ctgcattatg
tgtgcttttc catctacaat gagcatattt ccatgctatc agtgaaggtt
tgctcctatt gatgcagata tttgatatgg tcttttcagg atgattatgg
tgtttgggag attttcctcc ctaacaacgc tgatggatcc tcagctattc
ctcatggctc acgtgtaaag gtaagctggc caattattta gtcgaggatg
tagcattttc gaactctgcc tactaagggt ccctttcct ctctgttttt
tagatacgga tggatactcc atccggtgtg aaggattcaa tttctgcttg
gatcaagttc tctgtgcagg ctccaggtga aataccttc aatggcatat
attatgatcc acctgaagag gtaagtatcg atctacatta cattattaaa
tgaaatttcc agtgttacag ttttttaata cccacttctt actgacatgt
gagtcaagac aatactttg aatttggaag tgacatatgc attaattcac
cttctaaggg ctaaggggca accaacctg gtgatgtgtg tatgcttgtg
tgtgacataa gatcttatag ctcttttatg tgttctctgt tggttaggat
attccatttt ggcctttgt gaccatttac taaggatatt tacatgcaaa
tgcaggagaa gtatgtcttc caacatctca actaaacgac cagagtcact
aaggatttat gaatcacaca ttggaatgag cagcccggta tgtcaataag
ttatttcacc tgtttctggt ctgatggttt attctatgga ttttctagtt
ctgttatgta ctgttaacat attacatggt gcattcactt gacaacctcg
attttatttt ctaatgtctt catattggca agtgcaaaac tttgcttcct
ctttgtctgc ttgttctttt gtcttctgta agatttccat tgcatttgga
ggcagtgggc atgtgaaagt catatctatt ttttttttgt cagagcatag
ttatatgaat tccattgttg ttgcaatagc tcggtataat gtaaccatgt
tactagctta agatttccca cttaggatgt aagaaatatt gcattggagc
gtctccagca agccatttcc taccttatta atgagagaga gacaaggggg
gggggggggg gggggttccc ttcattattc tgcgagcgat tcaaaaactt
ccattgttct gaggtgtacg tactgcaggg atctcccatt atgaagagga
tatagttaat tctttgtaac ctacttggaa acttgagtct tgaggcatcg
ctaatatata ctatcatcac aatacttaga ggatgcatct gaanatttta
gtgtgatctt gcacaggaac cgaagataaa ttcatatgct aatttaggg
atgaggtgtt gccaagaatt aaaaggcttg gatacaatgc agtgcagata
atggcaatcc aggagcattc atactatgca agctttgggt attcacacaa
tccatttttt tctgtataca cntcttcacc catttggagc tattacatcc
taatgcttca tgcacataaa atatttggat ataatccttt attagatata
tagtacaact acacttagta ttctgannaa naagatcatt ttattgttgt
tggcttgttc caggtaccat gttactaatt tttttgcacc aagtagccgt
tttggaactc cagaggactt aaaatccttg atcgatagag cacatgagct
tggtttgctt gttcttatgg atattgttca taggtaatta gtccaattta
attttagctg ttttactgtt tatctggtat tctaaaggga aattcaggca
attatgatac attgtcaaaa gctaagagtg gcgaaagtga aatgtcaaaa
tctagagtgg cataaggaaa attggcaaaa actagagtgg caaaaataaa
attttcccat cctaaatggc agggccctat cgccgaatat ttttccattc
tatataattg tgctacgtga cttcttttt ctcagatgta ttaaaccagt
tggacatgaa atgtatttgg tacatgtagt aaactgacag ttccatagaa
tatcgttttg taatggcaac acaatttgat gccatagatg tggattgaga
agttcagatg ctatcaatag aattaatcaa ctggccatgt actcgtggca
ctacatatag tttgcaagtt ggaaaactga cagcaatacc tcactgataa
gtggccaggc cccacttgcc agcttcatac tagatgttac ttccctgttg
aattcatttg aacatattac ttaaagttct tcatttgtcc taagtcaaac
ttcttttaagt ttgaccaagt ctattggaaa atatatcaac atctacaaca
ccaaattact ttgatcagat taacaatttt tatttatta tattagcaca
```

```
tctttgatgt tgtagatatc agcacatttt tctatagact tggtcaaata
tagagaagtt tgacttagga caaatctaga acttcaatca atttggatca
gagggaacat caaataatat agatagatgt caacacttca acaaaaaaat
cagaccttgt caccatatat gcatcagacc atctgtttgc tttagccact
tgctttcata tttatgtgtt tgtacctaat ctacttttcc ttctacttgg
tttggttgat tctatttcag ttgcattgct tcatcaatga ttttgtgtac
cctgcagtca ttcgtcaaat aatacccttg acggtttgaa tggtttcgat
ggcactgata cacattactt ccacggtggt ccacgcggcc atcattggat
gtgggattct cgtctattca actatgggag ttgggaagta tgtagctctg
acttctgtca ccatatttgg ctaactgttc ctgttaatct gttcttacac
atgttgatat tctattctta tgcaggtatt gagattctta ctgtcaaacg
cgagatggtg gcttgaagaa tataagtttg atggatttcg atttgatggg
gtgacctcca tgatgtatac tcaccatgga ttacaagtaa gtcatcaagt
ggtttcagta acttttttag ggcactgaaa caattgctat gcatcataac
atgtatcatg atcaggactt gtgctacgga gtcttagata gttccctagt
atgcttgtac aattttacct gatgagatca tggaagattg gaagtgatta
ttatttattt tctttctaag tttgtttctt gttctagatg acatttactg
ggaactatgg cgaatatttt ggatttgcta ctgatgttga tgcggtagtt
tacttgatgc tggtcaacga tctaattcat ggactttatc ctgatgctgt
atccattggt gaagatgtaa tgcttaacag tatttatgat ttttaactag
ttaagtagtt ttattttggg gatcagtctg ttacactttt tgttaggggt
aaaatctctc ttttcataac aatgctaatt tataccttgt atgataatgc
atcacttang taatttgaaa agtgcaaggg cattcaagct tacgagcata
tttttttgatg gctgtaattt atttgatagt atgcttgttt gggtttttca
ataagtggga gtgtgtgact aatgttgtat tatttattta attgcggaag
aaatgggcaa ccttgtcaat tgcttcagaa ggctaacttt gattccataa
acgctttgga aatgagaggc tattcccaag gacatgaatt atacttcagt
gtgttctgta catgtatttg taatagtggt ttaacttaaa ttcctgcact
gctatggaat ctcactgtat gttgtnagtg tacacatcca caaacaagta
atcctgagct ttcaactcat gagaaaatan gangtccgct tctgccagca
ttaactgttc acagttctaa tttgtgtaac tgtgaaattg ttcaggtcag
tggaatgcct acattttgca tccctgttcc agatggtggt gttggttttg
actaccgcct gcatatggct gtagcagata aatggattga actcctcaag
taagtgcagg aatattggtg attacatgcg cacaatgatc tagattacat
tttctaaatg gtaaaaagga aaatatgtat gtgaatatct agacatttgc
ctgttatcag cttgaatacg agaagtcaaa tacatgattt aaatagcaaa
tctcggaaat gtaatggcta gtgtctttat gctgggcagt gtacattgcg
ctgtagcagg ccagtcaaca cagttagcaa tatttcaga aacaatatta
tttatatccg tatatganga aagttagtat ataaactgtg gtcattaatt
gtgttcacct tttgtcctgt ttaaggatgg gcagtaggta ataaatttag
ccagataaaa taaatcgtta ttaggtttac aaaaggaata tacagggtca
tgtagcatat ctagttgtaa ttaatgaaaa ggctgacaaa aggctcggta
aaaaaaactt tatgatgatc cagatagata tgcaggaacg cgactaaagc
tcaaatactt attgctacta cacagctgcc aatctgtcat gatctgtgtt
ctgctttgtg ctatttagat ttaaatacta actcgataca ttggcaataa
taaacttaac tattcaacca atttggtgga taccaganat ttctgccctc
ttgttagtaa tgatgtgctc cctgctgctg ttctctgccg ttacaaaagc
tgttttcagt tttttgcatc attattttg tgtgtgagta gtttaagcat
gttttttgaa gctgtgagct gttggtactt aatacattct tggaagtgtc
caaatatgct gcagtgtaat ttagcatttc tttaacacag gcaaagtgac
gaatcttgga aaatgggcga tattgtgcac accctaacaa atagaaggtg
gcttgagaag tgtgtaactt atgcagaaag tcatgatcaa gcactagttg
gtgacaagac tattgcattc tggttgatgg ataaggtact agctgttact
tttggacaaa agaattactc cctcccgttc ctaaatataa gtctttgtag
agattccact atggaccaca tagtatatag atgcatttta gagtgtagat
tcactcattt tgcttcgtat gtagtccata gtgaaatctc tacagagact
tatatttagg aacggaggga gtacataatt gatttgtctc atcagattgc
tagtgttttc ttgtgataaa gattggctgc ctcacccatc accagctatt
tcccaactgt tacttgagca gaatttgctg aaaacgtacc atgtggtact
```

```
gtggcggctt gtgaactttg acagttatgt tgcaattttc tgttcttatt
tatttgattg cttatgttac cgttcatttg ctcattcctt tccgagacca
gccaaagtca cgtgttagct gtgtgatctg ttatctgaat cttgagcaaa
ttttattaat aggctaaaat ccaacgaatt atttgcttga atttaaatat
acagacgtat agtcacctgg ctctttctta gatgattacc atagtgcctg
aaggctgaaa tagttttggt gtttcttgga tgccgcctaa aggagtgatt
tttattggat agattcctgg ccgagtcttc gttacaacat aacatttggg
agatatgctt agtaacagct ctgggaagtt tggtcacaag tctgcatcta
cacgctcctt gaggttttat tatggcgcca tctttgtaac tagtggcacc
tgtaaggaaa cacattcaaa aggaaacggt cacatcattc taatcaggac
caccatacta agagcaagat tctgttccaa ttttatgagt ttttgggact
ccaagggaa caaagtgtc tcatattgtg cttataacta cagttgtttt
tataccagtg tagttttatt ccaggacagt tgatacttgg tactgtgctg
taaattattt atccgacata gaacagcatg aacatatcaa gctctctttg
tgcaggatat gtatgatttc atggctctgg ataggcttca actcttcgca
ttgatcgtgg catagcatta cataaaatga tcaggcttgt caccatgggt
ttaggtggtg aaggctatct taacttcatg ggaaatgagt ttgggcatcc
tggtcagtct ttacaacatt attgcattct gcatgattgt gatttactgt
aatttgaacc atgcttttct ttcacattgt atgtattatg taatctgttg
cttccaagga ggaagttaac ttctatttac ttggcagaat ggatagattt
tccaagaggc ccacaaactc ttccaaccgg caaagttctc ccctggaaat
aacaatagtt atgataaatg ccgccgtaga tttgatcttg taagttttag
ctgtgctatt acattccctc actagatctt tattggccat ttatttcttg
atgaaatcat aatgtttgtt aggaaagatc aacattgctt ttgtagtttt
gtagacgtta acataagtat gtgttgagag ttgttgatca ttaaaaatat
catgattttt tgcagggaga tgcagatttt cttagatatc gtggtatgca
agagttcgat caggcaatgc agcatcttga ggaaaaatat ggggtatgtc
actggtttgt ctttgttgca taacaagtca cagtttaacg tcagtctctt
caagtggtaa aaaaagtgta gaattaattc ctgtaatgag atgaaaactg
tgcaaaggcg gagctggaat tgcttttcac caaaactatt ttcttaagtg
cttgtgtatt gatacatata ccagcactga caatgtaact gcagtttatg
acatctgagc accagtatgt ttcacggaaa catgaggaag ataaggtgat
catcctcnaa aagaggagat tggtatttg ttttcaactt ccactggagc
aatagctttt ttgactaccg tgttgggtgt tccaagcctg ggaagtacaa
ggtatgcttg cctttcatt gtccaccctt caccagtagg gttagtgggg
gcttctacaa cttttaattc cacatggata gagtttgttg gtcgtgcagc
tatcaatata aagaataggg taatttgtaa agaaaagaat ttgctcgagc
tgttgtagcc ataggaaggt tgttcttaac agccccgaag cacataccat
tcattcatat tatctactta agtgtttgtt tcaatcttta tgctcagttg
gactcggtct aatactagaa ctattttccg aatctaccct aaccatccta
gcagttttag agcagcccca tttggacaat tggctgggtt tttgttagtt
gtgacagttt ctgctatttc ttaatcaggt ggccttggac tctgacgatg
cactctttgg tggattcagc aggcttgatc atgatgtcga ctacttcaca
accgtaagtc tgggctcaag cgtcacttga ctcgtcttga ctcaactgct
tacaaatctg aatcaacttc ccaattgctg atgcccttgc aggaacatcc
gcatgacaac aggccgcgct ctttctcggt gtacactccg agcagaactg
cggtcgtgta tgcccttaca gagtaagaac cagcagcggc ttgttacaag
gcaaagagag aactccagag agctcgtgga tcgtgagcga agcgacgggc
aacggcgcga ggctgctcca agcgccatga ctgggagggg atcgtgcctc
ttccccagat gccaggagga gcagatggat aggtagcttg ttggtgagcg
ctcgaaagaa aatggacggg cctgggtgtt tgttgtgctg cactgaaccc
tcctcctatc ttgcacattc ccggttgttt ttgtacatat aactaataat
tgcccgtgcg ctcaacgtga aaatcc
```

```
aagctttgta gccttgcacg ggctccccaa caaactgcct cactcgattg tcaaaaaagt
aaaaatgatt gtagaaaaaa aaactgactc actcgtcact accctaccgt cctacatgac
acctggccgc aagacgacgc cgtcctcctg ccgcgcgcgt ccgcgatcac accaccgcaa
aaaccaaaac ctcttcgccg gtgcgtccca cgctaccatc catgcagccg tccgcccgcg
cgcgcgttgc ccgcaccacc cgctggcggc caccacgccg ccactctcgc gtgaaggctc
cgtccgcttc ctcctagttc cactctctct ccgtgctagc agtatatagc atccgccctc
cgccccctcc caatcttaga acacccctcc ctttgcctcc tcatttcgct cgcgtgggtt
taagcaggag acgaggcggg gtcagttggg cagttaggtt ggatccgatc cggctgcggc
ggcggcgacg ggatggctgc gccggcattc gcagtttccg cggcggggct ggcccggccg
tcggctcctc gatccggcgg ggcagagcgg aggggcgcg gggtggagct gcagtcgcca
tcgctgctct tcggccgcaa caagggcacc cgttcacccc gtaattattt gcgccacctt
tctcactcac attctctcgt gtattctgtc gtgctcgccc ttcgccgacg acgcgtgccg
attccgtatc gggctgcggt gttcagcgat cttacgtcgg ttccctcctg gtgtggtgat
gtctgtaggt gccgtcggcg tcggaggttc tggatggcgc gtggtcatgc gcgcgggggg
gccgtccggg gaggtgatga tccctgacgg cggtagtggc ggaacaccgc cttccatcga
cggtcccgtt cagttcgatt ctgatgatct gaaggtagtt ttttttttgc atcgatctga
aggtacttga catatactac tgtattaccc tgagtaaata ctgccaccat attttatgg
ttcgcttgaa atacctgttt acttgctacg gttttcactt tcattgagac gtcggacgaa
attcactgaa ttcctataat ttggtagaca ccgaaatata tactactcct tccgtcccat
aatataagag cgttttggc accttatatt ataggcgga gggagtacct tttaggtcaa
aatattgtgg tagtttcaat tgtatacaag aattcaaata ttttttttaa aaaaaaatca
actaattggt tgagtttcaa gtgaagcgtt ttggtccttt ggctgagatg taaaccgaaa
tcactgaaat tcatagtagc cgaaacttta ataagaactga aactcaaaat ctgctatccg
gcgaaattct aaagatttgc ttatttcaca cgtaggttgc agtacaccct ctttctaatt
tattggggaa ggggtattat tatcttgtta gtacctgcct gcatgacaat tgaaatctaa
gacaaaacac catatgcgag gcctacacac ggtaggttgg tttacaacta tgtgtgccac
agttcgtctg aacttttgt ccttcacatc gtgttaggtt ccattcattg atgatgaaac
aagcctacag gatggaggtg aagatagtat ttggtcttca gagacaaatc aggttagtga
agaaattgat gctgaagaca cgagcagaat ggacaaagaa tcatctacga gggagaaatt
acgcattctg ccaccaccgg gaaatggaca gcaaatatac gagattgacc caacgctccg
agactttaag taccatcttg agtatcggta tgcttcgctt ctattgtgtg cacttttaaa
acaatttaca gtctttgata agatgtgaat ggctgcttgc tgtgacacga aactcttgaa
gttcgtagtc actcttgtgt gttcatggtt ctgaggtaac atggtaaccg aacaaaaata
ggaaagtggc aagcactgca atgtgagcta ctgataacca cccattgtaa ttgggtacac
tgattaatat atatgtcttc atgggctcta ttttttttca atatctatgc caattgaaca
acaatgcttt gtggacgggt gttcttttac cctcttcttc tatcaataga tgatatgcat
actcatgcgt atcctacaaa aaattgaaca acaatgccac tttcccccgt gttgctttg
taaggatgaa acacatatgt ccagatcaaa ctatactagc agtctaactg tgccttaatg
gatcaaaaac agatatagcc tatacaggag aatacgttca gacattgatg aacacgaagg
aggcatggat gtattttccc gcggttacga gaagtttgga tttatgcgca ggtgaaattt
cttgactaaa taactatgta tctaccctt ctttgtactc tatcaacatt cctcttccca
tgcagcgctg aaggtatcac ttaccgagaa tgggctcctg gagcagatgt acgttcttct
aaccatctga tcgtttacct gactatacta attctatctt tcaactaatt gtgaataatt
actgctcatc agctatccta aggttgggga ttttgcacct cccagatgaa cagcatatta
agtcgcacaa ctagcattat taagaactaa ctcctgcttc caattgcagt ctgcagcatt
agttggcgac ttcaacaatt gggatccaaa tgcagaccat atgagcaaag tatgcatgta
gtttcacaaa tatatcatat tttctttgta gattttttt tttagatcgg cttatctatt
acgttgagct gtaaatatag ttggaagtgt ttaggagtat taaattcact ggactctatt
cttcacttg cctgttgcac gagcccatta ctagatatca atgttgatga tgcttttgtt
gtatgaggtc gaagtgaaac atgcagtta cccttttata taagtaaggt tgcacatgta
ttttttatga tctaaacatt atttactgat tttgttcttg caagacacta agcagtttta
cataataatg gcgtggagc aggccgactg cacatctgaa ctgtagctcc atgtggttga
tatagattac aaatgctcat attcaatgta actgttttca gaatgacctt ggtgtttggg
agatttttct gccaaacaat gcagatggtt cgccaccaat tcctcacggc tcacgggtga
aggttgtttt cttctccttg ccaacggtgt taggctcagg aacatgtcct gtattactca
gaagctcttt tgaacatcta ggtgagaatg gatactccat ctgggataaa ggattcaatt
cctgcttgga tcaagtactc cgtgcagact ccaggagata taccatacaa tggaatatat
tatgatcctc ccgaagaggt attttacttc atcttctgtg cttttagatt tcagatattt
ttattagaag aaaattatga tttttttcct cacgaaccttt cccaattgct atttcaagct
gtcctactta tttgctgctg gcatctcatt tttctattct ctaaccagtt atgaaattcc
ttacatgcat atgcaggaga agtatgtatt caagcatcct caacctaaac gaccaaaatc
attgcggata tatgaaacac atgttggcat gagtagcccg gtatttcatc tttaccatgt
attccataaa tgaagttagc tatatgcagt tcaaatttat ttacaggttg ttacaatggt
attttgtgt tggtgcccctt ctttcgtttt ataagtaaaa aacttatcat aaattttattt
```

FIGURE 2

```
gttatgccgc ttggttaata caatctgaaa aatgtaactg tggacaatct agaactagat
aatacaaatc tgaaaaaaca tgctggaata gtgtcatttc agtcaactag gatgttttga
atgctcaaga gaagtactag tgtgtagcat caaaagctgg tgtccatttg ttcaaatgtt
taattaacac tatagtgaaa acaagtaatt gcacaaagaa acaagtaatt gcccaagttc
atatgttttt tcactatatt acatgtttca tcaacaattt aattaacctc attccttaca
aacatttgta tttacatttg ttcctacata tatagttatt ttatatatca actttataaa
tcatgactgt tataattaaa accgatggta tatcaacgat tgagataatt tggcatatgt
ggatgaattt tgtggcttgt tatgctcttg ttttaataac ataataaata gattatgctt
gttggtagcc tttttacatt aacacatggg caattacttg tttctttgtg caaccaggaa
ccaaagatcg acacatatgc aaacttcagg gatgaggtgc ttccaagaat taaaagactt
ggatacaatg cagtgcaaat aatggcaatc caagagcact catactatgg aagctttggg
tagttctctg ggtcgatttc tggttctttt agttatcttt tgtccataga acatatttca
actttagcaa ctatactatt atattaactt ttcagctatt gtcttncttt ttcttatgtg
agagactgct gcntcttgct acttcctgtg ttctcattca gagtanacat cttatganta
gacaactcta tgtngacatt ccggaagtat ncactggctg attcggtcta aaataacata
ctgctcagat agccacataa cagtacgatt acacacataa tgaccatgtt tgcatagagt
ggcggtagta tgttcctcac catactagca taatgacttg ttatataaga gtatatcata
ttaacttctt ttccaatgac atggaagctg taacaacttt caaatcattt ttgtcttta
agtgctgctt ttttcctgtt tgacaattaa tacaatacca cttttatgtg tttttacttc
tattgcaggt accatgttac caatttcttt gcaccaagta gccgttttgg gtccccagaa
gatttaaaat ctttgattga tagagctcac gagcttggct tggttgtcct catggatgtt
gttcacaggt acttaatgta atttgaggtt ggcgtgttaa gttcacatta atcttaattc
tttatttcaa ttcctatggc ctctctccta gattggaaca gtaaaagcat catccagttt
gtataaattg ctaaaagaac attttacatg ttaagtattt tcaattacta tgaaacatat
aaatttacat acttattgat tttacgacag aagtaccgat ctcacaagat gaacaattgg
ttgatcacat atcatttcat actacaatac aagaaaatga atagagaacg agttaatatt
agccttggta aaatcagcaa cttgtttgga aataaagtat agtgatgcca gtgcaaanaa
caaggcatca agttggtttc agctcccacg gtcggtgcta gctgtcaagg gtaatttgca
cgtagtcgca catagatttg tgtgggagtg gaaagtaacc acagattgtc cgaggaacac
gggacacacg tcttagccac aggtttgggc tccccttgat gcgggtagta gctttactcc
ttatatgaaa ttatctcaag atagatttca atttggggtt acacttanga actcancaag
ttaaggatca actcnctgag ttctatacga ctgatctttg accgagatat cttgatcagg
ctaagtanca aaatccaggc cttgagatgt tgaacatgtc cttcattttg ggctgggtgc
ccttgggcat aaggtgtngt ccttccttca tgtgcttctt gcagcgtatg acataaacnt
cctctgagtt ggtanatgca cggttccctt tgaggaaatc aggggtagtc gcatctnggg
aaagttggtc acccangcat ggatcctcng cgcacaccgg gcaaacacgg tgaaaccact
tctcctcgac actagctaac ttgacattca agcaaactaa gaatataact ttatntctaa
atgaaccgga caccctcctt gtgcctgcac ctacagagta caatgccagt tttggactga
actcttgtgt tcatgtatgt gctaatnaca taggttctaa ccatgattct aaatagcgcg
ttataactcc actatagtaa tgctatagcg tttanaagat cccgcactaa gggaccttag
tccaaataca tgatcaaaca ttttacatag cgcgctatag ctatttaaaa ctatggtcac
ccgctaagag gcataactcg ctatttaaaa ctatggttct aactttaat ctattttatg
tcttggtcca aagccccttt ttgttctata gctttacctt tgggttgaga tcacccttaa
cccattggta atcctggttg atttactcca tcctttcttg cgtagcttta cttttggttt
tttgtttctc acagtcacgc gtcaaataat accttggacg
```

A
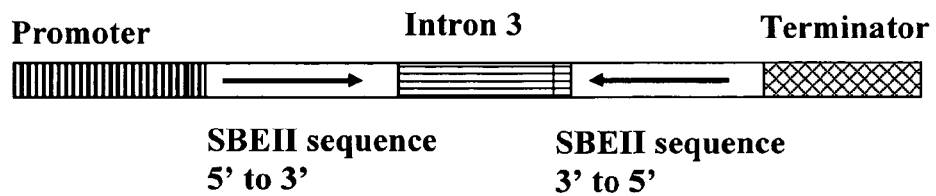
B
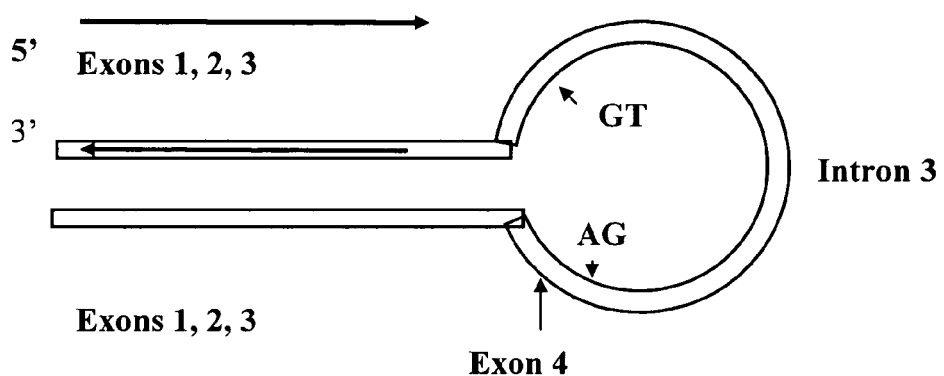
FIGURE 3

```
cgtgggttta agcaggagac gaggcggggt cagttgggca gttaggttgg
atccgatccg gctgcggcgg cggcgacggg atggctgcgc cggcattcgc
agtttccgcg gcggggctgg cccggccgtc ggctcctcga tccggcgggg
cagagcggag ggggcgcggg gtggagctgc agtcgccatc gctgctcttc
ggccgcaaca agggcacccg ttcaccccgt gccgtcggcg tcggaggttc
tggatggcgc gtggtcatgc gcgcgggggg gccgtccggg gaggtgatga
tccctgacgg cggtagtggc ggaacaccgc cttccatcga cggtcccgtt
cagttcgatt ctgatgatct gaaggttcca ttcattgatg atgaaacaag
cctacaggat ggaggtgaag atagtatttg gtcttcagag acaaatcagg
ttagtgaaga aattgatgct gaagacacga gcagaatgga caaagaatca
tctacgaggg agaaattacg cattctgcca ccaccgggaa atggacagca
aatatacgag attgacccaa cgctccgaga ctttaagtac catcttgagt
atcgatatag cctatacagg agaatacgtt cagacattga tgaacacgaa
ggaggcatgg atgtattttc ccgcggttac gagaagtttg gatttatgcg
cagcgctgaa ggtatcactt accgagaatg ggctcctgga gcagattctg
cagcattagt tggcgacttc aacaattggg atccaaatgc agaccatatg
agcaaaaatg accttggtgt ttgggagatt tttctgccaa acaatgcaga
tggttcgcca ccaattcctc acggctcacg ggtgaaggtg cgaatgggta
ctccatctgg gacaaaggat tcaattcctg cttggatcaa gtactccgtg
cagactccag gagatatacc atacaatgga atatattatg atcctcccga
agaggagaag tatgtattca agcatcctca acctaaacga ccaaaatcat
tgcggatata tgaaacacat gttggcatga gtagcccgga accaaagatc
aacacatatg caaacttcag ggatgaggtg cttccaagaa ttaaaagact
tggatacaat gcagtgcaaa taatggcaat ccaagagcac tcatactatg
gaagctttgg gtaccatgtt accaatttct ttgcaccaag tagccgtttt
gggtccccag aagatttaaa atctttgatt gatagagctc acgagcttgg
cttggttgtc ctcatggatg ttgttcacag tcacgcgtca ataatacct
tggacgggtt gaatggtttt gatggcacgg atacacatta cttccatggc
ggttcacggg gccatcactg gatgtgggat tcccgtgtgt ttaactatgg
gaataaggaa gttataaggt ttctactttc caatgcaaga tggtggctag
aggagtataa gtttgatggt ttccgattcg atggcgcgac ctccatgatg
tatcccatc atggattaca agtaacctt acaggaagct accatgaata
ttttggcttt gccactgatg tagatgcggt cgtttacttg atgctgatga
atgatctaat tcatgggttt tatcctgaag ccgtaactat cggtgaagat
gttagtggaa tgcctacatt tgcccttcct gttcaagttg gtggggttgg
ttttgactat cgcttacata tggctgttgc ccgcaaatgg attgaacttc
tcaaaggaaa cgatgaagct tgggagatgg gtaatattgt gcacacacta
acaaacagaa ggtggctgga aaagtgtgtt acttatgctg aaagtcacga
tcaagcactt gttggagaca agactattgc attctggttg atggacaagg
atatgtatga tttcatggcg ctgaacggac cttcgacgcc taatattgat
cgtggaatag cactgcataa aatgattaga cttatcacaa tgggtctagg
aggagagggt tatcttaact ttatgggaaa tgagttcggg catcctgaat
ggatagactt tccaagaggc ccacaagtac ttccaagtgg taagttcatc
ccaggaaaca acaacagtta cgacaaatgc cgtcgaagat tgacctggg
tgatgcagaa tttcttaggt atcatggtat gcagcagttt gatcaggcaa
tgcagcatct tgaggaaaaa tatggtttta tgacatcaga ccaccagtac
gtatctcgga aacatgagga agataaggtg atcgtgtttg aaaaggggga
cttggtatt gtgttcaact tccactggag tagtagctat ttcgactacc
gggtcggctg tttaaagcct gggaagtaca aggtggtctt agactcggac
```

Figure 9

```
gctggactct ttggtggatt tggtaggatc catcacactg cagagcactt
cacttctgac tgccaacatg acaacaggcc ccattcattc tcagtgtaca
ctcctagcag aacctgtgtt gtctatgctc caatgaacta acagcaaagt
gcagcatacg cgtgcgcgct gttgttgcta gtagcaagaa aaatcgtatg
gtcaatacaa ccaggtgcaa ggtttaataa ggattttttgc ttcaacgagt
cctggataga caagacaaca tgatgttgtg ctgtgtgctc ccaatcccca
gggcgttgtg aagaaaacat gctcatctgt gttattttat ggatcagcga
cgaaacctcc cccaaatacc cctttttttt tt
```

METHOD AND MEANS FOR IMPROVING BOWEL HEALTH

This application is a divisional of U.S. application Ser. No. 11/324,063, filed Dec. 30, 2005, now U.S. Pat. No. 7,700,139 which claims the benefit of U.S. Provisional Application No. 60/688,944, filed Jun. 8, 2005; and claims priority of Australian Provisional Application No. 2004907350, filed Dec. 30, 2004, the content of all of which are hereby incorporated by reference into the subject application.

FIELD OF THE INVENTION

This invention relates to methods of improving the health of mammals including humans by the use of diets including modified wheat. The invention also relates to wheat products with properties including increased levels of resistant starch or a high relative amylose content that provide for improved bowel health.

BACKGROUND OF THE INVENTION

Serious non-infectious chronic illnesses relating to diet and lifestyle are major causes of morbidity and mortality in affluent industrialised countries and also in emerging ones with greater affluence. These include coronary heart disease, diverticular disease, certain cancers (especially of the colon and rectum) and diabetes. Cereal foods have significant potential to improve human health through lowering the risk of these conditions. The benefits may be obtained through consumption of processed foods containing whole grains or their constituents including complex carbohydrates—starch and non-starch polysaccharides (NSP, major components of dietary fibre). NSP are resistant to digestion by human small intestinal enzymes which helps to explain their effectiveness in increasing faecal bulk and relieving constipation (Topping & Clifton, 2001). While starch can be digested (theoretically to completion) in the human small intestine, some escapes into the large bowel. This fraction is resistant starch (RS) which, together with a variable fraction of NSP, is metabolised by the large bowel microflora (Topping & Clifton, 2001). Short chain fatty acids (SCFA) are major end products of this fermentation and they promote important aspects of large bowel function-stimulation of fluid and electrolyte absorption, modulation of muscular contraction and visceral perfusion (Topping & Clifton, 2001). One of the principal SCFA, butyrate, may also play a role in promoting a normal phenotype in colonocytes, and enhancing normally controlled colonocyte proliferation and lowering the risk of colorectal cancer. The latter malignancy is a substantial cause of early morbidity in affluent industrialised countries. A further consequence of slower starch small intestinal digestibility is the potential to lower the rate of entry of glucose into the circulation and, thus, a lesser demand for insulin. This is measured as glycaemic index (GI) which is emerging as a substantial factor in disease risk.

It is emerging also that many of the actions ascribed to dietary fibre may actually be due to RS (Topping & Clifton, 2001). RS intakes are low in populations at high risk of the diseases of affluence and modification of convenience foods to enhance the content and action of RS is considered to be an effective means of improving nutrition for public health at the population level. This may be put into practice through encouraging the consumption of specific foods, such as beans or wholegrain (brown) rice, which are intrinsically high in RS. Another approach is to enrich convenience foods with RS as an added ingredient.

Wheat is a staple food in many countries and supplies approximately 20% of the food kilojoules for the total world population. The processing characteristics of wheat make it the preferred base for most cereal-based processed products such as bread, pasta and noodles. Wheat consumption is increasing world-wide with increasing affluence. Breadwheat (*Triticum aestivum*) is a hexaploid having three different genomes, A, B and D, and most of the known genes in wheat are present in triplicate, one on each genome. The hexaploid nature of the breadwheat genome makes finding and combining gene mutations in each of the three genomes a challenge. The presence of three genomes has a buffering effect by masking mutations in individual genomes, in contrast to the more readily identified mutations in diploid species. Known variation in wheat starch structure has been limited relative to the variation available in maize or rice. Another contributing factor to this is that the transformation efficiency of wheat has lagged behind that for other cereals.

The synthesis of starch in the endosperm of higher plants is carried out by a suite of enzymes that catalyse four key steps. Firstly, ADP-glucose pyrophosphorylase activates the monomer precursor of starch through the synthesis of ADP-glucose from G-1-P and ATP. Secondly, the activated glucosyl donor, ADP-glucose, is transferred to the non-reducing end of a pre-existing $\alpha$1-4 linkage by starch synthases. Thirdly, starch branching enzymes introduce branch points through the cleavage of a region of $\alpha$-1,4 linked glucan followed by transfer of the cleaved chain to an acceptor chain, forming a new $\alpha$-1,6 linkage. Starch branching enzymes are the only enzymes that can introduce the $\alpha$-1,6 linkages into $\alpha$-polyglucans and therefore play an essential role in the formation of amylopectin. Finally, starch debranching enzymes remove some of the branch linkages although the mechanism through which they act is unresolved (Myers et al., 2000).

While it is clear that at least these four activities are required for normal starch granule synthesis in higher plants, multiple isoforms of each of the four activities are found in the endosperm of higher plants and specific roles have been proposed for individual isoforms on the basis of mutational analysis (Wang et al, 1998, Buleon et al., 1998) or through the modification of gene expression levels using transgenic approaches (Abel et al., 1996, Jobling et al., 1999, Sewall et al., 2000). However, the precise contributions of each isoform of each activity to starch biosynthesis are still not known, and it is not known whether these contributions differ markedly between species. In the cereal endosperm, two isoforms of ADP-glucose pyrophosphorylase are present, one form within the amyloplast, and one form in the cytoplasm (Denyer et al., 1996, Thorbjornsen et al., 1996). Each form is composed of two subunit types. The shrunken (sh2) and brittle (bt2) mutants in maize represent lesions in large and small subunits respectively (Giroux and Hannah, 1994). Four classes of starch synthase are found in the cereal endosperm, an isoform exclusively localised within the starch granule, granule-bound starch synthase (GBSS), two forms that are partitioned between the granule and the soluble fraction (SSI, Li et al., 1999a, SSII, Li et al., 1999b) and a fourth form that is entirely located in the soluble fraction, SSIII (Cao et al, 2000, Li et al., 1999b, Li et al, 2000). GBSS has been shown to be essential for amylose synthesis (Shure et al., 1983), and mutations in SSII and SSIII have been shown to alter amylopectin structure (Gao et al, 1998, Craig et al., 1998). No mutations defining a role for SSI activity have been described.

Three forms of branching enzyme are expressed in the cereal endosperm, branching enzyme I (SBEI), branching enzyme IIa (SBEIIa) and branching enzyme IIb (SBEIIb) (Hedman and Boyer, 1982, Boyer and Preiss, 1978, Mizuno et al., 1992, Sun et al., 1997). Genomic and cDNA sequences have been characterized for rice (Nakamura and Yamanouchi, 1992), maize (Baba et al., 1991; Fisher et al., 1993; Gao et al., 1997) and wheat (Repellin et al., 1997; Nair et al., 1997; Rahman et al., 1997). Sequence alignment reveals a high degree of sequence similarity at both the nucleotide and amino acid levels and allows the grouping into the SBEI, SBEIIa and SBEIIb classes. SBEIIa and SBEIIb generally exhibit around 80% sequence identity to each other, particularly in the central regions of the genes. SBEIIa and SBEIIb may also be distinguished by their expression patterns. SBEIIb in maize is specifically expressed in endosperm while SBEIIa is present in every tissue of the plant.

In wheat endosperm, SBEI (Morell et al, 1997) is found exclusively in the soluble fraction, while SBEIIa and SBEIIb are found in both soluble and starch-granule associated fractions (Rahman et al., 1995). In maize and rice, high amylose phenotypes have been shown to result from lesions in the SBEIIb gene, also known as the amylase extender (ae) gene (Boyer and Preiss, 1981, Mizuno et al., 1993; Nishi et al., 2001). In these SBEIIb, mutants, endosperm starch grains showed an abnormal morphology, amylose content was significantly elevated, the branch frequency of the residual amylopectin was reduced and the proportion of short chains (<DP17, especially DP8-12) was lower. Moreover, the gelatinisation temperature of the starch was increased. In addition, there was a significant pool of material that was defined as "intermediate" between amylose and amylopectin (Boyer et al., 1980, Takeda, et al., 1993b). In contrast, maize plants mutant in the SBEIIa gene due to a mutator (Mu) insertional element and consequently lacking in SBEIIa protein expression were indistinguishable from wild-type plants in the branching of endosperm starch (Blauth et al., 2001), although they were altered in leaf starch. Similarly, rice plants deficient in SBEIIa activity exhibited no significant change in the amylopectin chain profile in endosperm (Nakamura 2002). In both maize and rice, the SBEIIa and SBEIIb genes are not linked in the genome.

Mutations in wheat SBEIIa or SBEIIb or the phenotypes of wheat lines carrying these mutations have not been reported. Known mutants in wheat are for the waxy gene (GBSS, Zhao and Sharp, 1998) and a mutant entirely lacking the SGP-1 protein (Yamamori et al, 2000) which was produced by crossing lines which were lacking the A, B and D genome specific forms of SGP-1 (SSII) protein as assayed by protein electrophoresis. Examination of the SSII null seeds showed that the mutation resulted in alterations in amylopectin structure, deformed starch granules, and an elevated relative amylose content to about 30-37% of the starch, which was an increase of about 8% over the wild-type level (Yamamori et al., 2000). Amylose was measured by colorimetric measurement, amperometric titration (both for iodine binding) and a concanavalin A method. Starch from the SSII null mutant exhibited a decreased gelatinisation temperature compared to starch from an equivalent, non-mutant plant. Starch content was reduced from 60% in the wild-type to below 50% in the SSII-null grain.

In maize, the dull1 mutation causes decreased starch content and increased amylose levels in endosperm, with the extent of the change depended on the genetic background, and increased degree of branching in the remaining amylopectin (Shannon and Garwood, 1984). The gene corresponding to the mutation was identified and isolated by a transposon-tagging strategy using the transposon mutator (Mu) and shown to encode the enzyme designated starch synthase II (SSII) (Gao et al., 1998). The enzyme is now recognized as a member of the SSIII family in cereals (Li et al., 2003). Mutant endosperm had reduced levels of SBEIIa activity associated with the dull1 mutation. No corresponding mutation has been reported in other cereals. It is not known if these findings are relevant to other cereals, for example wheat.

Two types of debranching enzymes are present in higher plants and are defined on the basis of their substrate specificities, isoamylase type debranching enzymes, and pullulanase type debranching enzymes (Myers et al., 2000). Sugary-1 mutations in maize and rice are associated with deficiency of both debranching enzymes (James et al., 1995, Kubo et al., 1999) however the causal mutation maps to the same location as the isoamylase-type debranching enzyme gene. Representative starch branching enzyme sequences from genes that have been cloned from cereals are listed in Table 1.

TABLE 1

Starch branching enzyme genes characterized from cereals.

| Species | SBE isoform | Type of clone | Accession No. | Reference |
|---|---|---|---|---|
| Wheat | SBEI | cDNA and genomic | AJ237897 (SBEI gene) AF002821 (SBEI pseudogene) AF076680 (SBEI gene) AF076679 (SBEI cDNA) | Baga et al., 1999 Rahman et al., 1997, Rahman et al., 1999 |
|  | SBEI | cDNA | Y12320 | Repellin et al., 1997 |
|  | SBEIIa | cDNA | Y11282 | Nair et al., 1997 |
|  | SBEIIa | cDNA and genomic | AF338432 (cDNA) AF338431 (gene) | Rahman et al., 2001 |
|  | SBEIIb | cDNA and genomic |  | WO 01/62934 |
|  | SBEIIb | cDNA |  | WO 00/15810 |
| Rice | SBEI | cDNA | D10752 | Nakamura and Yamanouchi, 1992 |
|  | SBEI | genomic | D10838 | Kawasaki et al., 1993 |
|  | RBE3 | cDNA | D16201 | Mizuno et al., 1993 |
| Barley | SBEIIa and SBEIIb | cDNA and genomic | AF064563 (SBEIIb gene) AF064561 (SBEIIb cDNA) AF064562 (SBEIIa gene) AF064560 (SBEIIa cDNA) | Sun et al., 1998 |
| Maize | SBEI | cDNA genomic | U17897 AF072724 | Fisher et al., 1996 Kim et al., 1998a |
|  | SBEIIb | cDNA genomic | L08065 AF072725 | Fisher et al., 1993 Kim et al., 1998 |
|  | SBEIIa | cDNA | U65948 | Gao et al., 1997 |

Starch composition, in particular the form called resistant starch which may be associated with high amylose content, has important implications for bowel health, in particular health of the large bowel. The beneficial effects of resistant starch are thought to result from the provision of a nutrient to the large bowel wherein the intestinal microflora are given an energy source which is fermented to form inter alia short chain fatty acids. These short chain fatty acids provide nutrients for the colonocytes, enhance the uptake of certain nutrients across the large bowel and promote physiological activity of the colon. Generally if resistant starches or other dietary fibre are not provided the colon is metabolically relatively inactive.

Whilst chemically or otherwise modified starches can be utilised in foods that provide functionality not normally afforded by unmodified sources, such processing has a tendency to either alter other components of value or carry the perception of being undesirable due to processes involved in modification. Therefore it is preferable to provide sources of constituents that can be used in unmodified form in foods.

Although high amylose maize and barley varieties are known, products from these cereals have disadvantages compared to a very high amylose wheat for products where wheat is the preferred cereal, for example in bread, pasta or noodles. There is therefore an opportunity for a large scale improvement in public health including bowel health and metabolic health through the alteration of wheat starch, which may provide an increase in resistant starch and reduction in glycemic index when provided in the diet.

On passage from the ileum, resistant starches are metabolised by the anaerobic microflora of the caecum and colon which produce the enzymes necessary for polysaccharide hydrolysis and catabolism. Breakdown is effected by bacterial species very similar to those found in the rumen of obligate herbivores and with very similar products: gases, such as carbon dioxide, methane and hydrogen, and short chain fatty acids (SCFA). The principle SCFA formed are acetate, propionate and butyrate in the rough molar proportions 60:20:20. These three acids contribute some 80-90% of total colonic SCFA, the remainder being branched chain and other fatty acids formed from the breakdown of dietary and endogenous protein. Animals fed resistant starch have shown higher colonic SCFA and in some cases increased bacterial mass in the colon. Many of the effects of resistant starch in the colon are probably mediated through SCFA.

The role of dietary fibre in the prevention and management of simple constipation is beyond question. Fibres vary in their effects on bowel function. Cereal brans such as wheat and rice brans that are high in insoluble NSP appear to be most effective in easing problems of laxation through shortening transit time, softening stools through raised water holding, increasing stool volume and weight in the form of bacteria and undigested and non-fermentable material.

Although it is convenient to explain the actions of fibre-rich foods such as wheat bran solely in terms of stool mass, this is not quite correct. However, the increase in faecal bulk in humans eating mixed diets is considerably higher than predicted from their non starch polysaccharide content—the "carbohydrate gap" (Stephen (1991) *Can J Physiol. Pharmacol.* 69:116-20). Starch is thought to fill this gap and contribute to the greater faecal bulk through bacterial proliferation, by providing a fermentation substrate, (both glucose, and certain SCFA) as well as providing physical bulk.

Increases in microbial mass from undigestible carbohydrate fermentation contributes directly to stool bulk, which is a large part of the stool weight. Bacteria are about 80% water and have the ability to resist dehydration, as such they contribute to water-holding in fecal material. The number of bacteria in human feces is approximately $4 \times 10^{11}$-$8 \times 10^{11}$/g dry feces, and makes up to about 50% of fecal solids in subjects on a Western diet. Gas production from colonic fermentation can also have some influence on stool bulk. Trapping of gas can contribute to increased volume and a decrease in fecal transit time.

The metabolic end products of fermentation, namely the gases, SCFA and increased microflora play a pivotal role in the physiological effects of the undigestible carbohydrate in the colon and implications for local effects in the colon and systemic effects. The gases produced from fermentation by strict anaerobic species such as *bacteriodes*, some non-pathogenic species of clostridia and yeasts, anaerobic cocci and some species of lactobacilli are mostly released as flatulence or are absorbed and subsequently lost from the body through the lungs. However, some of the hydrogen and carbon dioxide produced from these microflora may be further metabolized to methane ($CH_4$) by methanogenic bacteria, thus reducing intestinal gas pressure. Of these anaerobic microorganisms, the clostridia, eubacteria and anaerobic cocci are the most gas producing, while the bifidobacteria are the only group of common gut microflora that do not produce any gases.

Because resistant starch is not digested or absorbed, it also serves as a prebiotic for beneficial bacteria, such as bifidobacteria and lactobacilli. Multiplying beneficial bacteria reduce the pH level in the colon, making the environment uninhabitable for potentially harmful bacteria such as *E. coli*, clostridia, *Veillonella* and *Klebsiella*. The proliferation of beneficial bacteria provides significant health effects, including enhanced digestion and improved lactose intolerance, promoting the recycling of compounds such as estrogen, synthesizing vitamins, especially B-group vitamins, producing immune-stimulating compounds, inhibiting the growth of harmful bacteria, reducing the production of toxins and carcinogens, restoring normal intestinal bacteria during antibiotic therapy, and reducing the potential for several pathologies commonly associated with higher numbers of pathogenic intestinal bacteria. These include autoimmune illnesses such as ankylosing spondylitis and rheumatoid arthritis, certain cancers, yeast overgrowth, vaginitis, urinary tract infections, cirrhosis of the liver, food poisoning, antibiotic-associated diarrhea, inflammatory bowel diseases such as ulcerative colitis and Crohn's disease, necrotizing enterocolitis and ileocecitis, food allergy and intolerance, intestinal gas and bloating, and irritable bowel syndrome.

The primary SCFA generated by fermentation are acetate, propionate and butyrate, accounting for 83-95% of the total SCFA concentration in the large intestine, which ranges from about 60-150 µmol/L. The concentrations of these acids are highest where concentrations of microflora are also highest, namely in the cecum and right or transverse colon. Corresponding to these higher acid levels, the pH is also typically lowest in the transverse colon (5.4-5.9) and gradually increases through the distal colon to 6.6-6.9. As the pH is reduced, the colonic environment becomes less favorable for toxin-producing and ill-health promoting microflora, such as *E. coli*, clostridia, and certain yeasts.

The pH range of digesta in the human colon needs to be established but in pigs on high fibre diets it ranges from approximately 6 in the proximal colon to >7 in the distal colon. The pKa of short chain fatty acids is <4.8 so that in the colon they are present largely as anions. SCFA are absorbed in the non-ionic form and are then ionized at intracellular pH to $H^+$ and SCFA which are then exchanged for luminal $Na^+$ and $Cl^-$ respectively. Some of the SCFA are also metabolized to $HCO_3$ which is also exchanged for chloride ions. Therefore SCFA is beneficial in facilitating transporting ions that play an important role in metabolism.

Thus SCFA do not contribute to osmotic load to any great extent and may ameliorate diarrhoea through removal of sodium and water from the colonic lumen. However, because SCFA are present largely as anions, their absorption is relatively slow. For this reason and their presence in faeces, SCFA have been assumed to cause diarrhoea. That view is no longer held and diarrhoea is thought to occur only when the osmotic pressure of simple and complex carbohydrates in the colon raises the fluid volume excessively and bacteria cannot break down the carbohydrate sufficiently rapidly. In fact SCFA may have longer term preventative effects by stimulating growth of colonocytes thereby increasing the capacity of the colon.

Epidemiological data have shown that the level of dietary fibre is inversely related to incidence of bowel cancer and a meta-analysis of a large number of studies showed that fibre was protective in over 50%. It is not possible to discriminate the type of NSP or foods that were effective. A study by Cassidy et al (*British Journal of Cancer* 69; 937-942 (1994)) has shown that starch plays a protective role.

The role of fibre in the maintenance of colonic mucosal integrity is understood imperfectly. Experiments with animal models such as pigs have shown that the weight and thickness of the colon is increased with diets high in fibre—consistent with greater cell growth. The effect is not confined to fibre as Goodlad and Mathers ((1990) *Brit J Nutr.* 64; 569-587) have obtained similar increases in the hindgut of rats fed diets high in resistant starch. Other studies with rats have shown that the increase is probably not due to increased mass of digesta since an inert faecal bulking agent (kaolin) did not stimulate mucosal proliferation. In the same experiments it was shown that colonic infusion of short chain fatty acids enhanced colonocyte proliferation suggesting that they were the trophic agents (Sakata *J Nutr Sci Vitaminol* 1986; 32: 355-362). It is likely that only propionate and butyrate are involved in these effects. Propionate is known to enhance colonic motility possibly through stimulating blood flow (Kvietis and Granger, *Gastroenterol* (1981); 80:962-969). Butyrate is thought to play a most critical role in the cell biology of colonocytes and is preferred over acetate and propionate as their oxidative fuel (Cummings, *Gut* (1981) 22:763-779). Butyrate inhibits the proliferation of malignant cells from the human colon in vitro via inhibition of DNA synthesis an arresting of the cells in the $G_1$ phase. Induction of cell differentiation has also been demonstrated, an observation that is consistent with the fact that when cells differentiate they lose their capacity to proliferate. Butyrate also enhances the capacity of colonic cells to repair DNA damage (Smith, *Carcinogenesis* (1986) 7:423-429). All of these effects require physical presence of the acid and are obtained at butyrate concentrations similar to those found in the colon in vivo. A particular point of interest is that there is evidence that human faecal inocula ferment starch to butyrate (Pilch (ed) Physiological effects and health consequences of dietary fibre. Bethesda Md. USA: FASEB 1987) and such production might explain inconsistencies in epidemiological data where fibre is not always protective but plant foods are beneficial.

Several studies in animal models have shown that supplementation of the diet with fibre protects against tumours induced with chemical carcinogens such as dimethylhydrazine (DMH), azoxymethane (AOM), and 3,2-dimethyl-4-aminobiphenyl (DMAB). Meta-analysis of these studies by the Federation of American Societies for Experimental Biology (FASEB) (Pilch (1987) supra) showed that wheat bran was more effective than pectin or cellulose in reducing lesion formation induced by chemical carcinogens. These data are paradoxical if one considers that soluble NSP might be expected to be fermented to SCFA more than wheat bran. However, rat studies show that wheat bran gives relatively higher concentrations of butyrate in hind-gut digesta than soluble NSP. In addition, wheat bran seems to bind chemical carcinogens and to reduce their colonic concentration and might be doing so in the animal model systems. A protective action of wheat against experimental carcinogenesis cannot be dismissed.

It is believed that butyrate enhances the proliferation of normal cells but may exert antineoplastic effects on susceptible cells and significantly retards the growth of human colon cancer cells in vitro (Kim et al In Malt and Williams (Eds) Colonic carcinogenesis. Lancaster MTP Press, (192); Falk Symposium 31: 317-323). A recent study which has shown that the molar proportion of butyrate is significantly lower in faeces from patients with adenomatous polyps (Weaner et al *Gut* (1988); 29: 1539-1543) is of special interest as it suggests that short chain fatty acid production is abnormal. In a feeding trial in patient with polyposis, a wheat bran supplement appeared to reduce polyp numbers and size (De Cosse et al *J Nat Cancer Inst.* (1989); 81:1290-1297). This is also a very promising study and indicates that insoluble NSP may be protective. Of particular interest is the fact in this study an insoluble NSP (which also enhances lactation) was protective. The situation was soluble NSP and resistant starch is unknown.

It is suggested that lack of luminal SCFAs lead in the short term to muscular atrophy and in the long term to 'nutritional colitis'. This is especially evident in diversion colitis, which develops after complete diversion of the faecal stream and subsides after restoration of colorectal continuity. Irrigation with SCFA for 2-3 weeks has resulted in resolution of inflammation. Ulcerative colitis has also been successfully treated using butyrate enemas. (Scheppach et al (1992) *Gasteroenterology;* 103:51-56. Generally anti-inflammatory measures, such as the use of anti inflammatory drugs, do have side effects and in particular where large doses are used to overcome the natural degradation of those drugs in the small intestine before they reach the colon. The use of SCFA on the other hand is seen as particularly beneficial because they are naturally occurring and replace the use of anti-inflammatory drugs such as NSAIDS, corticosteroids and other anti inflammatory drugs.

General

Those skilled in the art will be aware that the invention described herein is subject to variations and modifications other than those specifically described. It is to be understood that the invention described herein includes all such variations and modifications. The invention also includes all such steps, features, compositions and compounds referred to or indicated in this specification, individually or collectively, and any and all combinations of any two or more of said steps or features.

Throughout this specification, unless the context requires otherwise the word "comprise", and variations such as "comprises" and "comprising", will be understood to imply the inclusion of a stated integer or step or group of integers or steps but not the exclusion of any other integer or step or group of integers or steps. The present invention is not to be limited in scope by the specific embodiments described herein, which are intended for the purposes of exemplification only. Functionally-equivalent products, compositions and methods are clearly within the scope of the invention, as described herein.

Bibliographic details of the publications referred to by the inventors in this specification are collected at the end of the description. The references mentioned herein are hereby incorporated by reference in their entirety. Reference herein to prior art, including any one or more prior art documents, is not to be taken as an acknowledgment, or suggestion, that said prior art is common general knowledge in Australia or forms a part of the common general knowledge in Australia.

As used herein, the term "derived from" shall be taken to indicate that a particular integer or group of integers has originated from the species specified, but has not necessarily been obtained directly from the specified source.

The designation of nucleotide residues referred to herein are those recommended by the IUPAC-IUB Biochemical Nomenclature Commission, wherein A represents Adenine, C represents Cytosine, G represents Guanine, T represents Thymidine.

SUMMARY OF THE INVENTION

This invention results from a finding that products made from the grain obtained from modified wheat plants comprise sufficient resistant starch and/or lowered glycemic index to provide a health benefit when ingested at levels which can be incorporated into food or beverage products or otherwise delivered to the gastrointestinal tract of a mammal. The health benefit may relate to bowel health or metabolic health or both.

In a first aspect the invention provides a method of improving one or more indicators of bowel health or metabolic health in a mammalian animal, comprising the step of delivering to the gastrointestinal tract of said animal an effective amount of an altered wheat starch in the form of or derived from the grain of a wheat plant, wherein the proportion of amylose in the starch of the grain is at least 30% and/or wherein said grain comprises a reduced level of SBEIIa enzyme activity relative to wild-type grain. The mammalian animal may be non-ruminant or monogastric, for example a human.

In an embodiment, the grain comprises a genetic variation which leads to a reduction in the level of SBEIIa gene expression, SBEIIa enzyme activity in the endosperm or both relative to wild-type grain, which genetic variation comprises a mutation of an SBEIIa gene or an introduced nucleic acid which encodes an inhibitor of SBEIIa gene expression. The altered wheat starch may comprise at least 2%, at least 2.5% or at least 3% resistant starch.

The wheat plant may have a reduced level of SBEIIa or SBEIIa and SBEIIb enzyme activities relative to wild-type grain, and the proportion of amylose in the starch of the grain may be at least 30%, more preferably at least 35%, at least 40%, at least 45%, at least 50% or at least 55%. In an embodiment, the grain comprises a reduced level of SBEIIb protein, enzyme activity or both relative to wild-type grain. The wheat plant may additionally comprise a reduced level of SBEI protein, enzyme activity or both relative to wild-type grain. The wheat plant may additionally comprise an altered level of an enzyme relative to wild-type gain, wherein said enzyme is ADP glucose pyrophosphorylase, GBSS, SSI, SSII, SSIII, phosphorylase, a debranching enzyme of an isoamylase type, or a debranching enzyme of a pullulanase type, or any combination of these. The altered level may be an increased level or a decreased level.

The amylopectin of the grain may be characterised in comprising a reduced proportion of the 4-12 dp chain length fraction relative to the amylopectin of wild-type grain, as measured after isoamylase debranching of the amylopectin.

The wheat plant or altered wheat starch may be any one or more of the forms described herein. It is thought that at least some of the altered wheat starch is a resistant starch. The altered wheat starch may be blended with unaltered wheat starch in the form of grain, flour, wholemeal, purified starch or other forms, or similarly with non-wheat starch or other food ingredients.

At least 10 g of altered wheat starch may be provided to a human per day although the levels are preferably greater than 15, 20, 25, 30, 35, 40, 45, 50 or 55 g per day.

However the invention may also encompass levels of delivery as low as at least 1, 2 or 5 grams per day, or levels of delivery higher such as at least 60, 70, 80, or 100 grams per day.

The altered wheat starch is preferably delivered to the mammal, particularly humans, orally. The starch may be delivered in the form of whole grain or milled, ground, pearled, rolled, kibbled, par-boiled or cracked grain, or as isolated starch or starch granules. Alternatively the starch may be delivered as part of a food or beverage product which may be as a condiment. In a further alternative, the starch may be delivered in the form of a pharmaceutical preparation suitable for oral ingestion. It will be understood that whilst oral ingestion is preferred, the invention also encompasses other means of delivery of the altered wheat starch to the colon.

It may be advantageous also to modify the altered starch chemically. Chemical modification may include etherification, esterification, acidification, or reducing enzyme susceptibility by, for example, acid or enzyme thinning and cross bonding using difunctional reagents. Physical modification may include heating and crystallization. Such modifications may increase the level of resistant starches.

The indicators of improved bowel health may comprise, but are not necessarily limited to:
 i) decreased pH of the bowel contents,
 ii) increased total SCFA concentration or total SCFA amount in the bowel contents,
 iii) increased concentration or amount of one or more SCFAs in the bowel contents,
 iv) increased fecal bulk,
 v) increase in total water volume of bowel or faeces, without diarrhea,
 vi) improved laxation,
 vii) increase in number or activity of one or more species of probiotic bacteria,
 viii) increase in fecal bile acid excretion,
 ix) reduced urinary levels of putrefactive products,
 x) reduced fecal levels of putrefactive products,
 xi) increased proliferation of normal colonocytes,
 xii) reduced inflammation in the bowel of individuals with inflamed bowel,
 xiii) reduced fecal or large bowel levels of any one of urea, creatinine and phosphate in uremic patients, or
 xiv) any combination of the above.

The pH of the bowel contents may be reduced by at least 0.1 pH unit, preferably at least 0.2 pH units. The one or more SCFA may be selected from formate, acetate, propionate, butyrate, succinate or branched forms thereof, but is preferably one of acetate, proprionate and butyrate and more preferably butyrate.

Among the probiotic bacteria, bifidobacteria species are the most prominent. Lactic acid bacteria are similarly included such as, for example, *Lactobacillus bulgaricus, Lactobacillus acidophilus, Lactobacillus casei, Lactobacillus plantarum*, or *Streptococcus laecium* or *Streptococcus thermophilus*.

The indicators of improved metabolic health may comprise, but are not necessarily limited to:
 i) stabilisation of post-prandial glucose fluctuation,
 ii) improved (lowered) glycemic response, iii) reduced pro-prandial plasma insulin concentration,
iv) improved blood lipid profile,
v) lowering of plasma LDL cholesterol,
vi) reduced plasma levels of one or more of urea, creatinine and phosphate in uremic patients,
vii) an improvement in a dysglucaemic response, or
viii) any combination of the above.

The invention includes a change of at least 1%, at least 2%, at least 5%, at least 10%, at least 15%, at least 20%, at least 25%, at least 30%, at least 35%, at least 40%, at least 45% or at least 50% in any one or more of the bowel health or metabolic health indicators or both.

The method may be particularly beneficial in treating a human having any one or more of the conditions: constipation, diarrhea, irritable bowel syndrome, Crohn's disease, colorectal cancer, diverticular disease, ulcerative colitis, high blood LDL cholesterol, uremia resulting from kidney disease or other diseases, or diabetes. Alternatively, the method provides for the prevention or reduced risk in a human of any one or more of these conditions.

The decrease in the bowel contents is preferably at least 0.1 pH units, but may be at least 0.2, at least 0.3, at least 0.4 or at least 0.5 pH units. The change in pH may be measured in faeces, or internally, for example in the caecum, in the proximal colon or the distal colon.

The Short Chain Fatty Acids (SCFA), the concentration or total amount of which may vary, can be any one or more of formates, acetate, propionate, butyrate, succinate or branched forms thereof. Preferably the SCFA is one or more of acetate, propionate or butyrate, and most preferably is butyrate. Alternatively the change in concentration or total amount is a pooled value of total SCFA or a selected group of one or more of them. The concentration change may be as measured in faeces, or internally, which may be in the caecum, the proximal colon, the distal colon or any combination of these. The total amount may increase while the concentration remains the same or even increases if the bowel contents increase in volume over time. The SCFA content is thus a measure of the total amount of one or more SCFA in either the caecum, proximal colon, or distal colon or two or more of these combined. The concentrations or amounts might exhibit an increase of at least 5%, at least 10%, at least 15%, at least 20% or at least 50%.

Fecal bulk increases principally as a result of greater numbers of bacteria that are supported in the caecum and colon. The volumes may be measured by an increase in quantity of feces, or may be measured in situ by estimating the volume of cecal, proximal colon, or distal colon contents, separately or as a combination of two of these or all three of these. The increase in volume might be at least 5%, at least 10%, at least 15%, at least 20% or at least 50%.

The water volume of the bowel or faeces increases as a result principally of increased number of bacteria. The water content can be measured by comparing the wet weight of the faeces or bowel contents with dry weight after drying, the volume of water can be calculated from this decrease in weight. This increase in water volume might be in cecal, proximal colon, or distal colon contents, separately or as a combination or two of these or all three of these. The increase in volume might be at least 5%, at least 10%, at least 15%, at least 20% or at least 50%.

Laxation relates to the passage of solids from the bowel, and entails measuring defecation in a quantitative and/or qualitative manner. Frequency of defecation is one aspect of laxation and thus the frequency of defecation might increase at least 20%, at least 30%, at least 50%, or at least 100%. One qualitative measure relates to hardness of stools, whereby passage is easier, in contrast to constipation, but where stools are not so soft or loose as to constitute diarrhea. This measure might be considered related to the water volume of the feces and these may increase by 5%, at least 10%, at least 15%, at least 20% or at least 50%.

The probiotic bacteria are generally considered those that might be good for bowel health, being non infectious and producing beneficial metabolites as a result of their fermentation activities. Among the probiotic bacteria, bifidobacterial species are the most prominent. Lactic acid bacteria are similarly included such as, for example, *Lactobacillus bulgaricus, Lactobacillus acidophilus, Lactobacillus casei, Lactobacillus plantarum, Streptococcus faecium* or *Streptococcus thermophilus*. Numbers of individual species or genera might individually or collective increase by at least 20%, at least 25% or at least 50%. There may also be a reduction in the number of bacterial species that have a potentially adverse effect on the large bowel. Many such species are unable or less able to utilise resistant starch for energy compared to the probiotic organisms. Examples of such adverse bacteria include some *Clostridia, Veillonella* and *Klebsiella*.

Preferably the resistant starch enhances fecal bile acid excretion. Increased fecal bile acid excretion induces the liver to produce more bile acids, utilizing cholesterol as a substrate in the production of the bile acids. The liver can obtain cholesterol for the synthesis of bile acids from the blood, lowering blood cholesterol concentrations. Alternatively this may simply be used as a general marker of bowel activity, and clearance of bile. The build up of bile acids is also thought to have at least a correlation to bowel pathogensis. The increase might be by at least 5%, at least 10%, at least 15%, at least 20% or at least 50%. Similar decreases of plasma LDL cholesterol levels may also be exhibited.

Preferably the resistant starch also reduces urinary and fecal levels of putrefactive products or indicators of putrefactive products. This is indicative of a reduced level of fermentation by putrefying bacteria in the colon or caecum. Additionally these may be indicative of reduced small intestinal overgrowth. The level of these compounds can measured for, by example using HPLC or other techniques. Many of these compounds are metabolic products or biproducts of protein or amino acid degradation. Compounds may be urea, ammonia and other waste nitrogen products or sulfides and sulfur containing compounds including hydrogen sulfide gas. Specific compounds that may be tested include but are not limited to phenol, indole, skatole, and ammonia, p-cresol, 4-ethylphenol, urea, ketones, and amines. The decrease may be by at least 5%, at least 10%, at least 15%, at least 20% or at least 50%.

The reduction of inflammation of the bowel might be by at least 10%, at least 20% or at least 50%.

In kidney failure there is a decrease in the glomerular filtration rate and the kidneys are unable to maintain homeostasis of the blood. Homeostatic balance of water, sodium, potassium, calcium and other salts is no longer possible and nitrogenous wastes are not excreted. Retention of water causes edema and as the concentration of hydrogen ions increases, acidosis develops. Nitrogenous wastes accumulate and a condition referred to as uremia develops in the blood and tissue. Examples of uremic toxins include, but are not limited to, ammonia, urea, creatinine, phenols, indoles, and middle molecular weight molecules. There may also be an accumulation of phosphate.

Reduced kidney function is to some extent compensated for by the intestinal wall which also acts as a semipermeable membrane allowing small molecules to pass from the intestinal tract into the bloodstream and preventing larger molecules from entering the circulation. Nitrogenous wastes such as urea, creatinine and uric acid, along with several other small and medium molecular weight compounds, flow into the intestine and equilibrate across the intestinal epithelium. The present invention enhances the capacity of the bowel and thus enhances removal of waste products across the bowel. This enhancement of bowel function thus has a second very important function in uremic patients over and above benefits that are provided for normal individuals. The capacity of enhanced function can be measured by reduced levels of waste compounds in urine associated with uremic patients such as, for example, urea, creatinine and phosphate. These may be reduced in level by at least 5%, at least 10%, at least 15%, at least 20% or at least 50%. Plasma levels of these compounds, reduced to the same extent, may also be exhibited in preferred embodiments of the invention in uremic patients.

After ingestion of food there is generally an initial excursion in blood sugar levels, the rate of increase depending on the food ingested. Over a period of 1-2 hours in normal individuals, the blood sugar level is brought down to a generally elevated level through production and function of insulin. However, it is desirable to have a lower rate of increase and lower peak level in the blood sugar, with the increase prolonged over an extended period, not only in normal individuals but even more so in individuals with diabetes or Insulin deficiency (ID). A prolonged absorption of carbohydate from the bowel is also desirable, particularly in sufferers of diabetes, to counter the hypoglycaemia that is often encountered, particularly at night time. Because it is relatively resistant to digestion, the modified starch or wheat product of the present invention enhances glycemic control in healthy individuals and particularly in the diabetic patient. An advantage of the present invention is therefore that it provides a composition having effectively low carbohydrate content and starch that is more slowly digested.

Slower glucose absorption slows insulin release and reduces excessive insulin responses in response to rising blood glucose levels after a meal. This benefits pancreatic secretion of insulin by reducing both the glucose load and rate of glucose load over the initial phases of glucose detection, absorption and metabolism by the body. Reduced rates of glucose loading therefore reduces the stress on beta cells normally associated with the insulin response to rising glucose. Moreover, slower or moderated glucose absorption permits more time for insulin to stimulate normal sugar metabolic routes. Consequently, insulin dependent mechanisms have more time to prepare for the arrival of sugars from the intestine. This moderation of glucose absorption improves short-term insulin modulation in the liver, muscle, and adipose tissue.

Blood glucose measurements may be made by any number of methods. The timing of any blood glucose test may be material, and the present invention contemplates determining the fasting blood glucose level and especially the post-prandial blood glucose level. In general, the desirable fasting glucose level (pre-prandial) is 80 to 120 mg/dL, and a non-diabetic has a pre-prandial glucose level of less than 110 mg/dL. The desirable post-prandial level is 100 to 140 mg/dL, and a non-diabetic has a bedtime glucose level of less than 120 mg/dL. Under the American Diabetes Clinical Practice Recommendations, additional action is recommended if the fasting blood glucose level is greater than 140 mg/dL or the post-prandial glucose level is greater than 160 mg/dL.

In a preferred form, the post prandial glucose level after ingestion of food according to the present invention is less than about 160 mg/dL, more preferably less than about 155, 150, 145, 140, or 130 mg/dL.

The blood glucose response (peak level) resulting when the modified wheat or starch of this invention is utilized is preferably no more than 50%, more preferably no more than 12% compared to when glucose or dextrose is used, while the blood glucose response (area under the concentration/time curve) is no more than 75%, preferably no more than 30%, even more preferably, no more than 10% of the blood glucose response resulting when dextrose or glucose is used. The blood glucose response (peak) is defined as the rise in blood glucose concentration from the pre-feeding concentration to the peak concentration (usually occurring within one hour after feeding), expressed as a percentage of the rise observed when an equivalent mass of glucose or dextrose is fed.

Similarly post prandial plasma insulin levels may be reduced by at least 5%, at least 10%, at least 15%, at least 20% or at least 50% compared to when unmodified wheat or starch is used.

The profile of lipids in the blood may be reflective of disorders of lipid synthesis and transport in the individual. Abnormal patterns of blood lipid profile, also known a dys-lipidemias, may be characterized by one or more of the following: elevated levels of total and low density lipoprotein (LDL)-cholesterol, elevated levels of triglycerides (TG), low levels of high density lipoprotein (HDL)-cholesterol, a high LDL/HDL ratio, or elevated levels of WA (free fatty acids). An imbalance of lipids may also be exhibited in individuals that suffer from diabetes or have syndrome X. Generally it is desired to reduce total plasma cholesterol (C), LDL-C and very low density lipoprotein triglycerides (VLDL-triglycerides) and TG, elevated levels of which are associated with health risks, while raising serum levels of HDL-C which is considered a "healthy" lipoprotein. The invention in a preferred form exhibits a variation of blood levels of these by at least 5%, at least 10%, at least 15%, at least 20% or at least 25%.

Whilst the invention may be particularly useful in the treatment or prophylaxis of humans, it is to be understood that the invention is also applicable to non-human animals including but not limited to agricultural animals such as cows, sheep, pigs and the like, domestic animals such as dogs or cats, laboratory animals such as rabbits or rodents such as mice, rats, hamsters, or animals that might be used for sport such as horses. The method may be particularly applicable to non-ruminant mammals or animals such as mono-gastric mammals. The invention may also be applicable to other agricultural animals for example poultry including, for example, chicken, geese, ducks, turkeys, or quails, or fish.

The method of treating the animal, particularly humans, may comprise the step of administering altered wheat grain, flour or starch to the animal, in one or more doses, in an amount and for a period of time whereby the level of the one or more of the bowel health or metabolic indicators improves. The indicator may change relative to consumption of non-altered wheat starch or wheat or product thereof, within a time period of hours, as in the case of some of the indicators such as pH, elevation of levels of SCFA, post-prandial glucose fluctuation, or it may take days such as in the case of increase in fecal bulk or improved laxation, or perhaps longer in the order of weeks or months such as in the case where the butyrate enhanced proliferation of normal colonocytes is measured. It may be desirable that administration of the altered starch or wheat or wheat product be lifelong. However, there are good prospects for compliance by the individual being treated given the relative ease with which the altered starch can be administered.

Dosages may vary depending on the condition being treated or prevented but are envisaged for humans as being at least 1 g of altered starch per day, more preferably at least 2 g per day, preferably at least 10 or at least 20 g per day. Administration of greater than about 100 grams per day may require considerable volumes of delivery and reduce compliance. Most preferably the dosage for a human is between 5 and 60 g of altered starch per day, or for adults between 5 and 100 g per day.

The altered wheat starch of the present invention is able to be readily incorporated into food or beverage products at levels typically ingested in normal human diets. Intake of at least about 10 g per day is thought to provide a measurable benefit, although more preferably the intakes are at least about 20-30 grams of the altered wheat starch per day. Typically, humans have daily intakes of at least 100 to 200 g of starchy food products such as bread or pasta, which means that levels of altered starch in the food product of at least 5 to 10% will typically provide a beneficial effect. It is proposed that levels of less than that, for example, as low as 1% will also give a beneficial effect which may or may not be immediately measurable.

Thus a second aspect of the invention provides a food, beverage or pharmaceutical preparation comprising at least 1% (w/w) altered wheat starch in the form of or derived from the grain of a wheat plant, wherein the proportion of amylose in the starch of the grain is at least 30% and/or wherein said grain comprises a reduced level of SBEIIa enzyme activity relative to wild-type grain. In an embodiment, the altered wheat starch comprises at least 2% (w/w) resistant starch, preferably at least 3%, at least 4%, at least 5%, at least 6% or at least 10% resistant starch, but the level may be higher perhaps at least 20%, 30%, 40% or 50%. In another embodiment, the proportion of amylose in the altered wheat starch derived from the grain is at least 30% (w/w), preferably at least 35%, at least 40%, at least 45%, at least 50%, at least 65%, at least 70%, at least 75% or at least 80%.

In an embodiment, the food or beverage product comprises an ingredient comprising the altered starch, wherein the ingredient is flour, wholemeal, semolina or substantially purified starch derived from the grain. In a further embodiment, the food or beverage product comprises flour, wholemeal, semolina or starch derived from another source.

The food, beverage or pharmaceutical preparation may comprise at least 1% (w/w) resistant wheat starch derived from the grain of a wheat plant wherein the proportion of amylose in the starch of the grain is at least 50%.

The food, beverage or pharmaceutical preparation may comprise at least 1% altered or resistant wheat starch in the form of or derived from the grain of a wheat plant, wherein the proportion of amylose in the starch of the grain is at least 30% and/or wherein said grain comprises a reduced level of SBEIIa enzyme activity relative to wild-type grain.

The wheat plant may have a reduced level of SBEIIa or SBEIIa and SBEIIb enzyme activity relative to wild type grain and the proportion of amylose in the starch of the grain may be at least 30% and more preferably at least about 35%, at least 40%, at least 45%, at least 50% or at least 55%. In an embodiment, the grain comprises a reduced level of SBEIIb protein, enzyme activity or both relative to wild-type grain. The wheat plant may additionally comprise a reduced level of SBEI protein, enzyme activity or both relative to wild-type grain. The wheat plant may additionally comprise an altered level of one or more enzymes relative to wild-type grain, wherein said enzyme may be ADP glucose pyrophosphorylase, GBSS, SSI, SSIIa, SSIIb, SSIII, phosphorylase, a debranching enzyme of an isoamylase type, or a debranching enzyme of a pullulanase type. The altered level may be an increased level or a decreased level.

The amylopectin of the grain may have a reduced proportion of the 4-12 dp chain length fraction relative to the amylopectin of wild-type grain, as measured after isoamylase debranching of the amylopectin.

The food or beverage product may have at least 2% (w/w), preferably at least 3%, at least 4%, at least 5%, at least 6%, at least 8%, at least 10%, at least 15%, at least 20%, at least 25%, at least 30%, at least 35%, at least 40% or at least 50% altered or resistant wheat starch.

It is thought that heating or baking of the food product is preferred because this results in increased retrogradation of the starch on cooling and therefore may enhance the level of resistant starch. In an embodiment, the starch in the form of grain, flour, wholemeal or other form, or the food, beverage or pharmaceutical preparation containing the starch is heated to at least 60° C. for at least ten minutes one or more times, which may be prior to or during preparation of the food, beverage or pharmaceutical preparation, with subsequent cooling, to provide greater disruption of the starch granules and greater crystallization. The starch, food or beverage product is preferably heated to higher temperatures, preferably at least about 70° C., at least 80° C., at least 90° C., at least 95° C. or at least 100° C., perhaps also in the presence of elevated pressures.

The altered starch may be directly eaten as a powder or as an edible composition comprising resistant starch and water, resistant starch and food material, resistant starch in foods, resistant starch in beverages or resistant starch and seasonings. The altered starch may be incorporated into fat or oil products such as margarine or shortening, salad dressing, egg products such as mayonnaise, dairy products such as milk, yogurt or cheese, cereal products such as corn or wheat flour, fruit juices, other foods or food materials, or the altered starch may be processed into beverages or foods such as bread, cake, biscuits, breakfast cereals, pasta, noodles or sauces. Other products include prepacked mixes such as, for example, pancake or cake mixes. Alternatively, the altered wheat starch may be provided as a pharmaceutical preparation preferably for orally administration such as, for example, tablets, capsules, granules, powders, syrups or suspensions. Alternatively, these may be parenterally administered.

When incorporated into bread or other foods, the altered wheat starch may be in the form of grain, flour, wholemeal or purified starch. It may be used as a partial replacement for non-altered wheat forms and may replace at least 5% (w/w), at least 10%, at least 15%, at least 20%, at least 25%, at least 30%, at least 35%, at least 40%, at least 45%, at least 50% or more of the non-altered form using in conventional formulations. For breads, the replacement is preferably in the range of 10% to 100% or 50% to 100%. This may assist to minimise the impact on the baking process while providing for an adequate delivery of modified wheat starch on ingestion of a typical daily intake of 100 to 200 grams. Alternatively the flour incorporated into the bread may be derived solely from the modified wheat.

The food or beverage or pharmaceutical preparation may be packaged ready for sale or in bulk form.

The invention also provides methods of preparing the food, beverage or pharmaceutical preparation of the invention, and recipes or instructions for preparing such foods or beverages. The methods or recipes or instructions may include the step of mixing altered wheat starch derived from the grain of a wheat plant with another ingredient, wherein the portion of the amylose in the starch of the grain is at least 30%. The methods or recipes or instructions may include the step of heating or baking the altered starch ingredient or the product to at least 60° C. for at least ten minutes one or more times, or preferably to at least 100° C., at least 120° C., at least 140° C., at least 180° C., at least 200° C. or at least 220° C., before or after the mixing step. The method may include the step of packaging the product so that it is ready for sale.

BRIEF DESCRIPTION OF THE DRAWINGS

FIG. 1. Sequence of the Starch Branching Enzyme IIa gene (wSBE II-D1) [SEQ ID No. 1] from *A. tauschii*, corresponding to the D genome SBEIIa gene of hexaploid wheat (*T. aestivum*).

FIG. 2. Partial wheat SBEIIb gene sequence (wbe2b genomic) [SEQ ID No. 2] from *T. aestivum*.

FIG. 3. Schematic of duplex-RNA constructs. A. The order of the gene elements used were promoter, SBEIIa or SBEIIb gene sequence (exons 1, 2 and 3) in sense orientation, intron (intron 3), SBEIIa or SBEIIb gene sequence (exons 1, 2, 3 and 4) in antisense orientation, and transcription terminator/polyadenylation sequence. B. The transcript of the ds-SBEIIa and ds-SBEIIb genes forms a "hairpin" RNA structure with a double-stranded region formed by hybridization between the sense and antisense sequences. The intron sequence bordered by the GT and AG nucleotides is spliced out.

FIG. 9. Nucleotide sequence of a cDNA encoding wheat SBEIIb [SEQ ID NO. 3].

DETAILED DESCRIPTION OF THE INVENTION

Figure 4:
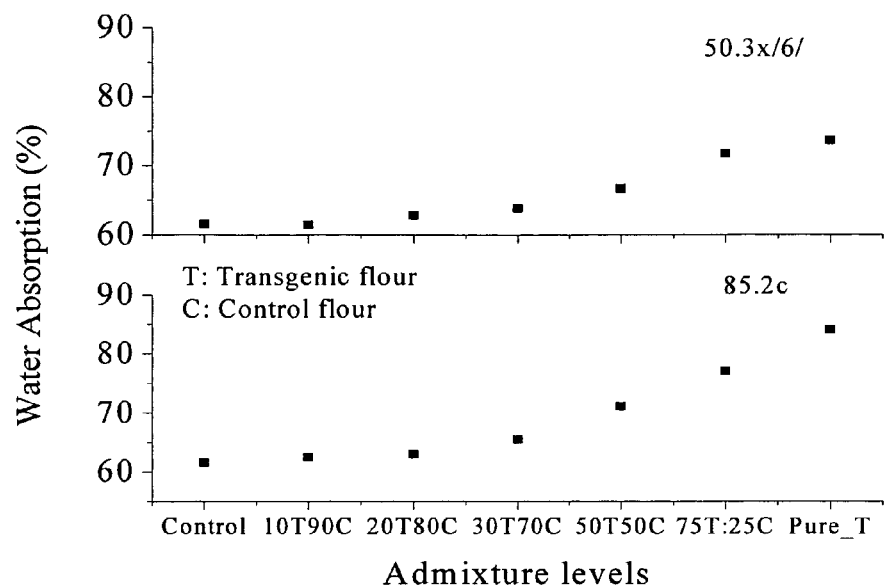
FIG. 4. Water absorption parameters for blends of high amylose flour from transgenic (T) and control (C) varieties, mixed in the ratios 0:100, 10:90, 20:80, 30:70, 50:50, 75:25, 100:0, as measured by Micro Z-arm mixing. Transgenic varieties used were 50.3x/6/(60.1% amylose) and 85.2c (81% amylose).

The invention is based on the finding that the production of modified wheat and its incorporation into the diet of animals, particularly mammals, results in the improvement of bowel health as measured by several indicators. Furthermore, food products made with the modified wheat showed attributes such as increased levels of resistant starch (RS) and lower glycemic index (GI) and therefore consumption of the food products also provides improved metabolic health. The wheat plant is modified in starch biosynthesis, in particular to elevate the proportion of amylose in the starch of the grain.

A wheat plant is defined herein as any plant of a species of the genus *Triticum*, which species is commercially cultivated, including, for example, *Triticum aestivum* L. ssp. *aestivum* (common or bread wheat), other subspecies of *Triticum aestivum*, *Triticum turgidum* L. ssp. *durum* (durum wheat, also known as macaroni or hard wheat), *Triticum monococcum* L. ssp. *monococcum* (cultivated einkorn or small spelt), *Triticum timopheevi* ssp. *timopheevi*, *Triticum turgigum* L. ssp. *dicoccon* (cultivated emmer), and other subspecies of *Triticum turgidum* (Feldman). The wheat may be hexaploid wheat having an AABBDD type genome, or tetraploid wheat having an AABB type genome. Since genetic variation in wheat according to the invention can be transferred to certain related species including rye and barley by hybridization, the invention also includes use of the hybrid species thus formed, including triticale that is a hybrid between bread wheat and rye. In a particular embodiment, the wheat plant is of the species *Triticum aestivum*, and preferably of the subspecies *aestivum*. Alternatively, since mutations or transgenes can be readily transferred from *Triticum aestivum* to durum wheat, in another embodiment the wheat is *Triticum turgidum* L. ssp. *durum*.

The wheat plant is modified according to the invention so that it produces altered starch in its grain. "Starch" is defined herein as polysaccharide made up essentially of α-glucopyranose units. Starch is the major storage carbohydrate in wheat, is synthesized in the amyloplasts and formed and stored in granules in the developing grain. It includes amylose, an essentially linear (<0.1% branchpoints) α-1,4-D-glucopyranose polymer and amylopectin, which has short chains of α-D-glucopyranose units primarily linked by α-1,4 bonds with α-1,6 linked branches. Wheat starch from wild-type plants comprises up to about 20%-30% of amylose and about 70%-80% of amylopectin. A further significant difference between amylose and amylopectin is in the molecular weight of the polymers. Amylose has a helical conformation with a molecular weight of $10^4$-$10^6$ daltons while amylopectin has a molecular weight of about $10^7$ to $10^8$ daltons. Recent studies have shown that up to about 0.1% of α-1,6-glycosidic branching sites may occur in amylose, therefore it is described as "essentially linear". "Amylose" is defined herein as including essentially linear molecules of α-1,4 linked glucosidic (glucopyranose) units and amylose-like long-chain amylopectin (sometimes referred to as "intermediate material" or "amylose-like amylopectin", Takeda et al., 1993b; Fergason, 1994). The proportion of amylose in the starch as defined herein is on a weight/weight (w/w) basis, i.e. the weight of amylose as a percentage of the weight of total starch from the grain. Amylose content may be determined by any of the methods known in the art including size exclusion HPLC, for example in 90% (w/v) DMSO, concanavalin A methods (Megazyme Int, Ireland), or preferably by iodometric methods, for example as described in Example 1. The HPLC method may involve debranching of the starch (Batey and Curtin, 1996) or not involve debranching. From the grain weight and amylose content, the amount of amylose deposited per grain can be calculated and compared for modified and control lines.

The modification of the wheat plant according to the invention includes one or more alterations in the activity or amount of starch biosynthetic enzymes in the endosperm. "Endosperm" as used herein has the normal meaning known in the art, being the tissue that is the primary site of starch synthesis and deposition in the developing grain, and the primary product of milling of mature grain to remove the aleurone and germ. In one embodiment, the alteration comprises a reduction in the amount and/or activity of starch branching enzyme IIa (SBEIIa) in the wheat endosperm, which results in an increased proportion of amylose in the starch of the mature wheat grain. In another embodiment, the modification comprises reduction in SBEIIb as well as SBEIIa activity. Mutation in the genes encoding these two activities in wheat is aided by the surprising finding that SBEIIa and SBEIIb are closely linked in wheat, in contrast to non-linkage in maize and rice. In a further embodiment, the modification comprises reduction in all three of SBEIIa, SBEIIb and SBEI. Other starch biosynthesis enzymes that may be altered in combination with any of the above include starch synthase I (SSI), starch synthase II (SSII), starch synthase III (SSIII), phosphorylase or starch debranching enzymes such as isoamylase or pullulanase. The alterations may be, for example, increased activity, decreased activity, altered localization or timing of activity. When alterations in some of these enzymes are combined, characteristics of the starch other than the relative amylose content may also be altered. In an embodiment, the modified wheat comprises alterations in the activity of multiple starch biosynthesis enzymes in wheat endosperm, preferably including a reduction in the activity of SBEIIa such that the proportion of amylose in the starch of the grain is increased. In a further embodiment, the activity of one or more starch biosynthesis enzymes is altered in the plant in tissues other than endosperm, for example the activity of SBEI or SBEII may be increased in leaves to compensate for some loss of activity caused by a transgene encoding an SBEIIa-inhibitory molecule intended primarily for expression in the endosperm. The alteration in an enzyme activity may be an increase or reduction in amount or an alteration in the timing of expression. Starch synthesis may be further improved by the overexpression of one or more starch biosynthetic enzymes in combination with a reduction in SBEIIa. Genes encoding such enzymes may be from any of a variety of sources, for example from bacterial or other sources other than wheat, and may be modified to alter the catalytic properties, for example alteration of the temperature dependence of the enzymes (for example, see WO94/09144).

The high amylose phenotype may be achieved by partial or full inhibition of the expression of the SBEIIa gene, or the SBEIIa and SBEIIb genes. A "high amylose" phenotype or "high amylose level in the starch of the grain" or the like as used herein refers to total starch obtained from the grain having at least 30% amylose. The extent to which the gene or genes are inhibited will in some degree determine the characteristics of the starch made in the wheat grain. Any of a range of gel electrophoresis techniques carried out on the proteins extracted from the modified wheat endosperm will reveal the nature and extent of modification to the SBEIIa and/or SBEIIb activity. Modification may occur as a reduction in SBEIIa and/or SBEIIb activity, complete abolition of enzyme activity, or an alteration in the distribution of the SBEIIa, SBEIIb or other enzymes within the endosperm. For example, SBEIIa, SBEIIb or other activity may be reduced by affecting the distribution of the enzymes within the endosperm, such as reducing the level of enzyme that is starch granule-bound. Such a pattern has been observed for SBEIIa in maize that is mutant at the dull1 locus. To carry out these tests, starch may be extracted from the wheat endosperm and the proteins therein analyzed, for example as outlined in Rahman et al, 1995. Techniques well known in the art such as SDS-PAGE and immunoblotting are carried out on the soluble and the starch granule fractions and the results used to identify the plants or grain where modifications have occurred to the SBEIIa, SBEIIb or other enzymes.

Alteration of the starch biosynthesis enzyme activities may be achieved by the introduction of one or more genetic variations into the wheat plant. That is, the genetic variations lead, directly or indirectly, to the alteration in enzyme activity in the endosperm during grain development and consequently to the starch modifications described herein. A reduction in the level of SBEIIa or other enzyme activity may be accomplished by a reduction in the expression of one or more genes encoding the enzymes, which may be achieved by mutation, a combination of mutations, or the introduction of one or more nucleic acids, for example a transgene which encodes an inhibitory molecule. Examples of inhibitory molecules include antisense, co-suppression, ribozyme or duplex RNA molecules.

As used herein, the terms "altering", "increasing", "increased", "reducing", "reduced", "inhibited" or the like are considered relative terms, i.e. in comparison with the wild-type or unaltered state. The "level of a protein" refers to the amount of a particular protein, for example SBEIIa, which may be measured by any means known in the art such as, for example, Western blot analysis or other immunological means. The "level of an enzyme activity" refers to the amount of a particular enzyme measured in an enzyme assay. It would be appreciated that the level of activity of an enzyme might be altered in a mutant if a more or less active protein is produced, but not the expression level (amount) of the protein itself. Conversely, the amount of protein might be altered but the activity (per unit protein) remain the same. Reductions in both amount and activity are also possible such as, for example, when the expression of a gene encoding the enzyme is reduced transcriptionally or post-transcriptionally. In certain embodiments, the reduction in the level of protein or activity is by at least 40% or by at least 60% compared to the level of protein or activity in the endosperm of unmodified wheat, or by at least 75%, at least 90% or at least 95%. The reduction in the level of the protein or enzyme activity or gene expression may occur at any stage in the development of the grain, particularly during the grain filling stage while starch is being synthesized in the developing endosperm, or at all stages of grain development through to maturity. In a further embodiment, the level of SBEIIa or other enzyme is reduced in the endosperm by at least 50% compared to the wild-type. The term "wild-type" as used herein has its normal meaning in the field of genetics and includes wheat cultivars or genotypes which are not modified as taught herein.

The amount or the activity of enzymes such as SBEIIa in wheat endosperm may be measured using any method known in the art such as, for example, by immunodetection methods, Western blotting or ELISA assays, or the level of its corresponding mRNA may measured by methods such as Northern blot hybridization analysis or reverse transcription polymerase chain reaction (RT-PCR). A wheat plant or grain having an altered level of a particular protein or enzyme activity in its endosperm may be screened or selected based on a reduced level of the protein or enzyme (direct assay), or it may be based on the phenotype of the grain of the wheat plant such as an increased proportion of amylose or decreased proportion of amylopectin, or a visual phenotype, for example shrunken grain or altered starch granule properties. The wheat plant with the altered starch properties as used herein may be identified using any of the methods known in the art, either directly determining the starch properties or indirectly, for example, detecting the presence of a genetic variation in the plant or its grain. The plant may be a plant in a population of wheat plants, such as, for example, in wheat breeding.

The "wheat SBEIIa gene" or the like as used herein refers to a nucleotide sequence encoding starch branching enzyme IIa in wheat, which can readily be distinguished from SBEIIb or other proteins by those skilled in the art. This includes the naturally occurring variants of the genes existing in wheat, including those encoded by the A, B and D genomes of breadwheat, as well as non-naturally occurring variants which may be produced by those skilled in the art of gene modification. Examples are shown in Table 1. In a preferred embodiment, a wheat SBEIIa gene refers to a nucleic acid molecule, which may be present in or isolated from wheat or derived therefrom, comprising nucleotides having a sequence having at least 80% identity to the coding region of the wSBEIIa-D1 gene shown in SEQ ID NO: 1. In analogous fashion, a "wheat SBEIIb gene" as used herein refers to a nucleotide sequence encoding starch branching enzyme IIb in wheat. A partial wheat SBEIIb gene sequence (wbe2b genomic) from *T. aestivum* is shown in FIG. 2 (SEQ ID NO: 2). A wheat SBEIIb cDNA sequence is shown in FIG. 9.

In analogous fashion, the "wheat SSIIa gene" or the like as used herein refers to a nucleotide sequence encoding starch synthase IIa in wheat, which can readily be distinguished from other starch synthases or other proteins by those skilled in the art. This includes the naturally occurring variants of the genes existing in wheat, including those encoded by the A, B and D genomes of breadwheat, as well as non-naturally occurring variants which may be produced by those skilled in the art of gene modification. Examples are reported in WO00/66745. In a preferred embodiment, a wheat SSIIa gene refers to a nucleic acid molecule, which may be present in or isolated from wheat or derived therefrom, comprising nucleotides having a sequence having at least 80% identity to the coding region of the wSSIIa gene shown in WO00/66745.

SBE activity may be measured directly by enzyme assay, for example by the phosphorylase stimulation assay (Boyer and Preiss, 1978). This assay measures the stimulation by SBE of the incorporation of glucose 1-phosphate into methanol-insoluble polymer ($\alpha$-D-glucan) by phosphorylase a. SBE activity can be measured by the iodine stain assay, which measures the decrease in the absorbance of a glucan-polyiodine complex resulting from branching of glucan polymers. SBE activity can also be assayed by the branch linkage assay which measures the generation of reducing ends from reduced amylose as substrate, following isoamylase digestion (Takeda et al., 1993a). Preferably, the activity is measured in the absence of SBEI or SBEIIb activity. Isoforms of SBE show different substrate specificities, for example SBEI exhibits higher activity in branching amylose, while SBEIIa and SBEIIb show higher rates of branching with an amylopectin substrate. The isoforms may also be distinguished on the basis of the length of the glucan chain that is transferred. SBE protein may also be measured by using specific antibodies such as those described herein. The SBEII activity may be measured during grain development in the developing endosperm, or alternatively in the mature grain where the protein is still present in equivalent, but unaltered, grain and can be assayed by immunological methods. Starch synthase activity may be measured by extraction of proteins from endosperm and assay as described in Example 1.

In one embodiment the modified wheat having altered starch has an increased proportion of amylose in the grain starch to at least 30%. Ordinarily in hexaploid and durum wheats, the proportion of amylose in starch is in the range from about 18 to about 30% (w/w). In this embodiment, the modified wheat comprises one or more genetic variations which result in the starch in its grain comprising at least 30% amylose. The proportion of amylose in the starch as defined herein is on a weight/weight (w/w) basis, i.e. the weight of amylose as a percentage of the weight of total starch from the grain. In further embodiments, the proportion of amylose in the starch is at least 40%, at least 45%, at least 50%, at least 55%, at least 60%, at least 65%, at least 70% or at least 75% (each w/w). In further embodiments of the invention, the method provides for a proportion of amylase of at least 80% or at least 90% (w/w).

The wheat plants described herein for use in the invention include progeny plants which have the desired characteristics of the parental wheat plants, in genotype and/or phenotype, into which the modifications were introduced. The wheat plants also encompass the genetic variations(s) or mutations in other genetic backgrounds or other species which can be hybridised with the wheat plant as described above. The modified parental plants may be crossed with plants containing a more desirable genetic background. After the initial crossing, a suitable number of backcrosses may be carried out to remove the less desirable background. The desired genetic background may include a suitable combination of genes providing commercial yield and other characteristics such as agronomic performance or abiotic stress resistance. The genetic background might also include other altered starch biosynthesis or modification genes, for example genes from other wheat lines that have a shrunken endosperm where the causal gene is not known. The desired genetic background of the wheat may include considerations of agronomic yield and other characteristics. Such characteristics might include whether it is desired to have a winter or spring type of wheat, agronomic performance, disease resistance and abiotic stress resistance. In Australia one might want to cross the altered starch trait into wheat cultivars such as Baxter, Kennedy, Janz, Frame, Rosella, Cadoux, Diamondbird or other commonly grown varieties. The examples provided are specific for an Australian production region, and other varieties will be suited for other growing regions. It is preferred that the wheat variety of the invention provide a yield not less than 80% of the corresponding wild-type variety in at least some growing regions, more preferably not less than 90% and even more preferably not less than 95%. The yield can readily be measured in controlled field trials.

In an embodiment, the modified wheat plant comprises a mutation wherein the SBEIIa gene is absent from the long arm of chromosome 2A (2AL) or wherein the SBEIIa gene on the long arm of chromosome 2A comprises a mutation which leads to reduced level of SBEIIa enzyme activity in the endosperm of said grain relative to wild-type grain. Despite an extensive screen of 2400 wheat accessions, the inventors did not find such plants that were naturally occurring, suggesting that selection for retention of the functional SBEIIa gene on 2AL might be happening in nature. However, such plants could be produced and identified after mutagenesis. These plants are non-transgenic which is desirable in some markets. These plants may be bread wheat, durum wheat or other wheat. In a preferred embodiment, the wheat plant comprises a deletion of at least part of the SBEIIa gene, which may extend to at least part of the SBEIIb gene, on the 2AL chromosome. As is understood in the art, hexaploid wheats such as bread wheat comprise three genomes which are commonly designated the A, B and D genomes, while tetrapolid wheats such as durum wheat comprise two genomes commonly designated the A and B genomes. Each genome comprises 7 pairs of chromosomes which may be observed by cytological methods during meiosis and thus identified, as is well known in the art. Each chromosome has a centromere, which on chromosome 2 is positioned asymmetrically; therefore the two arms of chromosome 2 are designated "short"

and "long". The "long arm of chromosome 2A" is defined herein as the region of that chromosome 2A between the centromere and tip along the long arm, in accord with the standard meaning of the term. The terms "long arm of chromosome 2B" and the "long arm of chromosome 2D" are defined in the same way except that they relate to chromosome 2 of the B or D genomes of wheat, respectively.

We have found that the SBEIIa and SBEIIb genes are both present on chromosome 2 in wheat. In a particular embodiment, the wheat plant comprises the majority (>50%) of 2AL, which chromosome arm comprises a mutation of at least the SBEIIa gene. That is, chromosome 2AL is essentially present, comprising a mutation in at least the SBEIIa gene of the A genome. The presence of 2AL may be determined by cytological techniques such as, for example, in situ hybridization techniques or by using 2AL specific molecular markers. In a preferred embodiment, the wheat plant is homozygous for said mutation. The mutation may be a null mutation. The mutation may be a deletion.

The modified wheat plants may be transgenic or non-transgenic. The invention also extends to the grain produced from the wheat plants and any propagating material of the wheat plants that can be used to produce the plants with the desired characteristics, such as cultured tissue or cells. The invention clearly extends to methods of producing or identifying such wheat plants or the grain produced by such plants.

The modified wheat plants as described herein, particularly the grain obtained from the plants or products containing the altered wheat starch obtained from the grain may be used in the production of a food, beverage or pharmaceutical preparation which is intended for consumption by, or administration to, an animal, preferably a mammal and in particular a human. The food, beverage or pharmaceutical preparation comprises the modified wheat grain or a product derived therefrom comprising the altered starch.

Modified Grain

The invention also provides foods, beverages or pharmaceutical preparations produced with modified wheat grain or altered starch obtained therefrom, obtained from wheat plants as described herein. Grain is defined herein as essentially mature grain. This includes grain as harvested in a commercial setting. In one embodiment, the altered starch is at least partly a consequence of reduced SBEIIa activity during development of the endosperm of the wheat grain. The grain may comprise an increased proportion of amylose as a percentage of total starch. This may be determined as a reduced proportion of amylopectin in the starch compared to grain from a wild-type plant. Wild-type wheat starch has approximately 18-30% amylose and 70-80% amylopectin. The grain for use in the invention comprises starch comprising at least 30% amylose, preferably comprising at least 50% (w/w) amylose. In a further embodiment, both SBEIIa and SBEIIb activities are reduced during development of the endosperm. Increased amylose levels may be evidenced by abnormal starch granule morphology or loss of birefringence of the granules when observed under a light microscope or other methods known in the art. In a particular embodiment, the proportion of amylose in the starch of the grain is measured by an iodometric method, which may be a spectrophotometric method such as, for example, the method of Morrison and Laignelet (1983), or by high-performance liquid chromatography (HPLC, for example, Batey and Curtin, 1996).

The grain may be shrunken or non-shrunken, preferably having a non-shrunken phenotype. "Non-shrunken" as used herein is defined as where the majority of grains, preferably at least 90% of the individual grains, show a plump or fully-filled phenotype. This is usually associated with a normal or near normal level of starch accumulation. In contrast, a "shrunken" phenotype as used herein refers to the majority of grains, particularly at least 90% of the grains, having reduced starch accumulation. Slightly shrunken grain refers to a reduction in average starch content of at least 30%, moderately shrunken grain refers to a reduction in average starch content of at least 50%, and highly shrunken grain refers to a reduction in average starch content of at least 70%, each relative to wild-type grain. Shrunkenness may also be measured by the relative starch content, as a percentage of mature grain weight. Unaltered field-grown wheat grain has a starch content of about 65%, while in shrunken grain this is reduced to less than 50%.

In further embodiments, the grain has an average weight of at least 36 mg or 40 mg. The average weight of the grain is determined by measuring the weight of a known number of grains, being a representative sample of the batch of grain, and dividing the total weight by the number of grains. It would be appreciated that characteristics of the grain such as starch content, average weight and a non-shrunken phenotype that are near wild-type levels are desirable for commercial production of the grain. In further embodiments, the starch content of the grain is at least about 25%, 35%, 45%, or 55% to 65% (w/w). Wild-type wheat grown commercially usually has a starch content in the range 55-65%, depending somewhat on the cultivar grown. Alternatively, the grain of the invention has a starch content of at least 90% that of grain from an equivalent, but unaltered, wheat. Lower starch contents than wild-type are likely a consequence of reduced amylopectin levels. Even with lower starch contents, the grain may still be useful for commercial food production because of the relatively high value of the high amylose products. Other desirable characteristics include the capacity to mill the grain, in particular the grain hardness. Another aspect that might make a wheat plant of higher value is the degree of starch extraction from the grain, the higher extraction rates being more useful. Grain shape is also another feature that can impact on the commercial usefulness of a plant, thus grain shape can have an impact on the ease or otherwise with which the grain can be milled. For example, an elongated grain morphology may make it difficult to mill and process.

A fuller grain may be desirable in terms of achieving greater yields and certain benefits of the invention might be achieved, such as the production of starch with high levels of amylose, or in the alternative starch with altered chain length distributions. Thus the grain preferably has a non-shrunken phenotype. Other aspects of the invention may, however, be better achieved by a grain that is less filled. Thus the proportion of aleurone layer or germ or protein to starch may be higher in less filled grain, thereby providing for a wheat flour or other product that is higher in the beneficial constituents of the aleurone layer or protein. The high aleurone layer product might thus be higher in certain vitamins such as folate, or it might be higher in certain minerals such as calcium, and that combined with higher resistant starch levels might provide synergistic effects such as providing for enhanced uptake of minerals in the large bowel.

The invention also provides for the use of flour, meal, dough or other products produced from the grain or using the grain. These may be unprocessed or processed, for example by fractionation or bleaching. The invention further provides wheat grain useful for food production obtained from the wheat plant of the invention. Additionally the invention encompasses grain that has been processed in other ways, so that the grain may have been milled, ground, rolled, pearled, kibbled or cracked, or par boiled (polenta), for example as cons cous.

Altered Starch

In another aspect, the invention provides foods, beverages or pharmaceutical preparations produced with altered wheat starch obtained from the grain of the wheat plants as described herein, the starch having an increased proportion of amylose and a reduced proportion of amylopectin. As used herein, the term "starch" generally refers to the total starch of the grain or the starch prior to any fractionation that alters the ratio of amylose to amylopectin. The starch may be at least partly purified, i.e. it has been separated from at least one other component of the grain. As used herein, "substantially purified starch" means that at least 95% (w/w) of the dry weight of the composition is starch. Purified starch may be obtained from grain by a milling process, for example a wet milling process, which involves the separation of the starch from protein, oil and fibre. The initial product of the milling process is a mixture or composition of starch granules, and the invention therefore encompasses such granules, comprising the modified starch as described herein.

In further embodiments, the altered starch has altered physical characteristics such as, for example, an increased or reduced gelatinisation temperature, altered swelling characteristics during or following gelatinisation, altered viscosity, an altered chain length distribution in the amylopectin, or any combination of these. Gelatinisation is the heat-driven collapse (disruption) of molecular order within the starch granule in excess water, with concomitant and irreversible changes in properties such as granular swelling, crystallite melting, loss of birefringence, viscosity development and starch solubilisation. High amylose starch from ae (amylose extender) mutants of maize showed a higher gelatinisation temperature than normal maize (Fuwa et al., 1999, Krueger et al., 1987). On the other hand, starch from barley sex6 mutants that lack starch synthase IIa activity had lower gelatinisation temperatures and the enthalpy for the gelatinisation peak was reduced when compared to that from control plants (Morell et al., 2003). The gelatinisation temperature of wild-type wheat starch is typically about 61° C. (Rahman et al, 2000) for the temperature of the first peak, defined as the onset temperature, as measured by differential scanning calorimetry. The increased or reduced gelatinisation temperature may be for the first peak of gelatinisation, the second peak, or both. One or more properties of the starch such as, for example, the enthalpy of gelatinisation, may be unaltered. The starch may have an increased or reduced gelatinisation temperature, preferably an increased gelatinisation temperature. For example, we have observed that the starch obtained from SBEIIa-reduced wheat has an increased gelatinization temperature, while that for SSIIa-reduced wheat has a reduced gelatinization temperature. The temperature of the first peak (apex) of gelatinisation as measured by differential scanning calorimetry may be increased or decreased by at least 3° C. or 5° C., preferably by at least 7° C. or 8° C. and more preferably by at least 10° C. compared to the temperature of the first peak for the corresponding starch from wild-type grain. In a particular embodiment, the increase or decrease is in the range of 3° C. to 12° C. Of particular note, the gelatinisation temperature may have a decreased temperature of onset of the first peak combined with an increased temperature of the peak apex. In another embodiment which is not mutually exclusive with the previous, the starch has an altered gelatinisation temperature for the first peak but exhibits a substantially unaltered temperature for the second peak, which corresponds to amylose-lipid dissociation, as determined by DSC. In a further embodiment, the starch exhibits a decreased enthalpy during gelatinisation, such as, for example, a decrease by at least 25% or at least 40% compared to that of corresponding wild-type wheat starch.

The starch may also be characterized by its swelling rate in heated excess water compared to wild-type starch. Swelling volume is typically measured by mixing either a starch or flour with excess water and heating to elevated temperatures, typically greater than 90° C. The sample is then collected by centrifugation and the swelling volume is expressed as the mass of the sedimented material divided by the dry weight of the sample. A low swelling characteristic is useful where it is desired to increase the starch content of a food preparation, in particular a hydrated food preparation.

The starch structure of the wheat of selected forms of the present invention may also differ in that the degree of crystallinity is reduced compared to normal starch isolated from wheat. The reduced crystallinity of a starch is also thought to be associated with enhanced organoleptic properties and contributes to a smoother mouth feel. Thus the starch may additionally exhibit reduced crystallinity resulting from reduced levels of activity of one or more amylopectin synthesis enzymes. Crystallinity is typically investigated by X-ray crystallography.

One measure of an altered amylopectin structure is the distribution of chain lengths, or the degree of polymerization, of the starch. The chain length distribution may be determined by using fluorophore-assisted carbohydrate electrophoresis (FACE) following isoamylase de-branching. The amylopectin of the starch of the invention may have a distribution of chain length in the range from 5 to 60 that is greater than the distribution of starch from wild-type plants upon debranching. Starch with longer chain lengths will also have a commensurate decrease in frequency of branching. Thus the starch may also have a distribution of longer amylopectin chain lengths in the amylopectin still present.

In another embodiment, the starch comprises an elevated level of resistant starch, with an altered structure indicated by specific physical characteristics. Such characteristics may include physical inaccessibility to digestive enzymes which may be by reason of having altered starch granule morphology, the presence of appreciable starch associated lipid, altered crystallinity, altered amylopectin chain length distribution, or any combination of these. The high proportion of amylose also contributes to the level of resistant starch.

The invention also provides starch from grain of the exemplified wheat plant comprising increased amounts of dietary fibre, preferably in combination with an elevated level of resistant starch. This increase is also at least in part a result of the high relative level of amylose.

The invention clearly extends to methods of producing the wheat starch described herein. In one embodiment, the method comprises the steps of obtaining wheat grain as described herein and extracting the starch from the grain. The wheat grain may be obtained by growing the wheat plants described herein and harvesting the grain, or from a producer of the grain or importer of the grain.

Foods, Beverages and Pharmaceutical Products

The invention also encompasses foods, beverages or pharmaceutical preparations produced with modified wheat or altered starch as described herein, preferably obtained from wheat plants that have reduced SBEIIa activity. In an embodiment, the wheat plant has an alteration, preferably a reduction, in at least one starch biosynthetic enzyme other than SBEIIa Plants having reduced SBEIIa and SBEIIb activities may be produced by crossing a plant reduced for SBEIIa with a plant reduced for SBEIIb, or by introducing a transgene encoding a molecule that inhibits expression of both SBEIIa and SBEIIb genes. Because of the close linkage of the SBEIIa and SBEIIb genes in wheat as revealed herein, plants reduced for both activities may also be produced by identifying varieties lacking the SBEIIa and SBEIIb isoforms encoded by one of the genomes of wheat, and crossing such varieties to produce a plant reduced for the isoforms encoded by at least two genomes. Such food production might include the making of flour, dough or other products that might be an ingredient in commercial food production.

Starch is the major source of carbohydrate in most human diets and the grain of the invention and products derived from it can be used to prepare food. The foods may be consumed by humans or animals, particularly mammalian animals, for example during livestock production or in pet-food. As used herein, "mammals" or "mammalian" refers to any member of the Mammalia. The grain derived from the altered wheat plant can be used readily in food processing procedures and therefore the invention includes milled, ground, kibbled, pearled or rolled grain or products obtained from the processed or whole grain of the wheat plant referred to above, including flour. These products may be then used in various food products, for example farinaceous products such as breads, cakes, biscuits and the like or food additives such as thickeners or binding agents or to make drinks, noodles, pasta or quick soups. The grain or products derived from the grain of the invention are particularly desired in breakfast cereals or as extruded products. The high amylose starches of the invention can also be used to form high strength gels that are useful in the confectionery industry or allow lower molding and curing times. They may also be used as a coating, for example to reduce oil absorption in deep-fried potato or other foods.

Dietary Fibre

Dietary fibre, in this specification, is the carbohydrate and carbohydrate digestion products that are not absorbed in the small intestine of healthy humans but enter the large bowel. This includes resistant starches, β-glucans and other soluble and insoluble carbohydrate polymers. It is thought to comprise that portion of carbohydrates that are fermentable, at least partially, in the large bowel by the resident microflora.

The starch of the invention preferably contains relatively high levels of dietary fibre, more particularly amylose. The dietary fibre content of the grain of the present invention may or may not result solely from the increased relative endospermal amylose content.

Aspects of this invention might also arise from the combination of the aleurone layer and germ in combination with high levels of dietary fibre. Specifically, this may arise where higher relative levels of aleurone or germ are present in the grain. Where the wheat grain is slightly shrunken the endosperm is present in reduced amounts and the aleurone layer and the germ are present in relatively elevated amounts. Thus the wheat has a relatively high level of certain beneficial elements or vitamins in combination with elevated resistant starch. Such elements include divalent cations (including bioavailable $Ca^{++}$) and vitamins such as folate or antioxidants such as tocopherols or tocotrienols. One specific form of milled product might be one where the aleurone layer is included in the milled product. Particular milling process might be undertaken to enhance the amount of aleurone layer in the milled product. Thus, any product derived from grain milled or otherwise processed to include aleurone layer and germ will have the additional nutritional benefits, without the requirement of adding these elements from separate sources.

Resistant Starch

Resistant starch is defined as the sum of starch and products of starch digestion not absorbed in the small intestine of healthy humans but entering into the large bowel. Thus, resistant starch excludes products digested and absorbed in the small intestine. Resistant starches include physically inaccessible starch (RS1 form), resistant granules (RS2), retrograded starches (RS3) and chemically modified starches (RS4). The altered starch structure and in particular the high amylose levels of the starch of the invention give rise to an increase in resistant starch when consumed in food. The starch may be in an RS1 form, being somewhat inaccessible to digestion. Starch-lipid association, as measured by V-complex crystallinity, is also likely to contribute to the level of resistant starch. The level of resistant starch present in a food or other products is preferably measured in rum as described in Example 13, or in viva as described in Example 16.

It will be understood that one benefit of the present invention is that it provides for products that are of particular nutritional benefit and, moreover, it does so without the need to modify the starch or other constituents of the wheat grain. However it may be desired to make modifications to the starch or other constituent of the grain, and the invention encompasses such a modified constituent. Methods of modification are well known and include the extraction of the starch or other constituent by conventional methods and modification of the starches to increase the resistant form. The starch may be modified by treatment with heat and/or moisture, physically (for example ball milling), enzymatically (using for example α- or β-amylase, pullalanase or the like), chemical hydrolysis (wet or dry using liquid or gaseous reagents), oxidation, cross bonding with difunctional reagents (for example sodium trimetaphosphate, phosphorous oxychloride), esterification or carboxymethylation.

Glycemic Index

Glycaemic Index (GI) relates to the rate of digestion of foods comprising the starch, and is a comparison of the effect of a test food with the effect of white bread or glucose on excursions in blood glucose concentration. The Glycaemic Index is a measure of the likely effect of the food concerned on post-prandial serum glucose concentration and demand for insulin for blood glucose homeostasis. One important characteristic provided by foods of the invention is a reduced glycaemic index. Furthermore, the foods may have a low level of final digestion and consequently be relatively low-kilojoule, or may be described as low energy-density foods. A low calorific product might be based on inclusion of flour produced from milled wheat grain. Such foods may have the effect of being filling, enhancing bowel health, reducing the post-prandial serum glucose and lipid concentration as well as providing for a low metaholisable energy food product.

Bread

In bread the altered wheat starch in the form of flour or wholemeal may substitute for 10% (w/w) or more of unaltered flour or wholemeal, preferably substituting at least 30% and even more preferably at least 50% of the unaltered flour or wholemeal. The formulation might therefore be, for example, flour 90 parts, altered wheat starch 10 parts, fat 2 parts, salt 2 parts, improver 1 part, yeast 2.5 parts. The production of the bread may be by a rapid dough technique or other techniques as is known by those skilled in the art.

Pasta Product

The altered wheat starch may be incorporated into a farinaceous based pasta product. The amount of altered wheat starch employed in the pasta composition may be in the range of 10-40% (w/w) or more based on the total weight of farinaceous material more particularly in the range of 15 to 35%. Suitable other farinaceous materials will readily be chosen by a person skilled in the art.

Other material may also be added to the composition for example dry or liquid eggs (yolks, whites, or both) or high protein substances such as milk protein or fish protein. Vitamins, minerals, calcium salts, amino acids, buffering agents such as disodium hydrogen phosphate, seasoning, gum, gluten or glyceryl monostearate may also be added.

In the preparation of pasta, the ingredients may first be dry blended until they are uniformly dispersed. Water is then added to the dry blend with continued mixing until a dough is obtained with is plastic enough to be sheeted or extruded but firm enough to cohere. The paste formulation will normally contain about 75 parts of dry farinaceous material and about 25 parts of water. These proportions will vary depending on such factors as the variety of flour employed, gluten quality, protein content, initial flour moisture and flour particle size. The pasta may be shaped and then dried using methods known in the art preferably with the starch component in an ungelatinised form.

Pharmaceutical Product

Compositions for oral delivery may be in the form of tablets, lozenges, aqueous or oily suspensions, granules, powders, emulsions, capsules, caplets, gelcaps, syrups or elixirs, for example. Orally administered compositions may contain one or more optional agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions may be coated to delay disintegration and absorption in the gastrointestinal tract thereby providing a sustained action over an extended period of time. Selectively permeable membranes surrounding an osmotically active driving compound are also suitable for orally administered compounds of the invention. In these later platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time delay material such as glycerol monostearate or glycerol stearate may also be used. Oral compositions can include standard vehicles such as mannitol, lactose, starch, magnesium stearate, sodium saccharine, cellulose, magnesium carbonate, etc. Such vehicles are preferably of pharmaceutical grade.

Methods of Reducing Gene Activity

The expression and/or activity of SBEIIa, SBEIIb or other starch biosynthesis or modification genes may be altered by introducing one or more genetic variations into the wheat plant. As used herein, a "genetic variation" means any heritable alteration in the genome of the wheat plant which, in this context, affects the expression or activity of the gene of interest. Genetic variations include mutations such as point mutations, insertions, substitutions, inversions, duplications, translocations and preferably deletions, and the introduction of one or more transgenes into the genome.

The phrases "nucleic acid molecule" and "nucleic acid sequence" as used herein refer to a polymer of nucleotides, which may be single-stranded or double-stranded. It may comprise DNA such as, for example, genomic DNA or cDNA, or RNA, mRNA or any combinations of these. For introduction into wheat cells, a nucleic acid molecule may be chemically modified for improved delivery or stability, or protected as part of a vector such as a viral vector. The nucleic acid molecule may be obtained by cloning techniques or synthesized by techniques well known in the art. The nucleic acid molecule may comprise a coding strand or non-coding strand (antisense) or a combination of these such as, for example, in inverted repeat constructs. In reference to nucleic acid sequences which "correspond" to a gene, the term "correspond" refers to a nucleotide sequence relationship, such that the nucleotide sequence has a nucleotide sequence which is the same as the reference gene or an indicated portion thereof, or has a nucleotide sequence which is exactly complementary in normal Watson-Crick base pairing, or is an RNA equivalent of such a sequence, for example, an mRNA, or is a cDNA derived from an mRNA of the gene.

Nucleotide sequences are presented herein by a single strand sequence in the 5' to 3' direction, using the standard one letter nucleotide abbreviations. "Complementary" describes the relationship between two single-stranded nucleic acid molecules or sequences that anneal by base-pairing. For example, 5'-GACT-3' pairs with its complement, 5'-AGTC-3'. "Homology" or "homologous" refers to sequence similarity or identity between two or more nucleotide sequences or two or more polypeptide sequences, according to the context. The term "percent identity" as applied to nucleotide sequences refers to the percentage of nucleotide matches between two nucleotide sequences aligned using a standardized algorithm such as, for example, the CLUSTAL V algorithm or the Blastn or BLAST 2 Sequences programs available from the National Center for Biotechnology Information, available on the Internet at http://www.ncbi.nlm.nih.gov/BLAST/, and preferably set at default parameters. In similar fashion, "percent identity" may refer to polypeptide sequences.

Reference herein to a "gene" including an SBEIIa, SSIIa, SBEIIb or other starch biosynthetic gene, or genes encoding antisense, co-suppression, ribozyme, duplex RNA molecules or the like, is to be taken in its broadest context and includes a classical genomic gene having a transcribed region associated with regulatory regions such as promoters and transcription terminators-polyadenylation sequences. The transcribed region includes transcribed but not translated sequences (untranslated sequences, UTR) and optionally may include a protein coding region or introns, which are spliced out to form a mature RNA, or any combination of these. A "gene" includes forms obtained from cDNA, corresponding to the exons, and RNA genes such as those found on RNA genomes. The term "gene" is also used to describe synthetic or fusion molecules encoding all or part of a functional product.

When present in a cell, preferably a wheat cell, a "gene" directs the "expression" of a "biologically active" molecule or "gene product", which may be RNA or a polypeptide. This process is most commonly by transcription to produce RNA and translation to produce protein. Such a product may be subsequently modified in the cell. RNA may be modified by, for example, polyadenylation, splicing, capping, dicing into 21-23 nucleotide fragments, or export from the nucleus or by covalent or noncovalent interactions with proteins. Proteins may be modified by, for example, phosphorylation, glycosylation or lipidation. All of these processes are encompassed by the term "expression of a gene" or the like as used herein.

As used herein, the terms "wheat SBEIIa gene" and "wheat SBEIIb gene" and related terms refer to the genes that have been identified from wheat that encode SBEIIa or SBEIIb enzymes, respectively, and homologous genes present in other wheat varieties. These include, but are not limited to, the gene sequences listed in Table 1. It would be understood that there is natural variation in the sequences of SBEIIa and SBEIIb genes from different wheat varieties. The homologous genes are readily recognizable by the skilled artisan. The degree of sequence identity between homologous SBEIIa genes or the proteins is thought to be at least 80%, similarly for SBEIIb genes or proteins. Analogous definitions apply to "wheat SSIIa gene" and the like.

The genes for use in the invention may be derived from a naturally occurring SBEIIa, SBEIIb or other starch biosynthetic gene by standard recombinant techniques. A "recombinant nucleic acid molecule" or like term as used herein refers to a sequence that is not naturally occurring or has a sequence that is made by an artificial combination of two or more otherwise separated segments of sequence. This artificial combination may be formed by chemical synthesis or, more commonly, by the artificial manipulation of isolated segments of nucleic acids, for example by genetic engineering techniques well known in the art. The term "recombinant" includes nucleic acids that have been altered solely by addition, substitution, or deletion of a portion of the nucleic acid. Frequently, a recombinant nucleic acid may include a nucleic acid sequence operably linked to a promoter sequence. Such a recombinant nucleic acid may be part of a vector that is used, for example, to transform a cell.

Generally, a gene may be subjected to mutagenesis to produce single or multiple nucleotide substitutions, deletions and/or additions such as, for example, codon modification. Nucleotide insertional derivatives of such genes include 5' and 3' terminal fusions as well as intra-sequence insertions of single or multiple nucleotides. Insertional nucleotide sequence variants are those in which one or more nucleotides are introduced into a predetermined site in the nucleotide sequence, although random insertion is also possible with suitable screening of the resulting product. Deletional variants are characterised by the removal of one or more nucleotides from the sequence. Substitutional nucleotide variants are those in which at least one nucleotide in the sequence has been removed and a different nucleotide inserted in its place. Such a substitution may be "silent" in that the substitution does not change the amino acid defined by the codon. Alternatively, conservative substituents are designed to alter one amino acid for another similar acting amino acid. Typical substitutions are those made in accordance with the following:

| Suitable residues for conservative amino acid substitutions | |
|---|---|
| Original Residue | Exemplary Substitutions |
| Ala | Ser |
| Arg | Lys |
| Asn | Gln; His |
| Asp | Glu |
| Cys | Ser |
| Gln | Asn |
| Glu | Asp |
| Gly | Ala |
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

Transgenes

The expression and/or activity of SBEIIa, SBEIIb or other starch biosynthesis or modification genes may be altered by introducing one or more transgenes into the wheat plant. A "transgene" as referred to herein has the normal meaning in the art of biotechnology and includes a genetic sequence which has been produced or altered by recombinant DNA or RNA technology and which has been introduced into the organism or cell, preferably wheat cell, of interest. The transgene may include genetic sequences derived from the organism or cell, for example an antisense sequence. The transgene typically includes an exogenous nucleic acid which is not derived from said organism or cell. "Transgenic" refers to the organism or cell containing a transgene, or the genetic sequence that was introduced into the organism or cell or its progenitor. "Non-transgenic" refers to the absence of any transgene in the genome. A transgene is preferably integrated into the genome of the organism or cell, for stable inheritance.

Those skilled in the art will be aware that expression of a gene or a complementary sequence thereto in a cell requires said gene to be placed in operable connection with a promoter sequence. The choice of promoter for the present purpose may vary depending upon the level of expression required and/or the tissue, organ and species in which expression is to occur, and is preferably an endosperm specific promoter that provides preferential expression in the developing endosperm of wheat.

Placing a nucleic acid molecule under the regulatory control of a promoter sequence means positioning said molecule such that expression is controlled by the promoter sequence. A promoter is usually, but not necessarily, positioned upstream, or at the 5'-end, of the nucleic acid molecule it regulates. Furthermore, the regulatory elements comprising a promoter are usually positioned within 2 kb of the start site of transcription of the gene. In the construction of heterologous promoter/structural gene combinations, it is generally preferred to position the promoter at a distance from the gene transcription start site that is approximately the same as the distance between that promoter and the gene it controls in its natural setting (i.e., the gene from which the promoter is derived). As is known in the art, some variation in this distance can be accommodated without loss of promoter function. Similarly, the preferred positioning of a regulatory sequence element with respect to a heterologous gene to be placed under its control is defined by the positioning of the element in its natural setting (i.e., the gene from which it is derived). Again, as is known in the art, some variation in this distance can also occur.

Examples of promoters suitable for use in gene constructs of the present invention include promoters derived from the genes of viruses, yeast, moulds, bacteria, insects, birds, mammals and plants, preferably those capable of functioning in plant cells, more preferably those capable of being expressed in the endosperm of wheat. The promoter may regulate expression constitutively, or differentially, with respect to the tissue in which expression occurs. Alternatively, expression may be differential with respect to the developmental stage at which expression occurs, or in response to external stimuli such as physiological stresses, or temperature.

The method of reducing SBEIIa, SBEIIb or other starch biosynthetic gene activity may comprise the step of introducing a transgene into a regenerable cell of wheat and regenerating a transgenic wheat plant from the transformed cell. The branching enzymes involved in synthesis of amylopectin include SBEI, SBEIIa and SBEIIb and the invention encompasses a reduced expression of SBEIIa alone or in combination with alteration of SBEIIb or SBEI expression. Therefore, the transgene(s) may inactivate more than one of these genes. Moreover, the inactivation of SBEIIb and/or SBEI may be direct, in that the transgene (e.g. encoding duplex RNA, antisense, or ribozyme RNA, see below) directly targets the SBEIIb or SBEI gene expression, or it may indirectly result in the alteration in the expression of SBEIIb or SBEI. For example, the transgene RNA may target only the SBEIIa gene/RNA in terms of sequence identity or basepairing but also result in reduction of SBEIIb or SBEI activity by altering protein stability or distribution in the endosperm. Additionally forms of the present invention reside in the combination of an altered activity of SBEIIa and an alteration of one or more other amylopectin synthesis enzymes, which enzymes may include SSI, SSIIa, SSIIb, SSIII, phosphorylase and debranching enzymes such as isoamylase or pullulanase. Expression of any or all of these may be altered by introduction of a transgene.

Several DNA sequences are known for amylopectin synthesis genes in wheat, any of which can be the basis for designing transgenes for inactivation of the genes in wheat. These include SBEIIa (GenBank accession numbers Y11282, AF338431 and AF338432) and SBEIIb (WO 00/15810, WO 01/62934). The SBEI gene of wheat is described in Rahman et al., (1997) and Rahman et al., (1999). The *Triticum tauschii* sequence for SBEI, which is highly homologous to the wheat D genome SBEI gene, can be found in published Patent specification WO 99/14314. A cDNA sequence for SBEI of wheat can be accessed in the GenBank database under accession number AF076679. Homologues of other amylopectin synthesising genes from barley or other closely related species can also be used to modify gene expression levels in wheat. Such genes or fragments thereof can be obtained by methods well known in the art, including PCR amplification or hybridization to labeled probes.

"Stringent hybridization conditions" as used herein means that hybridization will generally occur if there is at least 90% and preferably at least 95% sequence identity between the probe and the target sequence. Examples of stringent hybridization conditions are overnight incubation in a solution comprising 50% formamide, 5×SSC (1×SSC=150 mM NaCl, 15 mM trisodium citrate), 50 mM sodium phosphate (pH 7.6), 5×Denhardt's solution, 10% dextran sulfate, and 20 μg/ml denatured sheared carrier DNA such as salmon sperm DNA, followed by washing the hybridization support in 0.1×SSC at approximately 65° C. Other hybridization and wash conditions are well known and are exemplified in Sambrook et al, Molecular Cloning: A Laboratory Manual, Second Edition, Cold Spring Harbor, N.Y. (1989), particularly chapter 11.

The region(s) of the homologues used in preparing the transgene construct should have at least 85% identity to the corresponding wheat gene or gene region, preferably at least 90% and even more preferably 95-100% identity in the appropriate region. It is also preferred that the transgene specifically target the amylopectin synthesis genes expressed in the endosperm of wheat and have less or minimal effect on amylopectin synthesis elsewhere in the plant. This may be achieved by use of suitable regulatory sequences such as endosperm-specific promoters in the transgene.

Antisense

Genetic engineering approaches to altering, in particular specifically reducing, gene activity in plants such as wheat are well known in the art. These methods include the introduction of gene constructs for expression of a suitable antisense molecule that comprises nucleotides that are complementary in sequence to at least part of the RNA of the target gene and can hybridize with it. Antisense molecules are thought to interfere with the translation or processing or stability of the mRNA of the target gene, thereby inactivating expression of the gene. Methods of devising antisense sequences are well known in the art and examples of these can be found in U.S. Pat. No. 5,190,131, European patent specification 0467349-A1, European patent specification 0223399-A1 and European patent specification 0240208, which are incorporated herein by reference. The use of antisense methods in plants has been reviewed by Bourque (1995) and Senior (1998). Bourque lists a large number of examples of gene inactivation using antisense sequences in plant systems. She also states that attaining 100% inhibition of an enzyme activity may not be necessary as partial inhibition will more than likely result in measurable change in the system. Senior (1998) states that antisense methods are now a very well established technique for manipulating gene expression in plants.

Antisense molecules for wheat SBEIIa, SBEIIb, SBEI or other starch biosynthesis or modification genes can be based on the wheat mRNA sequences or derived from homologous DNA or mRNA sequences obtained from other species, for example barley. The antisense sequences may correspond to all or part of the transcripts of any of these genes or for sequences that effect control over their expression, for example their splicing. The antisense sequence may correspond to the targeted coding region of the wheat SBEIIa or other gene, or the 5'-untranslated region (UTR) or the 3'-UTR or combination of these. It may be complementary in part to intron sequences, which may be spliced out during or after transcription, preferably only to exon sequences of the target gene. In view of the generally greater divergence of the UTRs, targeting these regions provides greater specificity of gene inhibition. In particular embodiments, the length of the antisense sequence is at least 19 contiguous nucleotides, at least 50, at least 100, at least 200, at least 500 or at least 1000 nucleotides corresponding to the complement of the gene RNA sequence. The full-length sequence complementary to the entire gene transcript may be used. In a particular embodiment, the length of the antisense sequence is 100-2000 nucleotides. In further embodiments, the degree of sequence identity of the antisense sequence to the complement of the targeted transcript is at least 85%, at least 90% or 95-100%. The antisense RNA molecule may of course comprise unrelated sequences which may function to stabilize the molecule.

Cosuppression

Another molecular biological approach that may be used is co-suppression. The mechanism of co-suppression is not well understood but is thought to involve post-transcriptional gene silencing (PTGS) and in that regard may be very similar to many examples of antisense suppression. It involves introducing an extra copy of a gene or a fragment thereof into a plant in the sense orientation with respect to a promoter for its expression. The size of the sense fragment, its correspondence to target gene regions, and its degree of sequence identity to the target gene are as for the antisense sequences described above. In some instances the additional copy of the gene sequence interferes with the expression of the target plant gene. Reference is made to Patent specification WO 97/20936 and European patent specification 0465572 for methods of implementing co-suppression approaches.

Double Stranded RNA-Mediated Gene Silencing

A further method that might be employed to introduce genetic variation into the wheat plant is duplex or double stranded RNA mediated gene silencing. This method also involves PTGS. In this method a DNA is introduced that directs the synthesis of an at least partly double stranded RNA product(s) with homology to the target gene to be inactivated. The DNA therefore comprises both sense and antisense sequences that, when transcribed into RNA, can hybridize to form the double-stranded RNA region. In a preferred embodiment, the sense and antisense sequences are separated by a spacer region that comprises an intron which, when transcribed into RNA, is spliced out. This arrangement has been shown to result in a higher efficiency of gene silencing. The double-stranded region may comprise one or two RNA molecules, transcribed from either one DNA region or two. The presence of the double stranded molecule triggers a response from an endogenous plant system that destroys both the double stranded RNA and also the homologous RNA transcript from the target plant gene, efficiently reducing or eliminating the activity of the target gene. Reference is made to Australian Patent specification 99/29514-A and Patent specification WO 99/53050 for methods of implementing this technique. In particular embodiments, the length of the sense and antisense sequences that hybridise are at least 19 contiguous nucleotides, at least 30, at least 50, at least 100, at least 200, at least 500 or at least 1000 nucleotides. The full-length sequence corresponding to the entire gene transcript may be used. In a particular embodiment, the lengths are in the range 100-2000 nucleotides. In further embodiments, the degree of sequence identity of the sense and antisense sequences to the targeted transcript is at least 85%, at least 90% or 95-100%. The RNA molecule may of course comprise unrelated sequences which may function to stabilize the molecule. The RNA molecule may be expressed under the control of a RNA polymerase II or RNA polymerase III promoter. Examples of the latter include tRNA or snRNA promoters. The double-stranded RNA molecule may also comprise sequences from more than one gene, joined together, and thereby target multiple genes.

Ribozymes

The genetic variation responsible for the desired inactivation of gene expression in wheat may comprise a nucleic acid molecule encoding one or more ribozymes. Ribozymes are RNA molecules with enzymatic or catalytic function that can cleave other RNA molecules at specific sites defined by one or often two hybridizing sequences. The cleavage of the RNA inactivates the expression of the target gene. The ribozymes may also act as an antisense molecule, which may contribute to the gene inactivation. The ribozymes contain one or more catalytic domains, preferably of the hammerhead or hairpin type, between the hybridizing sequences. Other ribozyme motifs may be used including RNAseP, Group I or II introns, and hepatitis delta virus types. Reference is made to European patent specification 0321201 and U.S. Pat. No. 6,221,661. The use of ribozymes to inactivate genes in transgenic plants has been demonstrated, for example by Wegener et al (1994).

Genetic Constructs/Vectors

The invention also provides isolated nucleic acid molecules comprising RNA or DNA, preferably DNA, which encode the gene-inhibiting molecule. In certain embodiments, the nucleic acid molecules encode antisense, sense (co-suppression), double-stranded RNA or ribozyme molecules which target the wheat SBEIIa gene sequence and which inactivate its expression in endosperm of wheat grain. The invention also provides genetic constructs comprising or encoding the isolated nucleic acid molecule, comprising one or more regulatory elements such as promoters, enhancers and transcription termination or polyadenylation sequences. Such elements are well known in the art. The genetic constructs may also comprise intron sequences that aid expression of the transgene in plants, particularly in monocotyledonous plants such as wheat. The term "intron" is used in its normal sense as meaning a genetic segment that is transcribed but does not encode protein and which is spliced out of an RNA before translation. Introns may be incorporated in a 5'-UTR or a coding region if the transgene encodes a translated product, or anywhere in the transcribed region if it does not.

The invention further provides vectors, for example plasmid vectors, comprising the genetic constructs. The term "vector" includes an expression vector, being capable of in vitro or in vivo expression, and a transformation vector, capable of being transferred from one cell or organism to another. The vectors comprise sequences that provide for replication in cells, for example in prokaryotic cells such as *E. coli* or *Agrobacterium*. In a particular embodiment, the vector is a binary vector comprising a T-DNA sequence, defined by at least one T-DNA border sequence, that can be introduced into wheat cells. The invention further provides cells comprising the vectors, for example *Agrobacterium* or wheat cells which may be regenerable cells such as the cells of the scutellum of immature embryos. Alternatively, the cells may be transformed wheat cells comprising the transgene.

Promoters/terminators

In another embodiment, the transgene or other genetic construct of the invention includes a transcriptional initiation region (promoter) that may provide for regulated or constitutive expression in the endosperm of wheat. The promoter may be tissue specific, conferring expression selectively or exclusively in the endosperm. The promoter may be selected from either endosperm-specific (such as High Molecular Weight Glutenin promoter, the wheat SSI promoter, wheat SBEII promoter, wheat GBSS promoter) or promoters not specific for the endosperm (such as ubiquitin promoter or CaMV35S or enhanced 35S promoters). The promoter may be modulated by factors such as temperature, light or stress. Ordinarily, the promoter would be provided 5' of the genetic sequence to be expressed. The construct may also contain other elements that enhance transcription such as the nos 3' or the ocs 3' polyadenylation regions or transcription terminators. The regions of DNA illustrated will be incorporated into vectors containing suitable selectable marker gene sequences and other elements, or into vectors that are co-transformed with vectors containing these sequences.

Transformation Methods for Wheat

Methods for transformation of monocotyledonous plants such as wheat, that is for introducing genetic variation into the plant by introduction of an exogenous nucleic acid, and for regeneration of plants from protoplasts or immature plant embryos are well known in the art, see for example, Becker et al 1994, Cheng et al 1997, He et al 1994, Hess et al 1990, Nehra et al 1994, Vasil et al 1992, Vasil et al 1993, Weeks et al 1993, Weir et al 2001, Australian Patent Application No. 75460/94, European Patent Application No. 709462, International Patent Publication Nos. WO93/04178, WO89/12012, WO94/13822 and WO99/14314. Vectors carrying the desired nucleotide sequence or genetic construct and a selectable marker may be introduced into regenerable wheat cells of tissue cultured plants or explants, or suitable plant systems such as protoplasts. The selectable marker gene may provide antibiotic or herbicide resistance to the wheat cells, or allow the utilization of substrates such as mannose. The selectable marker preferably confers asulam, geneticin or hygromycin resistance to the wheat cells. The regenerable wheat cells are preferably from the scutellum of immature embryos, mature embryos, callus derived from these, or the meristematic tissue.

The transformed plant may contain a selectable marker gene, or such gene may be removed during or after regeneration, for example by excision of the selectable marker gene out of the genome or by segregation of the selectable marker gene away from the SBEIIa-inhibiting transgene.

Plants where the transgene or mutation has been integrated into a chromosome can be screened for by, for example, using a suitable nucleic acid probe specific for the transgene or phenotypic observation. Any of several methods may be employed to determine the presence of a transformed plant. For example, polymerase chain reaction (PCR) may be used to amplify sequences that are unique to the transformed plant, with detection of the amplified products by gel electrophoresis or other methods. DNA may be extracted from the plants using conventional methods and the PCR reaction carried out using primers that will distinguish the transformed and non-transformed plants. For example, primers may be designed that will amplify a region of DNA from the transformation vector reading into the construct and the reverse primer designed from the gene of interest. These primers will only amplify a fragment if the plant has been successfully transformed. An alternative method to confirm a positive transformant is by Southern blot hybridization, well known in the art. Plants which are transformed or mutant may also be identified i.e. distinguished from non-transformed or wild-type plants by their phenotype, for example conferred by the presence of a selectable marker gene, or the presence of a particular protein by immunological methods, or by the absence of a protein, for example that absence of the SBEIIa protein in the endosperm as detected by ELISA assay or Western blot analysis. An indication used in screening such plants might also be by observation of the phenotypic traits of the grain, for example by visual inspection or measurement of shrunken grain, or testing for elevated amylose content, or checking microscopically for the presence of birefringence.

Mutation

Introduction of the genetic variation leading to reduced activity of the SBEIIa enzyme or other starch biosynthetic enzyme in the wheat endosperm may also be achieved by the appropriate mutations within the respective gene or regulatory sequences of the gene. In the context of this application, an "induced mutation" is an artificially induced genetic variation which may be the result of chemical, radiation or biologically-based mutagenesis, for example transposon or T-DNA insertion. The extent to which the gene is inhibited will to some degree determine the characteristics of the starch made. The mutations may be truncation or null mutations and these are known to have a significant impact on the nature of the starch, however an altered starch structure will also result from a leaky mutation that sufficiently reduces amylopectin synthesis enzyme activity to provide the characteristic of interest in the starch or grain of wheat. Other chromosomal rearrangements may also be effective and these might include insertions, deletions, inversions, duplication or point mutations. A "null mutation" as used herein refers to a mutation which results in the complete or near complete loss of activity of the gene of interest such as, for example, where the gene activity can no longer be detected.

The SBEIIa gene is located on the long arm of chromosome 2. It is preferred that mutations to the gene or other genes, particularly deletion mutations, are localised to the gene of interest, for example the SBEIIa gene or perhaps extended to the linked SBEIIb gene in the case of a double mutant. A gene in this context includes the promoter region and transcription termination/polyadenylation signals as well as the transcribed region. The transcribed region includes the protein coding region(s) and the 5' untranslated and 3' untranslated regions of the mRNA as well any intron regions that may be present. Mutations to a gene may be in any region of the gene or a combination of regions and might extend from altering only one nucleotide, for example a frameshift mutation in the coding region, to deletion of the entire gene. Plants which are homozygous for the genetic variation are preferred.

Deletions may be restricted in size in the order of one or a few hundred, perhaps 500, kilobases. In certain embodiments, the deletion extends to less than a few thousand kilobases, or less than 5 thousand kilobases. Whilst the invention may encompass larger deletions including much of the long arm of chromosome 2 of the respective genome these are not preferred because the long arm of chromosome 2 has a number of other genes localised thereon that impact on the vigour of the wheat plant. Accordingly, where large deletions occur, these impact adversely on the vigour of the plant and hence on its commercial viability, and it is desired that at least a majority of the long arm of chromosome 2 is present. In a preferred embodiment, the majority of the long arm of chromosome 2A is present.

Mutagenesis can be achieved by chemical or radiation means, for example EMS or sodium azide (Zwar and Chandler, 1995) treatment of seed, or gamma irradiation. Isolation of mutants may be achieved by screening mutagenised plants or seed. For example, a mutagenized population of wheat may be screened for high amylose content in the grain and/or longer than normal amylopectin chain length distribution, or loss of the SBEIIa protein by ELISA, or for altered grain morphology (Green et al., 1997). Screening is preferably done in a wheat genotype that already lacks one of the SBE activities, for example in a SBEIIb-negative background. Alternatively, the mutation may be identified using techniques such as "tilling" in a population mutagenised with an agent such as EMS (Slade et al, 2005). Such mutations may then be introduced into desirable genetic backgrounds by crossing the mutant with a plant of the desired genetic background and performing a suitable number of backcrosses to cross out the originally undesired parent background.

In another embodiment, the mutation affects the expression or activity of both SBEIIa and SBEIIb genes in wheat. Identifying such a mutation is aided by the unexpected finding that the two genes are closely linked in wheat, in contrast to maize or rice. Deletions in one gene may readily extend to the other gene, providing a null allele (null mutation) for both genes. This knowledge also aids the screening of natural variants that are mutant in both genes on at least one genome of wheat, and more readily allows screening to produce wheat with combined mutations in both genes in two or three genomes. Such wheat provides a high amylose, non-transgenic source of wheat grain and products therefrom.

Mutations in the genes encoding the SBEIIa or other enzymes involved in amylopectin synthesis will generally cause an increased proportion of amylose content. The amount of amylose per individual grain may be increased as a consequence of diverted carbon flow from amylopectin to amylose, or it may be decreased if there is a significant decrease in starch production per grain. In either case, the relative level of amylose as a percentage of starch increases.

Seed with starch granules having a distorted shape have been reported in high amylose barley (Morell et al, 2003) and in low amylopectin (LAPS) maize having about 90% amylose in starch (Sidebottom et al., 1998).

Birefringence is the ability of a substance to refract light in two directions; this produces a dark cross called a "maltese cross" on each starch granule when viewed with a polarizing microscope. Birefringence is an indicator of the degree of ordered structural organization of the polymers within the granules (Thomas and Atwell, 1999). Loss of birefringence in starch granules is generally well correlated with increased amylose content.

It will be understood that whilst various indications have been given as to aspects of the present invention, the invention may reside in combinations of two or more aspects of the present invention.

EXAMPLES

Example 1

Materials and Methods

Carbohydrate Determination and Analysis

Starch was isolated from wheat grain using the method of Schulman et al. (1991). Starch content was determined using the total starch analysis kit supplied by Megazyme (Bray, Co Wicklow, Republic of Ireland).

The amylose content of starch samples was determined by the colorimetric (iodometric) method of Morrison and Laignelet (1983) with slight modifications as follows. Approximately 2 mg of starch was weighed accurately (to 0.1 mg) into a 2 ml screw-capped tube fitted with a rubber washer in the lid. To remove lipid, 1 ml of 85% (v/v) methanol was mixed with the starch and the tube heated in a 65° C. water bath for 1 hour with occasional vortexing. After centrifugation at 13,000 g for 5 min, the supernatant was carefully removed and the extraction steps repeated. The starch was then dried at 65° C. for 1 hour and dissolved in urea-dimethyl sulphoxide solution (UDMSO; 9 volumes of dimethyl sulphoxide to 1 volume of 6 M urea), using 1 ml of UDMSO per 2 mg of starch (weighed as above). The mixture was immediately vortexed vigorously and incubated in a 95° C. water bath for 1 hour with intermittent vortexing for complete dissolution of the starch. An aliquot of the starch-UDMSO solution (50 µl) was treated with 20 µl of $I_2$-KI reagent that contained 2 mg iodine and 20 mg potassium iodide per ml of water. The mixture was made up to 1 ml with water. The absorbance of the mixture at 650 nm was measured by transferring 200 µl to microplate and reading the absorbance using an Emax Precision Microplate Reader (Molecular Devices, USA). Standard samples containing from 0 to 100% amylose and 100% to 0% amylopectin were made from potato amylose and corn (or potato) amylopectin (Sigma) and treated as for the test samples. The amylose content (percentage amylose) was determined from the absorbance values using a regression equation derived from the absorbances for the standard samples. Analysis of the amylose/amylopectin ratio of non-debranched starches may also be carried out according to Case et al., (1998) or by an HPLC method for separating debranched starches as described by Batey and Curtin (1996).

The distribution of chain lengths in the starch was analysed by fluorophore assisted carbohydrate electrophoresis (FACE) using a capillary electrophoresis unit according to Morell et al (1998), after debranching of the starch samples. The gelatinisation temperature profiles of starch samples may be measured in a Pyris 1 differential scanning calorimeter (Perkin Elmer, Norwalk Conn., USA). The viscosity of starch solutions may be measured on a Rapid-Visco-Analyser (RVA, Newport Scientific Pty Ltd, Warriewood, Sydney), for example using conditions as reported by Batey et al., 1997. The parameters that may be measured include peak viscosity (the maximum hot paste viscosity), holding strength, final viscosity and pasting temperature. The swelling volume of flour or starch may be determined according to the method of Konik-Rose et al (2001). The uptake of water is measured by weighing the sample prior to and after mixing the flour or starch sample in water at defined temperatures and following collection of the gelatinized material.

Enzyme Assay

Total starch synthase activity in endosperm may be measured by extraction of proteins and assay by the methods described in Libessart et al. (19995) or Cao et al. (1999). The assays use $^{14}C$ labeled ADPG substrate and measure incorporation of the monomer into starch polymers. Individual isoforms of starch synthase in extracts may be separated by gel electrophoresis and assayed in-gel (zymogram) as follows. Extracts from developing seeds may be prepared using 50 mM potassium phosphate buffer, pH7.5, 5 mM EDTA, 20% glycerol, 10 µM Pefabloc and 0.05 mM dithiothreitol (DTT). After grinding the seeds to a pulp in the buffer, the mixture is centrifuged at 14,000 g for 15 min at 4° C. and the supernatant drawn off. The protein concentration in the supernatant may be measured using Coomassie Protein Reagent or other standard means. Storage of the extracts is at −80° C. if the protein extracts are to be run on native gels. For denaturing gel electrophoresis, 100 µl of extract is mixed with SDS and β-mercaptoethanol and the mixtures are incubated in boiling water for 4 min to denature the proteins. Electrophoresis is carried out in standard denaturing polyacrylamide gels using 8% polyacrylamide separating gels overlaid with 4.5% polyacrylamide stacking gels. After electophoresis, the proteins may be renatured by soaking the gels in 40 mM Tris-HCl buffers for a minimum of 2 hr, changing the buffer every 30 min and using at least 100 mL of buffer for each buffer change. For non-denaturing gels, the denaturing step with SDS and β-mercaptoethanol is omitted and SDS omitted from the gels. A starch synthase assay buffer including Tris-glycine (25 mM Tris, 0.19M glycine), 0.133M ammonium sulphate, 10 mM $MgCl_2$, 670 µg/mL BSA and 1 mM ADPG substrate may be used to detect starch synthase bands, followed by staining with 2% KI, 0.2% $I_2$ iodine solution to detect the starch product.

Alternatively, starch synthase or other starch biosynthetic enzymes may be detected in extracts from seeds using specific antibodies (ELISA).

Example 2

Genetic Constructs for the Alteration of Wheat SBEIIa and SBEIIb Expression

Duplex-RNA (dsRNA) constructs were made to reduce the expression of either the SBEIIa or SBEIIb genes of wheat. In such constructs, the desired nucleic acid sequence corresponding to part of the SBEIIa or SBEIIb genes occurred in both the sense and antisense orientations relative to the promoter so that the expressed RNA comprised complementary regions that were able to basepair and form a duplex or double-stranded RNA. A spacer region between the sense and antisense sequences comprised an intron sequence which, when transcribed as part of the RNA in the transformed plant, would be spliced out to form a tight "hairpin" duplex structure. The inclusion of an intron has been found to increase the efficiency of gene silencing conferred by duplex-RNA constructs (Smith et al, 2000). The desired nucleic acid was linked to a high molecular weight glutenin (HMWG) promoter sequence (promoter of the Dx5 subunit gene, Accession No. X12928, Anderson et al., 1989) and terminator sequence from the nopaline synthase gene from *Agrobacterium* (nos3'). This provided endosperm specific expression of the dsRNA sequences.

The SBEIIa duplex-RNA construct contained 1536 bp of nucleotide sequence amplified by PCR from the wheat SBEIIa gene (GenBank Accession number AF338431, see FIG. 1). This included a 468 bp sequence that comprised the whole of exons 1 and 2 and part of exon 3 (nucleotide positions 1058 to 1336, 1664 to 1761 and 2038 to 2219 in FIG. 1), with EcoRI and KpnI restriction sites on either side (fragment 1), a 512 bp sequence consisting of part of exons 3 and 4 and the whole of intron 3 of SBEIIa (nucleotide positions 2220 to 2731 in FIG. 1) with KpnI and SacI sites on either side (fragment 2) and a 528 bp fragment consisting of the complete exons 1, 2 and 3 of SBEIIa (nucleotide positions 1058 to 1336, 1664 to 1761 and 2038 to 2279 in FIG. 1) with BamHI and SacI sites on either side (fragment 3). Fragments 1, 2 and 3 were then ligated so that the sequence of fragment 3 was ligated to fragment 2 in the antisense orientation relative to fragment 1. The duplex-RNA constructs were initially generated in the vector pDVO3000 which contains the HMWG promoter sequence and nos3' terminator. The gene construct in the vector pDVO3000 was designated pDVO3-IIa and the duplex-RNA gene designated ds-SBEIIa.

The strategy for the SBEIIb duplex-RNA construct was similar. The SBEIIb construct contained a fragment of 1607 bp amplified by PCR from the wheat SBEIIb gene (sequence is outlined in FIG. 2). This included a 471 bp sequence that comprised the whole of exons 1 and 2 and part of exon 3 (nucleotide positions 489 to 640, 789 to 934 and 1598 to 1769 in FIG. 2), with EcoRI and KpnI restriction sites on either side (fragment I), a 589 bp sequence consisting of part of exons 3 and 4 and the whole of intron 3 of SBEIIb (nucleotide positions 1770 to 2364 in FIG. 2) with KpnI and SacI sites on either side (fragment 2) and a 528 bp fragment consisting of the complete exons 1, 2 and 3 of SBEIIb (nucleotide positions 489 to 640, 789 to 934 and 1598 to 1827 in FIG. 2) with BamHI and SacI sites on either side (fragment 3). Fragments 1, 2 and 3 were then ligated so that the sequence of fragment 3 was ligated to fragment 2 in the antisense orientation relative to fragment 1. The SBEIIb duplex-RNA gene construct in the vector pDVO3000 was designated pDVO3-IIb and the duplex-RNA gene designated ds-SBEIIb. The constructs are shown schematically in FIG. 3.

Each of the ds-RNA expression cassettes was then cut out with the restriction enzyme XhoI and inserted into the binary transformation vectors pGB53 and pBIOS340. pGB53 was created from pSB11 (Komari et al., 1996) by the introduction of the gene encoding asulam resistance (sul) driven by the rice actin promoter, leaving a unique XhoI site adjacent to the right T-DNA border for the introduction of a gene of interest. Similarly, pBIOS340 was created from pSB1 (Komari et al., 1996) by the introduction of an nptII gene encoding kanamycin and geneticin resistance, driven by the rice actin promoter, again leaving a unique XhoI site adjacent to the right border. The SBEIIa constructs in pGB53 and pBIOS340 were designated pCL51 and pCL59, respectively, and the SBEIIb constructs in pGB53 and pBIOS340 were designated pCL54 and pCL60, respectively.

Example 3

Transformation of Wheat

Genetic constructs for transformation of wheat were introduced by electroporation into the disarmed *Agrobacterium tumefaciens* strain LBA4404 carrying the vir plasmid pAL4-404 and pSB1, with subsequent selection on media with spectinomycin. Transformed *Agrobacterium* strains were incubated on solidified YEP media at 27° C. for 2 days. Bacteria were then collected and re-suspended in TSIM1 (MS media with 100 mg/l myo-inositol, 10 g/l glucose, 50 mg/l MES buffer pH5.5) containing 400 mM acetosyringone to an optical density of 2.4 at 650 nm for wheat inoculation.

Wheat plants (variety NB1, a Spring wheat variety obtained from Nickerson Seeds Ltd, Rothwell, Lincs.) were grown in a glasshouse at 22/15° C. day/night temperature with supplemented light to give a 16 hour day. Tillers were harvested approximately 14 days post-anthesis (embryos approximately 1 mm in length) to include 50 cm tiller stem. All leaves were then removed from the tillers except the flag leaf, which was cleaned to remove contaminating fungal spores. The glumes of each spikelet and the lemma from the first two florets were then carefully removed to expose the immature seed. Generally, only these two seed in each spikelet were uncovered. This procedure was carried out along the entire length of the inflorescence. The ears were then sprayed with 70% IMS as a brief surface sterilization.

*Agrobacterium* suspensions (1 µl) were inoculated using a 10 µl Hamilton syringe into the immature seed approximately at the position of the scutellum:endosperm interface so that all exposed seed were inoculated. The tillers were then placed in water, covered with a translucent plastic bag to prevent seed dehydration, and placed in a lit incubator for 3 days at 23° C., 16 hr day, 45 µEm$^{-2}$s$^{-1}$PAR. After 3 days of co-cultivation, the inoculated immature seed were removed and surface sterilized with 70% ethanol (30 sec), then 20% bleach (Domestos, 20 min), followed by thorough washing in sterile distilled water. Immature embryos were aseptically isolated and placed on W3 media (MS supplemented with 20 g/l sucrose and 2 mg/l 2,4-D and solidified with 6 g/l Type I agarose, Sigma) with the addition of 150 mg/l Timentin (W3T) and with the scutellum uppermost (20 embryos per plate). Cultures were placed at 25° C. in the light (16 hour day, 80 µEm$^{-2}$s$^{-1}$PAR). The development of the embryonic axis on the embryos was assessed about 5 days after isolation and the axis was removed where necessary to improve callus production. The embryos were maintained on W3T for 4 weeks, with a transfer to fresh media at 2 weeks post-isolation and assessed for embryogenic capacity.

After 4 weeks growth, callus derived from the inoculated embryos was very similar to control callus obtained from uninoculated embryos plated on W3T medium. Presence of the bacteria did not appear to have substantially reduced the embryogenic capacity of the callus derived from the inoculated embryos. Embryogenic calli were transferred to W3 media with 2 mg/l Asulam (where pGB53 derivatives were used) or geneticin at 25 mg/l (pBIOS340 derivatives) and 150 mg/l Timentin (W32AT). Calli were maintained on this media for a further 2 weeks and then each callus was divided into 2 mm-sized pieces and re-plated onto W32AT. Control embryos derived from inoculations with the LBA4404 without binary vector constructs did not produce transformed callus on selection media.

After a further 2 weeks culture, all tissue was assessed for development of embryogenic callus: any callus showing signs of continued development after 4 weeks on selection was transferred to regeneration media (RMT-MS with 40 g/l maltose and 150 mg/l Timentin, pH 5.8, solidified with 6 g/l agarose, Sigma type 1). Shoots were regenerated within 4 weeks on this media and then transferred to MS30 with 150 mg/l Timentin for shoot elongation and rooting. Juvenile plants were then transferred to soil mixture and kept on a misting bench for two weeks and finally transferred to a glasshouse.

A total of 3217 embryos using pCL54 or pCL60 (ds-SBEIIb) and 2010 embryos using pCL51 or pCL59 (ds-SBEIIa) were treated by this method and 61 plants were regenerated from calli for the IIb transformation and 31 plants regenerated from calli for the IIa transformation. Survival on selection medium suggested that they were successfully transformed with the gene construct. A large majority, but not all, of the plants that were transformed with the selectable marker gene would be expected to integrate the SBEIIa or SBEIIb inhibitory gene; these could readily be distinguished as described in the following examples.

The recovery of multiple, stable integration events with good regeneration potential from the experiments indicated that the seed inoculation transformation method used here was as efficient as other reported methods for wheat. Alternative *Agrobacterium* strains such as strain AGL1 or selectable markers such as genes encoding hygromycin resistance can also be used in the method.

Example 4

Analysis of Wheat Transformants

Transformation was determined by one or more of the following methods:

PCR analysis for one or more of the transgenes. PCR analysis was performed on genomic DNA extracted from 1-2 $cm^2$ of fresh leaf material using the mini-prep method described by Stacey and Isaac (1994). PCR reactions were performed, for example, using the primers SBEIIa-For: 5'-CCCGCTGCTTTCGCTCATTTTG-3' [SEQ ID NO. 4] and SBEIIa-Rev: 5'-GACTACCGGAGCTCCCACCTTC-3' [SEQ ED NO. 5] designed to amplify a fragment (462 bp) from the SBEIIa gene, or SBEIIb-DupFor 5'-AGATGT-GAATGGCTGCTTGCTG-3' [SEQ ID NO. 6] and SBEIIb-DupRev 5'-CAGGTCGACCATATGGGAGAGC-3' [SEQ ID NO. 7] for SBEIIb (505 bp). Reaction conditions were as follows: "hot start" (94° C., 3 min) followed by 30 cycles of denaturation (95° C., 30 sec), annealing (55° C., 30 sec), extension (73° C., 2 min) followed by 1 cycle at 73° C. (5 min).

Southern blot hybridization analysis was performed on DNA from a larger scale (9 ml) extraction from lyophilized ground tissue (Stacey and Isaac, 1994). DNA samples were adjusted to 0.2 mg/ml and digested with restriction enzymes such as HindIII, EcoRI and KpnI. Restriction enzyme digestion, gel electrophoresis and vacuum blotting were carried out as described by Stacey and Isaac (1994). Digoxygenin-labelled probes including the intron 3 region of the ds-SBEII constructs were produced by PCR according to the method of McCreery and Helentjaris (1994). Hybridization of the probes to the Southern blot and detection by chemiluminescence were performed according to the method of McCreery and Helentjaris (1994).

The results of the PCR analyses are summarized in Table 2. Plants that were positive for the transgenes as demonstrated by PCR included 27 independent transformation events for ds-SBEIIa and 61 independent events for ds-SBEIIb.

TABLE 2

Transformation of wheat with SBEIIa and SBEIIb RNA duplex constructs.

| Experiment No. | No. of embryos inoculated | No. of lines regenerated | PCR positive lines |
|---|---|---|---|
| ds-SBEIIa construct ||||
| 44 | 242 | 1 | 1 |
| 50 | 169 | 3 | 3 |
| 52 | 158 | 3 | 3 |
| 58 | 163 | 2 | 2 |
| 61 | 195 | 1 | 1 |
| 72 | 185 | 1 | 0 |
| 83 | 241 | 1 | 1 |
| 84 | 242 | 1 | 1 |
| 85 | 153 | 5 | 5 |
| 109 | 262 | 13 | 10 |
| Total | 2010 | 31 | 27 |
| ds-SBEIIb construct ||||
| 48 | 291 | 1 | 1 |
| 51 | 166 | 1 | 0 |
| 53 | 194 | 1 | 0 |
| 55 | 261 | 1 | 1 |
| 59 | 253 | 1 | 0 |
| 60 | 175 | 4 | 2 |
| 62 | 199 | 1 | 0 |
| 70 | 152 | 1 | 0 |
| 73 | 238 | 2 | 2 |
| 75 | 151 | 2 | 2 |
| 76 | 150 | 1 | 0 |
| 77 | 150 | 2 | 2 |
| 81 | 134 | 1 | 1 |
| 87 | 230 | 5 | 3 |
| 92 | 233 | 8 | 5 |
| 110 | 240 | 29 | 16 |
| Total | 3217 | 61 | 35 |

Example 5

Analysis of Grain from Plants Transformed with Duplex-RNA Constructs

Starch Granule Morphology.

The morphology of starch granules from mature T1 seed obtained from the T0 transformed wheat plants was observed by light microscopy. Ten individual grains from each of 25 T0 plants independently transformed with ds-SBEIIa and 12 plants independently transformed with ds-SBEIIb were analysed. Each endosperm was gently crushed to release the starch granules, which were dispersed in water and visualized under a light microscope. Of the 25 ds-SBEIIa lines analysed, 12 had grains with distorted granules although the visual observation revealed varying levels of distortion in different seeds. In contrast, none of the 12 ds-SBEIIb lines showed significant starch granule distortion in the endosperm when observed under light microscopy.

Observing the starch granules under polarized light revealed that there was a significant reduction in birefringence for distorted granules for the ds-SBEIIa grain. Loss of birefringence was observed for 94% of the granules in seeds from the line 50.1b, correlating with their distorted phenotype, while normal granules from another seed of the same line showed full birefringence. The seed with normal granules is presumed to be a segregant lacking the transgene and therefore phenotypically normal.

Light microscopy results were confirmed by scanning electron microscopy (SEM) of the starch granules. To do this, purified starch is sputtered with gold and scanned at 15 kV at room temperature.

Grain Weight

Individual grains from ds-SBEIIa transformed plants, grown under equivalent conditions in the greenhouse, were weighed (Table 3). Grains having severely distorted granules from plants 50.1b, 58.2a, 61.2a and 109 were not significantly reduced in average weight compared to grains of wild-type plants grown under the same conditions. Therefore, starch production did not appear to be substantially reduced even in the seeds with highly distorted starch granules. This data also suggests that the yield of field-grown wheat with reduced SBEIIa activity in the endosperm is about normal.

TABLE 3

Grain weight of T1 seeds from the ds-SBEIIa transgenic wheat lines

| Trans-genic Line | Seed No | Seed weight (mg) | Starch granule morphology* | Trans-genic Line | Seed No | Seed weight (mg) | Starch granule morphology* |
|---|---|---|---|---|---|---|---|
| 50.1b | 1 | 16.9 | + | 61.2a | 1 | 50.7 | + |
|  | 2 | 49.8 | + |  | 2 | 49.0 | +/− |
|  | 3 | 46.9 | − |  | 3 | 49.8 | − |
|  | 4 | 50.0 | − |  | 4 | 47.0 | − |
|  | 5 | 45.4 | − |  | 5 | 48.6 | − |
|  | 6 | 42.6 | − |  | 6 | 46.2 | − |
|  | 7 | 39.9 | +/− |  | 7 | 42.2 | + |
|  | 8 | 41.0 | + |  | 8 | 50.4 | − |
|  | 9 | 39.5 | − |  | 9 | 39.7 | − |
|  | 10 | 37.0 | +/− |  | 10 | 46.3 | − |
| 58.2a | 1 | 44.0 | − | 109.7b | 1 | 40.1 | − |
|  | 2 | 37.4 | + |  | 2 | 34.6 | − |
|  | 3 | 48.8 | − |  | 3 | 43.7 | − |
|  | 4 | 43.2 | + |  | 4 | 38.8 | − |
|  | 5 | 46.2 | − |  | 5 | 33.8 | +/− |
|  | 6 | 42.1 | + |  | 6 | 31.1 | +/− |
|  | 7 | 43.5 | +/− |  | 7 | 35.9 | + |
|  | 8 | 45.7 | − |  | 8 | 44.3 | +/− |
|  | 9 | 38.8 | − |  | 9 | 37.7 | − |
|  | 10 | 38.1 | +/− |  | 10 | 41.4 | − |

+ normal starch granules,
− severely distorted granules,
+/− mild distortion of granules Analysis of SBEIIa and SBEIIb Proteins in T2 Transgenic Wheat Endosperm.

Seed (T2) from 13 ds-SBEIIa transformed T1 plants, representing 5 independently transformed lines, and from 9 ds-SBEIIa transformed plants, representing 3 independently transformed lines, were analysed for SBEIIa and SBEIIb protein expression in endosperm by non denaturing PAGE and Western blotting. The ds-SBEIIa plants were all from lines having abnormal starch granule morphology, while the ds-SBEIIb lines all had normal granule morphology, as described above. The antibody used for detection of SBEIIa was 3KLH, from rabbits, which had been raised against the synthetic peptide having the amino acid sequence AASPGKVLVPDESDDLGC [SEQ ID NO. 8], corresponding to the sequence from the N-terminus of mature SBEIIa, and was diluted 1:5000 for use. The antibody used for detection of SBEIIb was R6, raised against the synthetic peptide having the amino acid sequence AGGPSGEVMIGC [SEQ ID NO. 9], corresponding to the deduced sequence from the N-terminus of mature SBEIIb and diluted 1:6000 before use. The secondary antibody used was GAR-Horseradish Peroxidase conjugate (1:3000 dilution). Immunoreactive bands were revealed using an Amersham ECL-detection system.

Endosperms from each of seven developing grains (15 days post anthesis) from each of the 22 T1 plants were analysed as it was expected that some of the plants would be heterozygous for the transgene. Twelve of the 13 ds-SBEIIa plants produced T2 progeny showing reduced levels of SBEIIa protein in the endosperm. All seven seeds from one line (50.3x.9) appeared to lack SBEIIa entirely, while all seven seeds from four other plants showed obviously reduced expression of SBEIIa. These could represent lines that are homozygous for the transgene. Seven lines were segregating for the absence of SBEIIa or reduced levels of SBEIIa, or in some cases no apparent reduction of the protein, and these lines probably represent heterozygotes for the transgene. The thirteenth line (50.3x.6) was homozygous for wild type expression.

Of the nine ds-SBEIIb transgenic lines tested, three (110.166.2, 110.16b.5 and 110.16b.19) uniformly showed no SBEIIb expression in each of seven progeny seeds, while two were uniform for wild type expression and the remaining four were segregating for no expression, reduced expression or wild-type. Embryos from the seeds may be grown (embryo rescue) to produce T2 plants and T3 seed which are screened by PCR and protein expression analysis to confirm the genetic status of the T2 seed with respect to the transgene.

These data indicate that the duplex-RNA constructs were effective in reducing the expression of the SBEIIa and SBEIIb genes in endosperm of wheat. The data also indicate that reduction of SBEIIb expression alone did not substantially alter starch granule morphology.

The expression of the SBEIIb gene in transgenic seeds containing the ds-SBEIIa transgene and lacking SBEIIa protein, and the expression of the SBEIIa gene in seeds containing the ds-SBEIIb were also analyzed by the Western blot method. Unexpectedly, transgenic seeds comprising ds-SBEIIa were much reduced for SBEIIb. However, the converse effect was not observed in seeds transgenic for ds-SBEIIb. The SBEIIa expression was unaltered in the seeds in which SBEIIb was completely silenced by ds-SBEIIb. It is possible that expression of SBEIIb was suppressed by the ds-SBEIIa construct due to sequence homology between the genes in the region used for the duplex construct, it is also possible that the activity of SBEIIb was reduced by the ds-SBEIIa transgene by some other mechanism.

The expression levels of the SBEIIa and SBEIIb genes can also be specifically determined at the mRNA levels through standard techniques such as Northern hybridisation or RT-PCR methods, for example by using probes from non conserved regions or primer pairs which hybridize to unique sites in one of the genes but not the other, for example in the 3' untranslated regions. Such regions or sites can readily be identified by comparison of the two gene sequences.

Example 6

Starch Analysis of Transformed Wheat

Amylose and Amylopectin Levels in Transgenic Wheat Grain.

The amylose content of starches from six pooled T1 seed samples was determined as described in Example 1. The pooled seed samples were obtained from the transgenic wheat lines as follows:

Pool 1—seed that had distorted starch granules from the ds-SBEIIa transgenic line 85.2c
Pool 2—seed that had normal granules from the ds-SBEIIa transgenic line 85.1a
Pool 3—seed that had normal granules from the ds-SBEIIb transgenic line 110.18a
Pool 4—seed that had distorted granules from the ds-SBEIIa transgenic lines 58.1a, 58.2a and 61.2a, pooled together
Pool 5—seed that had normal granules from the ds-SBEIIa transgenic line 83.1b
Pool 6—seed that had normal granules from the ds-SBEIIb transgenic line 75.3x.

Each analysis was done using four replicates of the starch samples. The regression equation used to convert the absorbance to amylose content for these analyses was Y=57.548x−8.793, where Y was the amylose content (%) and x was the absorbance.

The results are given in the Table below. The presence of distorted starch granules was clearly associated with increased relative amylose contents. Starches from grains with distorted granules from the ds-SBEIIa transgenic lines (pools 1 and 4) had relative amylose contents of greater than 50% while the other starch pools, derived from grain with normal starch granules, had amylose contents in the range 21-26%. This included starch from line IIb 110.18a which had reduced expression of SBEIIb, which suggested that inactivation of SBEIIb alone in wheat did not substantially increase amylose levels in grain starch.

TABLE 4

Amylose content estimated by iodometric method of the transgenic wheat lines

| Starch sample | Transgenic line | Amylose content (%) | | | |
|---|---|---|---|---|---|
| | | Replication 1 | Replication 2 | Replication 3 | Mean |
| Pool 1 | 85.2c | 65.7 | 54.2 | 53.2 | 57.7 |
| Pool 2 | 85.1a | 23.7 | 22.5 | 26.7 | 24.3 |
| Pool 3 | 110.18a | 22.3 | 21.0 | 21.5 | 21.6 |
| Pool 4 | 58.1, 58.2a, 61.2a | 53.9 | 52.8 | 58.5 | 55.1 |
| Pool 5 | 83.1b | 26.5 | 25.3 | 24.8 | 25.6 |
| Pool 6 | 75.3x | 24.3 | 20.6 | 19.5 | 21.5 |

A second set of analyses was done by the iodometric method using a sample from Pool 4 and starch from wheat that was defective in SSII (Yamamori et al. 2000) and from barley line M292 which was mutant in SSIIa. The amylose content determined for starch from Pool 4 wheat seeds (ds-SBEIIa transgenic lines) was considerably higher than that of starch from the SSII mutants of wheat and barley.

This implied that the amylopectin content in the starch of these grains was considerably reduced, from about 75% in wild-type to less than 50% or even less than 20%.

Lines containing both ds-SBEIIa and ds-SBEIIb transgenes were generated by crossing the transgenic plants described above. Relative amylose contents in the grain starch of such progeny were elevated to the same extent compared to starch from plants containing only ds-SBEIIa, in the range of 75 or 80% as measured by Sepharose column methods (Example 8), when the ds-SBEIIa gene was introduced into the F1 plants from the female parent and the ds-SBEIIb gene from the male parent. Lower levels of amylose (55-60%) were observed in F1 progeny from the reciprocal cross. The difference could be due to the triploid nature of the endosperm which contains two copies of the maternal genome and one copy of the paternal genome. This indicated that the copy number of the ds-SBEIIa gene influenced the extent of the elevation in amylose levels, and was consistent with higher amylose levels in homozygotes than heterozygotes.

Discussion

There are three known mechanisms for increasing amylose content in plants: i) to increase GBSS activity, for example, over-expression of GBSS has recently been reported to yield a rice starch with increased amylose content (Itoh et. al., 2003); ii) to decrease amylopectin synthesis by suppression of the activity of starch synthases and isoamylases leading to a net increase in amylose content, for example, amylose contents of 35-45% have been in reported in maize sugary-2, su1 and du-1 (Gao et. al., 1998) and wheat Sgp-1 (Yamamori et al., 2000) mutants, or greater than 70% amylose in a barley variety lacking SSIIa activity (Morell et al., 2003). As shown herein, the third mechanism for increasing amylose content was to suppress the activity of starch branching enzymes, with reduction in SBEIIa and SBEIIb in wheat resulting in starch with an amylose content of >70%, with concomitant changes in starch granule morphology, starch composition, and starch fine structure. This result contrasted with previous findings in maize (Garwood et al., 1976) and rice (Mizuno et al 1993) where reduction in SBEIIb was required for high amylose starch. The results with the hp-SBEIIa construct described above demonstrated that suppression of starch branching enzyme activity in the grain, including at least SBEIIa, provided a high amylose phenotype.

Example 7

Mutation of SBEIIa Gene in Wheat

Mutation of the SBEIIa gene in wheat leading to reduced activity of SBEIIa can be achieved through mutagenesis, for example either gamma ray irradiation or chemical mutagenesis using agents such as ethyl methane sulfonate (EMS). For gamma ray induced mutation, seeds may be irradiated at a dose of 20-50 kR from a $^{60}$Co source (Zikiryaeva and Kasimov, 1972). EMS mutagenesis may be performed by treating the seeds with EMS (0.03%, v/v) as per Mullins et al., (1999). In a B+D double null background, mutant grains may be identified on the basis of increased amylose content or altered starch grain morphology and confirmed by the methods described above. Mutants in SBEIIa that retain SBEIIb activity can be re-mutagenized and the progeny screened for loss of SBEIIb activity in addition to SBEIIa, or the SBEIIa mutant can be crossed with an SBEIIb mutant to combine the mutations and produce a non-transgenic variety of wheat substantially lacking SBEII activity in the endosperm.

In an attempt to identify a wheat line having a mutation in an SBEIIa or SBEIIb gene, 2400 hexaploid wheat accessions were screened for null mutations of SBEIIb in the A, B or D genomes. The primers AR2b19cF/AR2b23cR were used in PCR reactions on genomic DNA samples of wheat plants of each line, followed by digestion of the amplification products with RsaI and gel electrophoresis. This marker amplified the intron 3 region (nucleotide positions 2085 to 2336 in wheat SBEIIb gene, FIG. 2) and was specific for SBEIIb. This screening had resulted in the identification of three D genome SBEII-null mutants and two B genome SBEII-null mutants as described in the Examples above. No mutant lines which lacked the A genome band corresponding to SBEIIb were detected. This suggested that wheat lines comprising chromosome 2A with a mutant SBEIIb gene do not occur naturally.

A gamma ray ($^{60}$Co source) induced mutant wheat population generated by Tony Prior and Rohit Mago (CSIRO) was used to screen for induced mutations in wheat SBEII. The wheat population was generated from the F2 progeny of a cross, Gabo 1BL.1RS×Veery 3. A total of 2694 mutant seeds from this population were screened as described above in PCR reactions with the primers AR2b19cF and AR2b23cR. Two seeds, designated MLT2B8 and MLT2D1, that came from one plant, were identified that lacked the SBEIIb A genome allele. No seeds in the population were identified to contain null mutations of SBEIIb in the B or D genomes.

Since the SBEIIa and SBEIIb genes were closely linked in wheat on the long arm of chromosome 2, DNA from seeds was tested for the presence or absence of the A genome SBEIIa gene with PCR reactions using the primers Sr913F/

E6R. These primers amplify the intron 5 region of wSBEII-D1 (nucleotide positions 2959 to 3189, FIG. 1 [SEQ ID No. 1]). After amplification, the products were electrophoresed on a 5% sequencing gel (ABI Prism DNA sequencer). Fluorescently labeled products were analysed using the software Genescan. The scan profiles showed that the amplification products for both of the mutant seeds MLT2B8 and MLT2D1 lacked the product corresponding to the A genome SBEIIa gene, indicating that both seeds had null alleles for the A genome SBEIIa in addition to SBEIIb.

The null mutations in these seeds were further confirmed by using an A genome specific marker for SBEIIa, ARIIaAF (5'-GCAAAAGCCAGATCATAAATTTAGAGC-3') [SEQ ID NO. 10] and ARIIaAR (5'-CTTCCAATTCATTGT-TAATGGTCACAC-3') [SEQ ID NO. 11] that amplify only the product from A genome SBEIIa gene (nucleotide positions 3024 to 3131 of wSBEII-DA1, FIG. 1). While this pair of primers amplified a 110 bp product from plant material from the variety Chinese Spring, this product was clearly missing in the two putative mutant seeds. This was the same as for the negative control dt2AS, which is a chromosome engineered line of Chinese Spring that is missing the long arm of chromosome 2A. Since the SBEIIa and SBEIIb genes are located on the long arm of chromosome 2, this line lacks the A genome allele of both these genes and hence could be used as a negative control.

Five lines having mutation in both the B and D genome SBEIIa and SBEIIb genes had been generated. Of these, lines such as BD 219 and BD 636 may be crossed to an A null mutant line and a doubled haploid population may be generated from the F1 seeds of these crosses to provide homozygous triple null mutant plants. Such triple null mutant plants should occur in doubled haploid populations at a frequency of 1 in 8. The A genome null mutations can be combined with either the B genome mutations or the D genome mutations by similar crosses. In further crosses, any of the null alleles can be introduced into any suitable genetic background for agronomic or other traits.

Crosses may also be performed to produce durum wheat (such as, for example, variety Wollaroi) having mutations in the A genome or B genome SBEIIa and SBEIIb, or both A and B genome mutations for both genes to produce durum wheat lacking SBEII activity.

Such durum wheat is non-transgenic and has a high amylose phenotype which provides health benefits similar to that of high amylose hexaploid wheat.

Example 8

Confirmation of the High Amylose Content in Grain by Sepharose 2B Column Separation Methods The amylose content of starch in the grain of transgenic wheat plants containing SBEIIa/SBEIIb inhibitory genetic constructs was determined by a Sepharose column separation method. In this method, starch molecules were separated on the column based on their molecular weight. The separated fractions were then assayed using the Starch Assay Kit (Sigma) according to the suppliers instructions.

Approximately 10 mg of starch was dissolved in 3.0 ml of 1N NaOH (de-gassed) by incubation at 37° C. for 30 min. The starch solution was centrifuged for 15 min to spin down the undissolved components. The supernatant was loaded on to a Sepharose CL2B column at a pump speed of 1 ml/min. The column was run using 10 mM NaOH as buffer and fifty fractions of 2.5 ml each were collected. The pH of fractions 9 to 50 was adjusted to 4.5 with 35 µl of 1 M HCl. An aliquot (250 µl) of each sample was transferred into a tube followed by the addition of 250 µl of Starch reagent (Starch assay kit, Sigma). The controls included: a starch assay reagent blank containing only starch reagent (250 µl) and water (250 µl), a glucose assay reagent blank containing only 500 µl water, a sample blank containing only 250 µl starch sample and 250 µl water and a sample test containing only 250 µl starch reagent and 250 µl starch sample. The samples and the controls were incubated at 60° C. for 60 min, and then 200 µl of each transferred to a new tube followed by addition of 1 ml of glucose reagent (starch assay kit, Sigma) and incubation at 37° C. for 30 min. The absorbance at 340 nm was used to determine the quantity of starch (mg) in each fraction according to the instructions supplied with the kit.

The chromatogram of starch samples revealed two peaks eluted from the Sepharose column. The amylose content (second peak) of each sample was calculated as a percentage of the total amount of starch within both of the peaks.

Using this method, the amylose content of the ds-SBEIIa transgenic line Acc. 144087, which was shown to be homozygous for the transgene, was calculated to be 78% and that of a ds-SBEIIb transgenic line Acc 144008 (homozygous transgenic line from the event IIb 110.16b) was estimated to be 23%. In comparison, the iodometric method gave amylose contents for these lines of 88.47% and 27.29%, respectively.

Functional properties such as gelatinization temperature, paste viscosity and starch swelling volume are analysed by Differential Scanning calorimetry (DSC), Rapid Visco Analyser (RVA) and starch swelling power test, respectively. The structure of these starches is analysed by X-ray crystallography and particle size analysis.

TABLE 5

Amylose content of wheat transgenic lines estimated by iodometric method

| Line | Target enzyme | Event No. | Amylose content (%) |
|---|---|---|---|
| NB1 | Non transformed | — | 31.8 |
| 144008 | SBE IIb | IIb 110.16b | 27.3 |
| 144087 | SBE IIa | IIa 85.3a | 88.5 |
| 144025 | SBE IIa | IIa 50.1b | 75.8 |
| LSD | — | — | 7.7 |

Example 9

Chain Length Distribution Analysis

The chain length distribution of starch samples was determined by fluorophore assisted carbohydrate electrophoresis (FACE) after isoamylase de-branching of the starch. The percentages of chain lengths from DP 6-11, DP 12-30 and DP 31-60 in starch from the transgenic seed compared to non-transgenic controls are presented in Table 6.

TABLE 6

Chain length distribution of isoamylase debranched starches from wheat transgenic lines.

| Line | Targeted gene | Event No | DP4-12 | DP13-24 | DP24-36 | >36 |
|---|---|---|---|---|---|---|
| NB1 | Nontransformed control | — | 57.39 | 37.38 | 3.83 | 1.40 |

TABLE 6-continued

Chain length distribution of isoamylase debranched starches from wheat transgenic lines.

| Line | Targeted gene | Event No | DP4-12 | DP13-24 | DP24-36 | >36 |
|---|---|---|---|---|---|---|
| 144087 | SBEIIa | IIa 85.3a | 47.40 | 42.27 | 6.16 | 4.17 |
| 144025 | SBEIIa | IIa 50.1b | 49.99 | 44.40 | 5.60 | — |
| 144008 | SBEIIb | IIb 110.16b | 57.98 | 37.65 | 4.37 | — |

There was a significantly lower proportion of chain lengths of DP 4-12 in starch from ds-SBEIIa transgenic seed compared to starch from untransformed seed or ds-SBEIIb transgenic seed. The proportion of chain lengths of >DP 13 was higher in ds-SBEIIa transgenic seed compared to the others. These results suggest the possibility that SBEIIa is selectively involved in the synthesis of shorter chains of DP 4-12 in wheat starch. In starch from the SSIIa mutant, however, there was an increase in the proportion of shorter chain lengths in the amylose.

Example 10

Properties of Starch from SBEIIa-Modified Wheat

Physical properties of starch from ds-SBEIIa and ds-SBEIIb transgenic lines including the gelatinisation temperature were analysed using a Perkin Elmer Diamond differential scanning calorimeter. Approximately 20 mg of each starch was mixed with water at a ratio of 1:2 i.e. to a moisture content of 66.7%, and sealed in a DSC pan. A heating rate of 10° C. per minute was used to heat the test and reference samples from 0 to 150° C. Data were analysed using the software available with the instrument.

Two endotherm peaks were observed in the thermogram DSC trace for each starch. The first peak represented the breakdown of crystalline structure during gelatinization of starch. The second peak represented the amylose-lipid dissociation endotherm. The gelatinization peak temperature of starch from ds-SBEIIa transgenic lines showed an increase of approximately 7-10° C. compared to the peak temperature for a non-transformed control starch, and approximately 3 to 7° C. increased compared to starch from a ds-SBEIIb transgenic line.

TABLE 7

Thermal properties of transgenic wheat starch measured by differential scanning calorimeter (DSC).

| Lines | Enzyme targeted | Peak 1 (Gelatinisation) | | | | | Peak 2 (Amylose-lipid dissociation) | | | |
|---|---|---|---|---|---|---|---|---|---|---|
| | | Onset | Peak | End | Area | ΔH | Onset | Peak | End | ΔH |
| 008 | SBE IIb | 58.8 | 63.7 | 70.8 | 234.8 | 4.5 | 93.2 | 103.5 | 110.3 | 0.7 |
| 012 | SBE IIb | 59.0 | 64.1 | 70.8 | 262.6 | 4.3 | 94.5 | 103.1 | 109.7 | 0.6 |
| 121 | SBE IIa | 53.7 | 67.5 | 86.9 | 156.4 | 2.6 | 92.4 | 102.9 | 108.9 | 0.7 |
| 087 | SBE IIa | 53.1 | 71.9 | 85.9 | 142.6 | 2.4 | 95.7 | 102.7 | 108.9 | 0.7 |
| 114 | SBE IIa | 53.0 | 68.1 | 88.0 | 125.2 | 2.1 | 92.8 | 102.5 | 109.6 | 0.8 |
| 109c | Control* | 55.9 | 60.7 | 68.8 | 234.3 | 3.9 | 97.2 | 104.6 | 109.9 | 0.4 |

A marked increase in the end temperature of gelatinization (first peak) of approximately 16-19° C. was observed in these lines compared to both non-transformed control and ds-SBEIIb transgenic lines. The temperature of onset of gelatinization appeared to be earlier in ds-SBEIIa transgenic lines than the control or ds-SBEIIb transgenic lines. Ng et al., 1997 reported a gelatinization onset temperature of amylase extender (ae) maize starch similar to that of normal maize starch, but a significant increase in the peak gelatinization temperature in ae starch compared to normal starch. The gelatinization enthalpy of starch from ds-SBEIIa transgenic lines was significantly lower than that of both the control and ds-SBEIIb lines. This seems to be reflecting the significantly lower gelatinization peak area which represents the reduced amount of amylopectin in ds-SBEIIa transgenic lines. No significant alteration was observed in the amylose-lipid dissociation peak in any of the transgenic lines. We have therefore obtained starch with this novel set of properties.

The wheat high amylose starches as described above had structural and functional properties that were similar, but not identical, to high amylose maize starch. Two key differences were noted. Firstly, the increase in peak gelatinisation temperature for high amylose wheat was not as large as the difference observed previously for maize amylose extender starch compared to standard maize. Secondly, there was a reduction in starch content of approximately 30% in amylose extender maize lines (Singletary et al., 1997), however, a suppression of starch content of only 9% was observed for high amylose wheat. Additional increases in amylose content in wheat may be obtained by transferring the hp-SBEIIa and hp-SBEIIb constructs into a SBEI-null background.

Example 11

Animal Trial

Care of Animals.

Young adult, male Sprague Dawley rats were used. They were purchased from the University of Adelaide Animal Resource Facility and housed in groups in standard wire-bottomed cages at the Animal Services Unit of CSIRO Health Sciences and Nutrition in a room of controlled temperature (22±1° C.) and lighting (lights on at 0800-2000 h).

Diets and Feeding

After arrival the rats were adapted to a nonpurified commercial diet for 7 days. They were then weighed and allocated randomly to two dietary treatment groups of six rats each, of equal mean live weight, and transferred to a purified diet. The composition of the basal diet, which was based on AIN 93G (American Institute of Nutrition, 1993) specifications and prepared from standard ingredients, is shown in Table 8. The diets were balanced for macronutrients and comprised 200 g of protein/kg, 550 g of carbohydrate/kg (as 450 g of starch and 100 g of sucrose), 70 g of fat/kg and 90 g of non-starch polysaccharide (NSP) per kg. Processed wheat bran, safflower oil and casein were used to obtain the desired macronutrient profile. Low amylose maize starch was used to ensure uniform starch content (45 g/100 g) for the two diets. The high-amylose wheat diet contained 576 g/kg of the novel (high amylose) wheat as wholemeal flour. Other treatment diets contained between 32% and 48% of the respective wholemeal flour (low-amylose wheat) or starch (low amylose or high amylose maize). Diets may be prepared by blending the various ingredients with a small quantity of water using a planetary mixer. The mixture may then be pelleted (for example to a diameter of 8 mm and a length of 1-2 cm) by extrusion, dried for 16 h at 40° C., and placed in sealed containers and stored at 4° C. Alternatively, as carried out in this experiment, diets were prepared as a powder and freely available, as was drinking water.

TABLE 8

Formulation of the low and high amylose wheat diets

| Ingredient | Low amylose wheat | High amylose wheat |
|---|---|---|
| | (g/kg of diet) | |
| Casein | 113 | 72 |
| Sucrose | 116 | 120 |
| Safflower oil | 44 | 38 |
| Wheat bran | 121 | 65 |
| Low amylose wheat flour | 481 | |
| High amylose wheat flour | | 576 |
| Maize starch* | 83 | 86 |
| Vitamin premix† | 8 | 9 |
| Mineral premix | 29 | 30 |
| Choline | 2 | 2 |
| L-Cysteine | 2 | 2 |

*Conventional (low-amylose) starch (3401C) (Penford Australia Pty Ltd, Lane Cove NSW).
†Pharmamix P169 (Propharma Australia Pty Ltd, Dandenong, Victoria) which contained, per kg mix, 1.5 g retinyl acetate, 25 mg cholecalciferol, 20 g α-tocopherol, 2 g riboflavin, 7.5 mg cyanocobalamin, 5.6 g Ca pantothenate, 50 mg biotin, 10 g nicotinamide, 1 g menadione, 50 g $FeSO_4 \cdot 7H_2O$, 10 g $MnO_2$, 50 g ZnO, 5 g $CuSO_4 \cdot 7H_2O$, 0.25 g $CoSO_4$, 0.5 g KI, 0.1 g $Na_2SeO_4$, and 31 g antioxidant (Oxicap E2; Novus Nutrition, Melbourne Australia).

Rats had unrestricted access to treatment diets and drinking water for 13 days. During the last 9 days, the animals were kept in individual metabolism cages to allow accurate estimation of feed and water intake and total collection of faeces which were retained for analysis. Rats were observed daily and weighed weekly. Diet consumption of rats when housed individually in metabolism cages was recorded daily, as was the weight of faeces.

Feed Intake and Body Weight Gain

Initial body weight did not differ between the groups (overall mean of 193 g; n=12, pooled SE=3). Diets were well accepted and supported rates of food consumption and weight gain (average 6.5 g/d) that were appropriate for rats of this age. There was no effect of dietary treatment on final body weight with a mean of 278 g (SE=7, n=6) and 282 g (SE=6, n=6) for the low and high amylose wheat, respectively. Daily food intake averaged 20 g/d for each of the two groups (P>0.05) during the metabolism cage phase of the study.

Large Bowel Tissue and Digesta Weights

Rats were anaesthetised with halothane, the abdominal cavity opened and the caecal and colonic contents collected, weighed and stored at −20° C. until analysis. The moisture content of caecal digesta was determined by freeze-drying a portion to constant weight, and weighing the portion before and after drying. Data below from the trial are shown as the mean±standard error (SE) for 6 observations per group. They were analysed by t-test and a value of P<0.05 was taken as the criterion of significance.

Large bowel tissue weight was generally greater in rats fed the high amylose wheat but only in the caecum did the effect near significance (P<0.07). In that viscus, the weights were 0.92 g (SE=0.18, n=6) and 1.23 g (SE=0.39, n=6), for the low and high amylose wheats respectively. Thus, the high amylose diet tended to increase tissue mass. The average wet weight of digesta was higher in rats fed the new wheat, tending to be greater in each large intestinal compartment, but the effect was statistically significant only in the caecum where it was more than 2.1-fold higher than in rats fed the low amylose wheat diet (Table 9). Not only did the consumption of the high amylose diet usually result in wetter luminal contents, the dry weight of digesta was still also considerably greater for the high amylose treatment.

TABLE 9

Large bowel digesta weight (g) of rats consuming low or high amylose wheat diets

| Diet | Caecum | Colon | |
|---|---|---|---|
| | | Proximal | Distal |
| Low amylose wheat | 1.47 (0.12)[a] | 0.29 (0.12) | 0.83 (0.17) |
| High amylose wheat | 3.14 (0.34)[a] | 0.48 (0.09) | 1.10 (0.08) |

All values are the mean and standard error (in parentheses) for six animals.
Values in a column with like superscript letters are significantly different:
[a]$P < 0.01$.

Large Bowel SCFA and pH

Digesta and faecal samples were diluted with a specified volume of internal standard (heptanoic acid) for analysis of SCFA and mixed thoroughly for determination of pH using a standard glass electrode. The slurries were then stored frozen to await further analyses. For analysis of total and major individual SCFA, slurries were thawed, centrifuged and concentrated by low temperature vacuum microdistillation for quantification by gas-liquid chromatography (GLC).

Data for the caecum are shown in Tables 10 and 11. The high amylose wheat produced a lower pH value in caecal contents (Table 10). While there were no significant differences in the concentrations of either total or individual short-chain fatty acids (SCFA, Table 10), caecal digesta pools for the total and individual acids were all significantly higher in rats fed the high amylose wheat diet than in controls (Table 11). Faecal total SCFA excretion was also significantly higher (P<0.02) in rats fed the high amylose wheat with a mean value of 46.1 (SE=5) μmol/d compared with 24.7 (SE=5) μmol/d by rats fed the standard wheat.

TABLE 10

Caecal digesta pH and short chain fatty acid concentrations of rats consuming low and high amylose wheat diets

| Diet | pH | Short chain fatty acid concentration (mmol/Kg) | | | |
|---|---|---|---|---|---|
| | | Acetate | Propionate | Butyrate | Total |
| Low amylose wheat | 6.23 (0.05)[a] | 38.6 (1.9) | 11.9 (1.7) | 25.8 (3.3) | 79.6 (3.1) |
| High amylose wheat | 5.90 (0.14)[a] | 43.6 (7.8) | 15.8 (3.1) | 23.0 (2.5) | 84.1 (8.6) |

All values are the mean and SE (in parentheses) for six animals.
Values in any column with like superscript letters are significantly different:
[a]$P < 0.05$.

TABLE 11

Caecal short chain fatty acid pools of rats consuming low and high amylose wheat diets

| Diet | Short chain fatty acid pools (μmol) | | | |
|---|---|---|---|---|
| | Acetate | Propionate | Butyrate | Total |
| Low amylose wheat | 44 (4)$^c$ | 14 (2)$^b$ | 31 (6)$^a$ | 88 (10)$^c$ |
| High amylose wheat | 106 (18)$^c$ | 38 (7)$^b$ | 57 (8)$^a$ | 202 (25)$^c$ |

All values are the mean and SE (in parentheses) for six animals.
Values in any column with like superscript letters are significantly different:
$^a$P < 0.05;
$^b$P < 0.02;
$^c$P < 0.01.

This experiment showed that modified wheat containing high amylose starch induced positive changes in the gastrointestinal tract of a mammalian animal. These changes were consistent with, and could be explained by, the presence of increased levels of resistant starch (RS) in the modified wheat. A key outcome was to confirm that the increased level of amylose translated to desired physiological attributes. Therefore, the modified wheat has the potential to deliver significant health benefits to large numbers of consumers through their diet.

It was observed that food intakes and body weight gain did not differ between the low and high-amylose wheat treatment groups and there was no evidence for any adverse impact on the growth and performance of the animals fed the transgenic high amylose wheat. This was in contrast to a previous report in rats fed a transgenic raw potato starch containing a known toxin, the lectin *Galanthus nivalis* agglutinin (GNA) where a loss of body weight occurred (Ewen and Pusztai, 1999).

Limitations in the quantities of grain meant that the trial described above had to be carried out in rats for a relatively short period of time. Nevertheless, the data show conclusively that indices of large bowel fermentation were all significantly higher in rats fed the high amylose wheat compared with those fed the standard wheat, consistent with an elevated level of RS. Thus large bowel digesta wet weight and SCFA pools and faecal SCFA excretion were all approximately 100% larger in rats fed the modified wheat compared with those fed the control diet. pH values were also significantly lower, again consistent with greater fermentation. That these differences were due to starch, and not NSP, was ensured by balancing the fibre content of the diets. This is of some interest in view of the apparent importance of butyrate in promoting large bowel function Collectively the data support the potential of the high amylose wheat to produce foods high in RS and with a low GI. The data demonstrate the health potential of high amylose wheats, especially in processed foods, as an important additional mechanism to deliver significant health benefits to large numbers of consumers through their diet.

Example 12

Production of Breads

One of the most effective ways of delivering a grain such as high amylose wheat into the diet is through bread. To show that the high amylose wheat could readily be incorporated into breads and to examine the factors that allowed retention of bread making quality, samples of flour were produced, analysed and used in baking. Initially, only small quantities of the high amylose grain were available and therefore dough mixing and baking were carried out on a small scale (10-15 g). Such methods can readily be scaled up to commercial level when sufficient grain is available.

Methods:

Wheat grains were conditioned to 16.5% moisture content overnight and milled with either a Buhler laboratory scale mill at BRI Ltd, Australia, or using a Quadromat Junior mill followed by sieving, to achieve a final particle size of 150 μm. The protein and moisture content of the samples was determined by infrared reflectance (NIR) according to AACC Method 39-11 (1999), or by the Dumas method and air-oven according to AACC Method 44-15A (AACC, 1999).

Micro Z-Arm Miring

Optimum water absorption values of wheat flours were determined with the Micro Z-arm Mixer, using 4 g of test flour per mix (Gras et al 2001; Bekes et al 2002). Constant angular velocity (with shaft speeds for the fast and slow blades of 96 and 64 rpm, respectively) was used during all mixes. Mixing was carried out in triplicate, each for 20 minutes. Before adding water to the flour, the baseline was automatically recorded (30 sec) by mixing only the solid components. The water addition was carried out in one step using an automatic water pump. The following parameters were determined from the individual mixing experiments by taking the averages: WA %—Water Absorption was determined at 500 Brabender Unit (BU) dough consistency; Dough Development Time (DDT): time to peak resistance (sec).

Mixograms

To determine optimal dough mixing parameters with the modified wheat flour, samples with variable water absorption corresponding to water absorption determined by the Micro Z-arm mixer, were mixed in a 10 g CSIRO prototype Mixograph keeping the total dough mass constant. For each of the flour samples, the following parameters were recorded: MT—mixing time (sec); PR—Mixograph peak resistance (Arbitrary Units, AU); BWPR—band width at peak resistance (Arbitrary Units, AU); RBD—resistance breakdown (%); BWBD—bandwidth breakdown (%); TMBW—time to maximum bandwidth (s); and MBW—maximum bandwidth (Arbitrary Units, AU.).

Micro Extension Resting

Dough extensibility parameters may be measured as follows: Doughs may be mixed to peak dough development in a 10 g prototype Mixograph. Extension tests at 1 cm/s may be carried out on a TA.XT2i texture analyser with a modified geometry Kieffer dough & gluten extensibility rig (Mann et al 2003). Dough samples for extension testing (~1.0 g/test) may be moulded with a Kieffer moulder and rested at 30° C. and 90% RH for 45 min. before extension testing. The R_Max and Ext_Rmax may be determined from the data with the help of Exceed Expert software (Smewing, 1995: Mann, 2002).

The recipe used, based on the 14 g flour as 100% was as follows: flour 100%, salt 2%, dry yeast 1.5%, vegetable oil 2%, and improver (ascorbic acid 100 ppm, fungal amylase 15 ppm, xylanase 40 ppm, soy flour 0.3%, obtained from Goodman Fielder Pty Ltd, Australia) 1.5%. The water addition level was based on the micro Z-arm water absorption values that were adjusted for the full formula. Flour (14 g) and the other ingredients were mixed to peak dough development time in a 35 g Mixograph. The moulding and panning were carried out in a two staged proofing steps at 40° C. at 85% RH. Baking was carried out in a Rotel oven for 15 min at 190° C. Loaf volume (determined by the seed (canola) displacement method) and weight measurements were taken after cooling on a rack for 2 hours. Net water loss was measured by weighing the loaves over time.

The flour or wholemeal may be blended with flour or wholemeal from non-modified wheats or other cereals such as barley to provide desired dough and bread-making or nutritional qualities. For example, flour from cvs Chara or Glenlea has a high dough strength while that from cv Janz has a medium dough strength. In particular, the levels of high and low molecular weight glutenin subunits in the flour is positively correlated with dough strength, and further influenced by the nature of the alleles present. In this example, the high amylose wheat flour was blended with flour from the control untransformed line, NB1.

Results.

The water absorption characteristics of the flours obtained from modified wheats were measured (FIG. 4). Blending of the high amylose flour with varying ratios of control flour showed that the high amylose wheat flour had higher water absorbance than the control flour, and this was positively correlated with the level of amylose in the starch—as seen by comparing 50.3x/6/(60.1% amylose) and 85.2c (81.0% amylose). This result may reflect the influence of the altered starch granule size and shape on water absorption characteristics, however, it is also probable that other changes in the high amylose grain such as altered non-starch polysaccharide content may affect water absorption.

Figure 5:
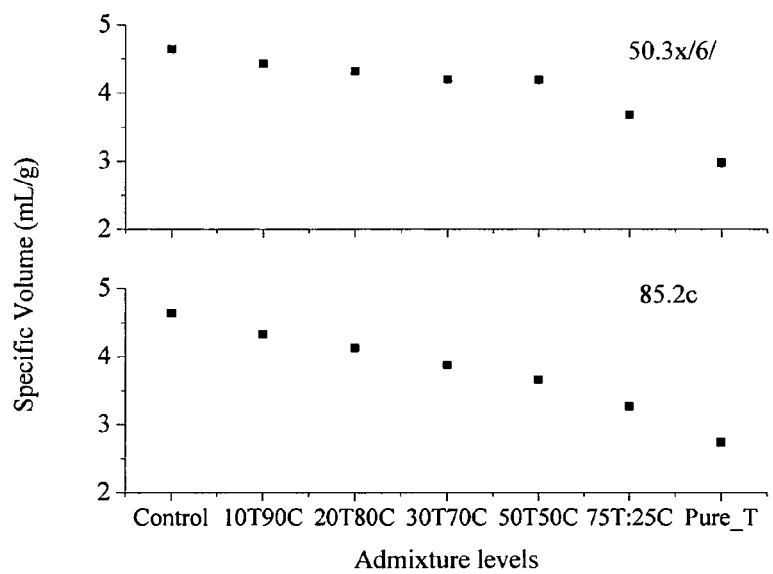
FIG. 5. Specific volume for admixtures of high amylose and control flours, mixed in ratios as indicated.

The specific volumes for admixtures of high amylose and control flours, mixed in ratios from 0:100 to 100:0 was also determined, and the data are shown in FIG. 5. This result shows that the addition of high amylose wheat tended to reduce loaf volume. However, breads containing up to 50% high amylose wheat flour had very acceptable loaf volumes and could be used in standard white bread applications. Breads containing >50% high amylose wheat flour produced loaves have reduced loaf volumes and were suited for heavier style breads such as wholemeal or mixed grain breads. It was thought that further manipulation of improvers, gluten addition, and/or alteration to the genetic background of the wheat variety was likely ameliorate the observed reduction in loaf volume.

Figure 6:
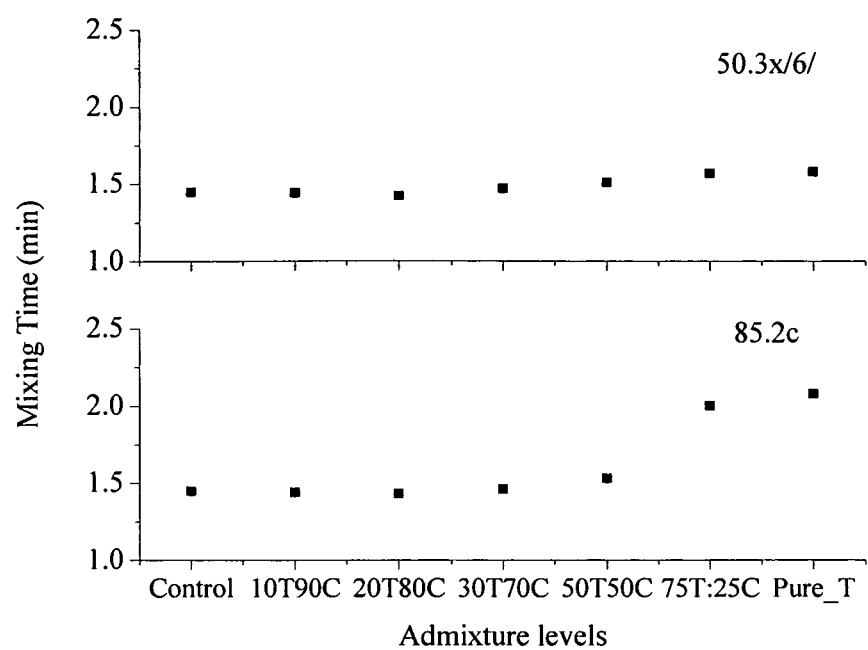
FIG. 6. Mixing time of doughs made from mixtures of high amylose (T) and control (C) wheat flour as determined by Mixograph mixing.

The optimal mixing time of doughs made from mixtures of high amylose and control wheat flour was measured (FIG. 6) and showed that mixing times were within a range considered acceptable for commercial bakery applications.

These studies showed that breads with commercial potential, including acceptable crumb structure, texture and appearance, were obtained using the high amylose wheat flour samples. Furthermore, high amylose wheats may be used in combination with preferred genetic background characteristics (e.g. preferred high and low molecular weight glutenins), the addition of improvers such as gluten, ascorbate or emulsifiers, or the use of differing bread-making styles (e.g. sponge and dough bread-making, sour dough, mixed grain, or wholemeal) to provide a range of products with particular utility and nutritional efficacy for improved bowel and metabolic health.

Example 13

In Vitro Measurements of Glycemic Index (GI) and Resistant Starch (RS) of Food samples The Glycemic Index (GI) of food samples including the bread made as described in Example 12 was measured in vitro as follows:

The food sample was homogenised thoroughly with a Zyliss blender. An amount of sample representing approximately 50 mg of carbohydrate was weighed into a 120 ml plastic sample container and 100 µl of carbonate buffer added without α-amylase. Approximately 15-20 seconds after the addition of carbonate buffer, 5 ml of Pepsin solution (65 mg of pepsin (Sigma) dissolved in 65 ml of HCl 0.02M, pH 2.0, made up on the day of use) was added, and the mixture incubated at 37° C. for 30 minutes in a reciprocating water bath at 70 rpm. Following incubation, the sample was neutralised with 5 ml of NaOH (0.02M) and 25 ml of acetate buffer 0.2M, pH 6 added. 5 ml of enzyme mixture containing 2 mg/mL of pancreatin (α-amylase, Sigma) and 28 U/mL of amyloglucosidase from *Aspergillus niger* (AMG, Sigma) dissolved in Na acetate buffer (sodium acetate buffer, 0.2 M, pH 6.0, containing 0.20 M calcium chloride and 0.49 mM magnesium chloride) was then added, and the mixture incubated for 2-5 minutes. 1 ml of solution was transferred from each flask into a 1.5 ml tube and centrifuged at 3000 rpm for 10 minutes. The supernatant was transferred to a new tube and stored in a freezer. The remainder of each sample was covered with aluminium foil and the containers incubated at 37° C. for 5 hours in a water bath. A further 1 ml of solution was then collected from each flask, centrifuged and the supernatant transferred as carried out previously. This was also stored in a freezer until the absorbances could be read.

All samples were thawed to room temperature and centrifuged at 3000 rpm for 10 minutes. Samples were diluted as necessary (1 in 10 dilution usually sufficient), 10 ul of supernatant transferred from each sample to 96-well microtitre plates in duplicate or triplicate. A standard curve for each microtitre plate was prepared using glucose (0 mg, 0.0625 mg, 0.125 mg, 0.25 mg, 0.5 mg and 1.0 mg). 200 ul of Glucose Trinder reagent (Thermotrace, Noble Park, Victoria) was added to each well and the plates incubated at room temperature for approximately 20 minutes. The absorbance of each sample was measured at 505 nm using a plate reader and the amount of glucose calculated with reference to the standard curve.

The level of Resistant Starch (RS) in food samples including the bread made as described in Example 12 was measured in vitro as follows. This method describes the sample preparation and in vitro digestion of starch in foods, as normally eaten. The method has two sections: firstly, starch in the food was hydrolysed under simulated physiological conditions; secondly, by-products were removed through washing and the residual starch determined after homogenization and drying of the sample. Starch quantitated at the end of the digestion treatment represented the resistant starch content of the food.

On day 1, the food samples were processed in a manner simulating consumption, for example by homogenising with a kitchen chopper to a consistency as would be achieved by chewing. After homogenising, an amount of food representing up to 500 mg of carbohydrate was weighed into a 125 mL Erlenmeyer flask. A carbonate buffer was prepared by dissolving 121 mg of $NaHCO_3$ and 157 mg of KCl in approximately 90 mL purified water, adding 159 µL of 1 M $CaCl_2.6H_2O$ solution and 41 µL of 0.49 M $MgCl_2.6H_2O$, adjusting the pH to 7 to 7.1 with 0.32 M HCl, and adjusting the volume to 100 mL. This buffer was stored at 4° C. for up to five days. An artificial saliva solution containing 250 units of α-amylase (Sigma A-3176 Type VI-B from porcine pancreas) per mL of the carbonate buffer was prepared. An amount of the artificial saliva solution, approximately equal to the weight of food, was added to the flask. About 15-20 sec after adding the saliva, 5 mL of pepsin solution in HCl (1 mg/mL pepsin (Sigma) in 0.02 M HCl, pH 2.0, made up on day of use) was added to each flask. The mixing of the amylase and then pepsin mimicked a human chewing the food before swallowing it. The mixture was incubated at 37° C. for 30 min with shaking at 85 rpm. The mixture was then neutralised with 5 mL of 0.02M NaOH. 25 mL of acetate buffer (0.2

M, pH 6) and 5 mL of pancreatin enzyme mixture containing 2 mg/mL pancreatin (Sigma, porcine pancreas at 4×USP activity) and 28U of amyloglucosidase (AMG, Sigma) from *Aspergillus niger* in acetate buffer, pH6, were added per flask. Each flask was capped with aluminium foil and incubated at 37° C. for 16 hours in a reciprocating water bath set to 85 rpm.

On day 2, the contents of each flask was transferred quantitatively to a 50 mL polypropylene tube and centrifuged at 2000×g for 10 min at room temperature. The supernatants were discarded and each pellet washed three times with 20 mL of water, gently vortexing the tube with each wash to break up the pellet, followed by centrifugation. 50 uL of the last water wash was tested with Glucose Trinder reagent for the absence of free glucose. Each pellet was then resuspended in approximately 6 mL of purified water and homogenised three times for 10 seconds using an Ultra Turrax TP18/10 with an S25N-8G dispersing tool. The contents were quantitatively transferred to a 25 mL volumetric flask and made to volume. The contents were mixed thoroughly and returned to the polypropylene tube. A 5 mL sample of each suspension was transferred to a 25 mL culture tube and immediately shell frozen in liquid nitrogen and freeze dried.

On day 3, total starch in each sample was measured using reagents supplied in the Megazyme Total Starch Procedure kit. Starch standards (Regular Maize Starch, Sigma S-5296) and an assay reagent blank were prepared. Samples, controls and reagent blanks were wet with 0.4 mL of 80% ethanol to aid dispersion, followed by vortexing. Immediately, 2 mL of DMSO was added and solutions mixed by vortexing. The tubes were placed in a boiling water bath for 5 min, and 3 mL of thermostable α-amylase (100 U/ml) in MOPS buffer (pH 7, containing 5 mM $CaCl_2$ and 0.02% sodium azide added immediately. Solutions were incubated in the boiling water bath for a further 12 min, with vortex mixing at 3 min intervals. Tubes were then placed in a 50° C. water bath and 4 mL of sodium acetate buffer (200 mM, pH 4.5, containing 0.02% sodium azide) and 0.1 mL of amyloglucosidase at 300 U/ml added. The mixtures were incubated at 50° C. for 30 min with gentle mixing at 10 min intervals. The volumes were made up to 25 mL in a volumetric flask and mixed well. Aliquots were centrifuged at 2000×g for 10 min. The amount of glucose in 50 μL of supernatant was determined with 1.0 mL of Glucose Trinder reagent and measuring the absorbance at 505 nm after incubation of the tubes at room temperature in the dark for a minimum of 18 min and a maximum of 45 min.

Results

Figure 7:
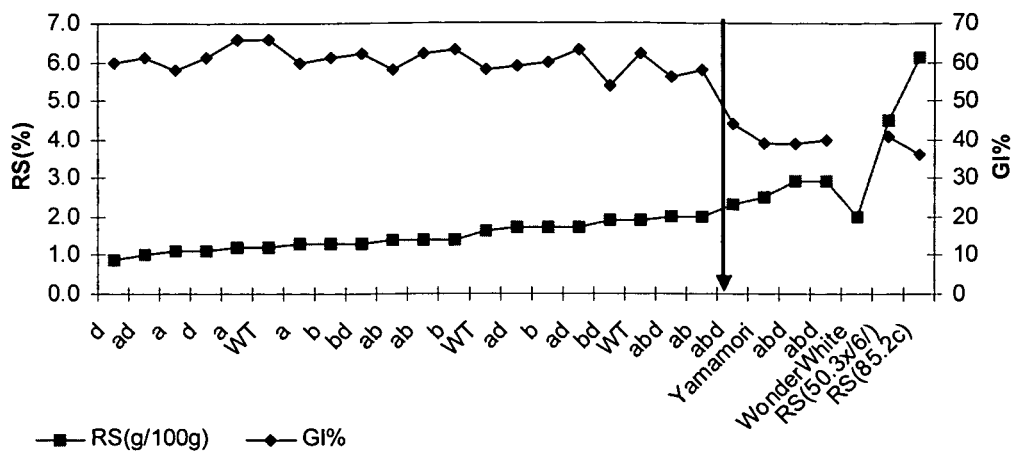
FIG. 7. In vitro Glycemic Index (GI) and Resistant Starch (RS) data for breads made from high amylose (50.3x/6/and 85.2c) modified wheats, or doubled-haploid progeny of a cross between varieties Sunco and an SGP-1 triple null mutant. The progeny were tested for the presence of mutant SGP-1 alleles: lower case letters a, b and d represent the presence of the mutant alleles for SGP-1 on the A, B and D genomes of wheat, respectively. Therefore "abd" represents the triple null allele. "Wonderwhite" represents white bread made with added high amylose maize starch (approximately 10%). Samples to the right of the vertical arrow showed substantially lower GI values (less than 50).
Figure 8:
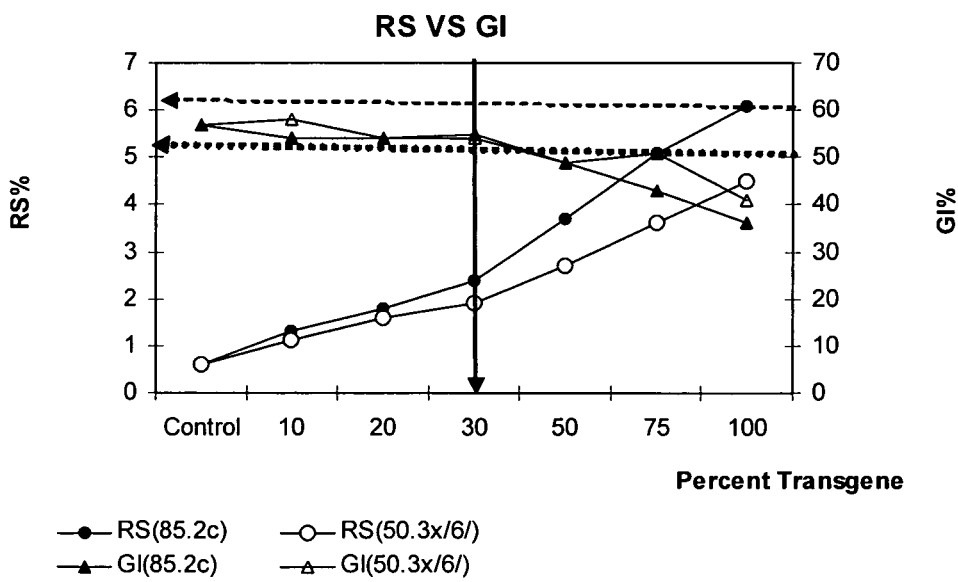
FIG. 8. In vitro GI and RS data for breads made with blended high amylose flour: control flour.

The GI and RS content of breads made with the high amylose wheat flour (>30% amylose (w/w)) were determined. As controls, breads were also made from wheat lines obtained from a cross between varieties Sunco and an SGP-1 triple null mutant (Yamamori et al.). Doubled-haploid plants were obtained from progeny of the cross and grown to provide a population of homozygous lines segregating for the three SGP-1 mutant alleles. The presence of mutant alleles in each line was determined by gene specific (SSIIa gene) PCR reactions on isolated DNA from each line. Thus, the contribution of each of the null alleleles for the SSIIa gene on the A, B and D genomes could be assessed, singly and in each of the possible combinations. Grain from each of the lines was used for bread production by the small-scale method as described above. The results of the in vitro GI and RS measurements are shown in FIGS. 7 and 8.

The GI and RS were also measured for breads made from the high amylose wheat flour blended with control, low amylose flour, using 0%, 10%, 20%, 30%, 50%, 75% or 100% high amylose flour. The data are also presented in FIGS. 7 and 8. The levels of RS increased linearly with increasing amylose content, as the proportion of flour from the high amylose wheat increased. Breads made from flour comprising entirely transgenic high amylose wheat exhibited very high resistant starch levels, with transgenic line 85.2c having substantially higher levels of RS than line 50.3 (6.2 vs 4.5 g RS/100 g bread, respectively). Therefore, replacement of flour from control (low amylose) wheat with the high amylose wheat for production of the bread correlated positively with increased RS.

The levels of RS made with high amylose wheat starch were much higher than in commercially available bread (Wonderwhite) containing high amylose corn starch ("Hi-Maize") used at 10% in the formulation, which had <1% RS. Furthermore, the maximum level of corn starch that can be incorporated in bread without affecting its quality is limited to about 10-12%. Therefore, the use of high amylose wheat in the production of breads provided significant advantages including the level of RS that could be achieved.

The rate of in vitro starch hydrolysis was reduced for the bread made with the modified wheat compared to the bread made with the wild-type wheat. The GI decreased only slightly while the percentage of high amylose wheat flour increased to 30%, but then decreased more rapidly as a greater proportion of high amylose flour was added. The greatest advantage in lowering the GI was seen for food made with at least 50% high amylose wheat flour. Breads made using the higher amylose line 85.2c had a slightly lower GI as measured in vitro than the bread made with line 50.3.

Discussion

The in vitro assays were useful in estimating the quantity of starch in a food product that would be digested or not digested in the small intestine. They yielded values that are thought to accurately and reliably predict the in vivo GI and RS content of foods. Importantly, foods were analysed 'as consumed' which is important considering that food processing methods may have a deleterious lowering effect on the level of RS. In the case of the modified wheat breads, the results demonstrated that physiological functionality (in particular high RS and low GI) had not been destroyed during cooking or storage, and presumably would be present at the point of consumption.

Most processed starchy foods contain very little RS. The breads made using wild-type wheat flour and a conventional formulation and baking process contained <1% RS. In comparison, breads baked using the same process and storage conditions but containing the modified high amylose wheats had levels of RS as much as 10-fold higher. Legumes, which are one of the few rich sources of RS in the human diet, contain levels of RS that are normally <5%. Therefore, consumption of the high amylose wheat bread in amounts normally consumed by adults (e.g. 200 g/d) would readily supply at least 5-12 g of RS. Thus, incorporation of the high amylose wheat into food products has the potential to make a considerable contribution to dietary RS intakes of developed nations, where average daily intakes of RS are estimated to be only about 5 g.

Starch that is resistant to small intestinal digestion enters the large bowel where, largely through its interaction with the microflora, it has a favourable influence on colonic physiology and function.

The rate at which starch is hydrolysed and absorbed in the small intestine determines to a large extent its metabolic properties. The GI ranks foods according to their postprandial glycemic response. Starchy foods that are rapidly digested (high GI) have adverse health consequences, including increased risk of diabetes, obesity and possibly certain cancers. Breads made from the modified wheat flours (transgenic) were shown to have a low GI (<55), particularly when the proportion of modified wheat flour comprised at least 50% of the flour component in the bread formulation. It was possible that components of the modified grains other than starch, such as for example non-starch polysaccharide (NSP) also contributed to the decrease in starch digestibility as measured in vitro. The data suggested that these products made from the altered wheats have potential to reduce the risk of chronic diseases and may be especially helpful in preventing or controlling type-II diabetes by slowing the postprandial rise in blood glucose.

Furthermore, because the starch present in the modified wheats was digested more slowly and less extensively, foods made from these novel wheats had a reduced energy density and may promote satiety. Accordingly, they may be effective in the prevention and management of obesity. They may have applications in the treatment or control of certain diseases and medical conditions e.g. enteral formulations to promote bowel health and function, nutritional products for assisting with blood glucose control in type-I diabetics or those at risk from this disease.

Example 14

Treatment or Prevention of Medical Conditions

Dysglucaemia

In addition to improving bowel health, the invention provides methods and compositions which are thought to be suitable for the promotion of euglycaemia and the treatment, prevention or reduced risk of disordered blood glucose regulation. This is based on the observed reduction in the potential glycemic index of foods incorporating the altered wheat starch. This may be useful in both healthy subjects such as athletes and in compromised individuals such as patients undergoing surgery or chemotherapy. In particular, it may be of great use in diabetic patients seeking to maintain optimal blood glucose levels during the day or night. Blood glucose levels in individuals may be disturbed or altered by exercise, pharmaceutical or surgical therapy, by disease or a syndrome involving multiple diseases or metabolic disorders. Examples include athletes, patients weakened by chemotherapy, fasting patients and patients suffering from disease or disorders disturbing or altering glucose metabolism, or patients undergoing treatment of such and other diseases or disorders. Further examples include animals other than humans such as, for example, pets, livestock or racehorses.

The methods or compositions may be used for improved glycaemic control, that is, for stabilising the blood sugar levels and alleviating the oscillation between unhealthy high and low blood sugar levels. Lack of glycaemic control is associated inter alia with microvascular damage such as occurs in diabetic retinopathy, diabetic ketoacidoses or so called diabetic coma.

A current method of treatment is to use uncooked cornstarch which provides a level of resistant starch. However, it is difficult to prepare compositions of uncooked cornstarch having an agreeable taste and texture, suitable for long-term daily consumption and therefore compliance is affected. Thus, there are advantages in treating diabetic hypoglycaemia by administering the altered wheat starch as described herein, containing resistant starch, as a slow release carbohydrate source for maintenance of acceptable levels of blood glucose in diabetic patients during the night, or at other times when intake of food at short intervals is not possible.

Thus the starch might be administered in a composition that is soluble in the small intestine. Suitable substances included in the composition with the altered wheat starch include polymers such as gum arabica, potassium alginate, guar gum, methyl cellulose, ethyl cellulose, liquid oils, liquid and hard fats and waxes such as paraffin, hydrogenated cottonseed oil, beeswax and carnauba wax.

Uremia

In kidney failure there is a decrease in the glomerular filtration rate and the kidneys are unable to maintain homeostasis of the blood. Retention of water causes oedema and the concentration of hydrogen ions may increase, acidosis may develop, nitrogenous wastes may accumulate and a condition referred to as uremia may develop in the blood and tissues. Examples of uremic toxins include ammonia, urea, creatinine, phenols, indoles, as well as larger molecules. The concentration of serum creatinine, blood urea nitrogen (BUN), uric acid, and guanidino compounds such as N-methyl guanidine (NMG) and guanidino succinic acid (GSA) are significantly altered.

Nitrogenous wastes such as urea, creatinine and uric acid, along with several other small and medium molecular weight compounds, flow into the small intestine and a number of attempts of treatment have been based on the use of the bowel as a substitute for kidney function. A number of absorptive compounds have been used for this purpose, as have locus bean gum. It is also thought that by increasing the fecal bulk and the production of SCFA that a beneficial effect can result. Short chain fatty acids acidify the intestinal content and via osmotic mechanism draw water into the intestinal lumen, providing a laxative effect, prevent overgrowth and facilitate ammonia and other waste nitrogen elemination. They also result in the growth of the fecal biomass, and in doing so, entrap urea and ammonia for bacterial protein synthesis or conversion to the ammonium ion. Through stimulation of bacterial growth and fermentation, prebiotic compounds such as high amylose starches also affect bowel habit and are mildly laxative.

Thus the invention provides altered wheat starch which may be used as a low cost supplement or treatment for renal insufficiency, liver insufficiency, inborn errors of urea metabolism or gastrointestinal disorders or diseases. A ready measure of the effect provided by the altered wheat starch can be determined by ascertaining the levels of serum creatinine.

Example 15

Determination of the Glycemic Index of Foods Made from Modified Wheat

The in vitro digestion and animal feeding trials indicated that food made with the modified wheat starch released glucose relatively slowly during digestion. To establish whether this would also be the case in humans, a feeding trial will be carried out in volunteers to measure the GI of the food and compare it to corresponding food made with wildtype starch. The GI ranks carbohydrate-containing human foods on a weight-for-weight basis according to their postprandial glycemic response. It has considerable clinical and practical utility which is well recognized worldwide. The particular aim of the study is to determine the glycemic index (GI) of two common bakery foods, a bread and muffin, made using modified wholemeal flour. The study will assess the extent to which the modified foods raise blood glucose in volunteers relative to that of a reference carbohydrate and compare this with the GI values for the same type of bakery foods manufactured using standard wheat flour.

A standard wheat and the high amylose wheat will be milled and the resultant wholemeal flour baked into bread and muffins. All foods will be manufactured to industry standards by a commercial manufacturer. The amount of available carbohydrate in representative samples will be determined. The usual method for determining the amount of carbohydrate in foods is 'by difference', i.e. by subtracting the sum of the remaining components (protein, fat, water, ash and fiber) from 100. However, this approach is inherently less reliable than that obtained by direct analysis. Accordingly, we will determine the proximate composition of the test foods using accepted (AOAC) analytical techniques in order to calculate the available carbohydrate of our test foods.

Fourteen subjects will be recruited. GI is calculated using a dataset containing no less than 10 subjects and therefore commencing the trial with an additional 4 volunteers should be sufficient to account for possible withdrawals and the exclusion of outlier values. Prospective volunteers will be informed of the aims, methodology and risks of the trial and be asked to provide written consent.

Volunteers need to be between 16 and 65 years of age, not diabetic or suffering from haemophilia, renal or hepatic disease, not having a known food allergy, hypersensitivity or intolerance to cereal foods (eg celic sprue), are not taking medications known to influence glucose tolerance (oral contraceptives are excluded), and have a fasting blood glucose level between 3.5 and 6.0 mmol/l. In these respects, volunteers are normal and healthy. Persons considered by the investigator to be unwilling, unlikely or unable to comprehend or comply with the study protocol will be excluded, as will those who have participated in another research study within 30 days prior to the commencement of the proposed study. Prospective volunteers will be pre-screened on the basis of their fasting blood glucose levels between 3.5 and 6.0 mmol/l. Subjects whose fasting blood glucose is abnormally high will receive written notification advising them to undergo a glucose tolerance test and to consult their doctor.

Subjects are required to present at the clinic in the fasting state. Subjects are not permitted to consume food or drink, other than water, for a minimum of 10 hours before each test, have no alcohol or legumes on the previous evening, and must not undertake vigorous exercise immediately prior to or during the test. Two blood samples will be taken within 5 minutes of each other and analysed for glucose and the average result shall be taken as the baseline blood glucose concentration. Capillary (finger prick) whole blood will be collected on each occasion.

Specific quantities of the foods will be fed to the volunteers. Four wheat-based foods will be tested: a muffin and bread each made from modified wheat or standard wheat (both as wholemeal flour). The test and reference foods will be fed in random order. Glucose will be the reference food: 50 g of anhydrous glucose powder dissolved in 250 ml of water, and the amount of carbohydrate is exactly equal to that of the test food portion. The reference food is to be tested in each subject three times on separate days within the immediate 3-month period surrounding the testing of the breads and muffins. The test food will contain 50 g of glycemic (available) carbohydrate and volunteers will be instructed to eat the foods within a period of 12 min to 15 min. Subjects shall consume all the test or reference food at an even pace within 12 min to 15 min. They will be given 250 ml of water to consume with the food. During testing, subjects shall rest.

The change in blood glucose concentration over the next two-hours will be monitored according to the standardised protocol for testing the GI, based on the method published by FAO/WHO (1998). Blood samples are taken at 15, 30, 45, 60, 90 and 120 min, starting immediately after the first mouthful of food is taken. Samples are tested in duplicate for glucose. Duplicates should not vary by more than 0.3 mmol/l and additional blood samples may be required so that the CV is <3%. Blood glucose will be determined using a spectrophotometric technique which has an inter-assay co-efficient variation on standard solutions of <3.0%.

GI is determined as the glycemic response, measured as the incremental area under the blood glucose response curve after consumption of a standard amount (usually 50 or 25 g of carbohydrate, in this trial 50 g) of the test food, expressed as a percentage of the average glycemic response (IAUC) to an identical amount of carbohydrate from a reference food (glucose) consumed by the same subject on a separate occasion.

Calculations

The blood glucose response curve (concentration versus time) is plotted and the area under the curve calculated geometrically by applying the trapezoid rule. The area beneath the fasting concentration is ignored in the calculation of GI. Glucose is used as the reference food and by definition has a GI of 100. GI of the test food for an $$\text{individual subject} = \frac{\text{Integrated area of glucose response curve for Test food}}{\text{Integrated area of glucose response curve for Reference}} \times 100$$

GI of the Test Food=Mean GI of $\geq$10 volunteers.

Analysis of variance will be used to determine whether foods made from modified wheat have a significantly lower GI. The wholemeal foods made from the standard wheat are expected to have quite a high GI (>70) whereas the corresponding foods containing modified wheat are expected to register a lower GI, less than or equal to 69, most likely less than 60.

Example 16

Determination of the Resistant Starch Content of Cereal Products in Human Volunteers Resistant starch (RS) is starch which resists upper gut digestion and enters the large bowel. Quantitatively, it is a major source of fermentable substrate for the colonic microflora, which convert starch to metabolites believed critical to the health and metabolic welfare of the large bowel wall. In particular, bacterial fermentation of certain types of resistant starch favour production of SCFA such as butyrate, a major organic acid which is attracting considerable attention because of its capacity to promote programmed cell death and related processes that may protect against colon cancer by eliminating cells that have become dysfunctional.

To test whether the modified wheat having elevated amylose is less susceptible to digestive breakdown in the upper gut, a feeding trial will be carried out in human ileostomy subjects. In particular, the study will accurately determine the resistant starch content of typical foods prepared from high amylose wheat flour. The only effective way to measure resistant starch in foods in humans (in vivo) is to use volunteers with a permanent and well-functioning ileostomy. The ileostomy model technique is widely regarded as a reliable approach for assessing upper gut assimilation of dietary constituents.

The protocol is straightforward and simply involves feeding a number of healthy ileostomists the various test foods made from high amylose wheat or the corresponding low amylose wheat as a control. Recovery of starch and starch hydrolysates from the small bowel will then be determined using a standard analytical technique for total starch.

Volunteers will be recruited from an existing pool of subjects recruited previously or via stomal nurses at local hospitals. Subjects who may be included in the trial are aged 20-80 years, male or female, not receiving any medication likely to modulate small intestinal function or that could interfere with the study in the opinion of the investigator, do not have history of alcohol or drug abuse, have not used any experimental drug within 30 days of commencement of the study, and do not have gastrointestinal, renal, hepatic disease or intestinal inflammation. They must have had minimal terminal ileum removed (<10 cm) and have a conventional and well-functioning permanent ileostomy. They must be willing to comply with alcohol and diet restrictions in the study.

Exclusion criteria include: use of any form of drug therapy or medication or supplements on a regular basis that may interfere with bowel function, definite or suspected personal history or family history of adverse events or intolerance of starchy or other foods, pregnant women or sexually active female subjects able to conceive and practicing inadequate contraception, persons considered by the investigator to be unwilling, unlikely or unable to comprehend or comply with the study protocol and restrictions, persons unwilling or unable to collect ileal effluent as required, and subjects taking any supplements which could interfere with study parameters. Subjects will be asked to provide written consent after being provided with the appropriate information.

At least eight volunteers will be recruited. Statistical calculations reveal that a minimum of 6 subjects are required if there is to be an 80% chance of detecting a 200% increase in ileal starch excretion above baseline ($\alpha=0.05$). Basal starch excretion for day 1 should be about 0.5 g. Consumption of a standard serving portion of a cereal product (~60 g) made from modified cereal and containing 4% resistant starch is expected to yield an additional 2.4 g of starch at the terminal ileum. Therefore, on day 2, it is anticipated that total starch recovery will be in the order of nearly 3 g, a 5-fold increase over baseline.

Before the study commences, volunteers will be given detailed instructions about the study. Volunteers will carry out each study in their own homes. The study consists of a series of three 48-hour feeding trials over a period of 3 weeks. Volunteers will be on a low starch diet for two consecutive days (usually Tuesday and Wednesday) during which they collect the entire contents of their ileostomy bag at specified intervals, as described in detail below. The basal diet will be designed by a dietitian to be low in resistant starch and will be tailored to meet individual needs. Therefore, foods such as wholegrain breads, bananas, breakfast cereals, legumes and other foods that contain resistant starch, other than the test foods, will be avoided. On the second day they are also required to eat one of the test foods. Approximately 50-100 g of the cereal product (about a medium to large serving) will be eaten at 7:30 am on day 2.

Foods to be consumed for the study will be sourced from local supermarkets and delivered to the volunteers prior to the start of each study. Volunteers will prepare their own meals in accordance with detailed instructions. The modified cereal products will be produced by a commercial cereals manufacturer. Fluids (water, tea, coffee, but not alcohol) may be consumed freely by volunteers. Intake of the required foods will be closely monitored during the active phase of the study. Energy and macronutrient intake will be measured during study periods, estimated from food diaries. Meals will be eaten, and ileostomy bags emptied completely and contents collected, according to the following plan:

Day 1. Basal diet.

Contents of ileostomy bag will be collected at 7 am and frozen on dry ice. The foods for the basal diet will be eaten for breakfast (7.30 am), morning tea (10.30 am), lunch (12.30 pm), afternoon tea (3.30 pm) and dinner (6.30 pm). Contents of the ileostomy bag will be collected at two hourly intervals after 7.00 am until 11 pm and frozen.

Day 2. Basal diet plus test food for breakfast. An identical pattern will be followed except that test foods (50-100 g) will be substituted for an equivalent amount of the basal diet.

Day 3. Collection of ileostomy bag contents at 7.00 am.

At each sampling point, volunteers will dispense the entire contents of their ileostomy bags into appropriately labeled containers, which they then seal and place immediately into insulated coolers containing dry ice. Samples will be collected daily from the homes of volunteers and stored frozen (−20° C.) until analysis.

The assays to be carried out on ileal digesta are: output, which is the wet weight of each sample and daily output, moisture content, starch content, maltose content, glucose content, SCFA content and pH. Starch hydrolysates (free glucose & maltose) will be analysed because they originate from starch but have escaped digestion and are therefore a component of the resistant starch fraction.

Short-chain fatty acids and pH provide general information on the metabolic activity microflora of the distal small intestine. Ileal microbial activity in these individuals is a possible source of variation in starch digestibility.

An example of the basal diet is as follows:

| Nutrients (Mean all Days) | | |
|---|---|---|
| Energy: 8595.19 kJ | Carbohydrate: 232.29 g | Starch: 58.65 g |
| Protein: 97.94 g | Dietary Fibre: 19.11 g | |
| Total Fat: 84.06 g | Total Sugars: 168.69 g | |
| | Energy Ratios (Mean all Days) | |
| Protein: 20% Fat: 37% | Carbohydrate: 44% | Alcohol: 0% |
| | Fat Ratios (Mean all Days) | |
| Poly: 12% | Mono: 38% | Saturated: 51% |

| M1 Food/Recipe | Amnt | Measure | Energ kJ | Ptn g | Fat g | Carb g | Fibre g | Sugar g | Stch g |
|---|---|---|---|---|---|---|---|---|---|
| juice, orange, commercial, ns | 100.00 | g | 142 | 1 | 0 | 8 | 0 | 7 | 0 |
| fruit salad, can-pear juice | 200.00 | g | 354 | 1 | 0 | 20 | 3 | 17 | 0 |
| milk, reduced fat, fortified | 200.00 | g | 418 | 8 | 3 | 11 | 0 | 11 | 0 |
| coffee powder, instant | 1.00 | tsp | 4 | 0 | 0 | 0 | 0 | 0 | 0 |
| sugar | 5.00 | g | 84 | 0 | 0 | 5 | 0 | 5 | 0 |
| cheese, cheddar | 20.00 | g | 338 | 5 | 7 | 0 | 0 | 0 | 0 |
| cracker, water | 4.00 | biscuit | 291 | 2 | 2 | 12 | 0 | 0 | 12 |

-continued

| M1 Food/Recipe | Amnt | Measure | Energ kJ | Ptn g | Fat g | Carb g | Fibre g | Sugar g | Stch g |
|---|---|---|---|---|---|---|---|---|---|
| water, plain, drinking | 250.00 | g | 0 | 0 | 0 | 0 | 0 | 0 | 0 |
| croissant | 1.00 | average | 1066 | 6 | 15 | 23 | 2 | 3 | 20 |
| ham, leg, non-canned, lean | 50.00 | g | 226 | 9 | 2 | 0 | 0 | 0 | 0 |
| salad | 50.00 | g | 26 | 0 | 0 | 1 | 1 | 1 | 0 |
| french dressing, commercial | 20.00 | g | 220 | 0 | 5 | 2 | 0 | 2 | 0 |
| custard, commercial | 150.00 | g | 588 | 5 | 4 | 21 | 0 | 17 | 3 |
| apple, stewed, added sugar | 150.00 | g | 513 | 0 | 0 | 31 | 2 | 31 | 0 |
| coffee powder, instant | 1.00 | tsp | 4 | 0 | 0 | 0 | 0 | 0 | 0 |
| biscuit, shortbread | 3.00 | biscuit | 927 | 3 | 11 | 28 | 1 | 9 | 19 |
| milk, reduced fat, fortified | 50.00 | g | 104 | 2 | 1 | 3 | 0 | 3 | 0 |
| sugar | 5.00 | g | 84 | 0 | 0 | 5 | 0 | 5 | 0 |
| chicken, breast, raw, lean | 200.00 | g | 938 | 45 | 5 | 0 | 0 | 0 | 0 |
| carrot, mature, peeled, boiled | 100.00 | g | 112 | 1 | 0 | 6 | 4 | 6 | 0 |
| broccoli, frozen, boiled | 50.00 | g | 46 | 1 | 0 | 1 | 2 | 1 | 0 |
| oil, canola | 10.00 | g | 370 | 0 | 10 | 0 | 0 | 0 | 0 |
| ice cream, vanilla | 50.00 | g | 400 | 2 | 6 | 10 | 0 | 10 | 0 |
| apricot, can-pear juice | 150.00 | g | 266 | 1 | 0 | 14 | 3 | 12 | 0 |
| chocolate, milk | 50.00 | g | 1075 | 4 | 14 | 31 | 0 | 28 | 3 |
| Total: | | | 8595 | 98 | 84 | 232 | 19 | 169 | 59 |

Discussion

A variable fraction of the starch that is eaten is not broken down in the upper alimentary tract. The undigested (resistant) starch enters the colon (large bowel) where it has a number of purported benefits, which are largely effected through the actions of the complex assemblage of bacteria that inhabit that region of the gut. In utilising starch, colonic bacteria elaborate organic acids which serve a variety of critical health-related functions. These include providing a much needed energy source for cells lining the bowel, promoting and controlling gut mucosal growth, and halting proliferation of cells that have undergone neoplastic transformation. For individuals on diets considered to be high risk for colorectal cancer and certain other serious degenerative diseases of the large bowel, these benefical bacterial metabolites are often in short supply. Population studies have shown that the incidence of large bowel cancer diminishes with increased starch consumption (and by implication, resistant starch). The protective effect of resistant starch in this regard appear to be greater than that of dietary fibre. Systemic health also appears to benefit from resistant starch, however in this case the benefits are mediated through its physiological actions in the small bowel. By consuming foods rich in resistant starch, energy intake and glycemic index are reduced. Weight loss may also be facilitated through a resistant starch-induced increase in basal metabolic rate.

In humans, small intestinal digestion appears to be the rate limiting step in starch assimilation, and it is essentially governed by several key physiological factors, the most important of which are mastication and small intestinal digesta transit. Resistant starch is clearly a physiological entity—it is a product of a variety of physiological processes acting in concert. As such it is not an innate physical constituent of starchy foods.

REFERENCES

Abel et al., (1996). *The Plant Journal* 10: 981-991.
Anderson et al., (1989). *Nucl Acids Res* 17: 461-462.
Baba et al., (1991). *Biochem Biophys Res Commun* 181: 87-94.
Batey and Curtin. (1996). *Starch* 48: 338-344.
Batey et al., (1997). *Cereal Chemistry* 74: 497-501.
Becker et al., (1994). *Plant J.* 5:299-307.
Blauth et al., (2001). *Plant Physiology* 125: 1396-1405.
Bourque. (1995). *Plant Science* 105: 125-149.
Boyer and Preiss, (1978). *Carbohydrate Research* 61: 321-334.
Boyer and Preiss, (1981). *Plant Physiology* 67: 1141-1145.
Boyer et al., (1980). *Starch* 32: 217-222.
Buleon et al., (1998). *International Journal of Biological Macromolecules* 23:85-112.
Cao et al., (1999). *Plant Physiol* 120: 205-215.
Cao et al., (2000). *Archives. of Biochemistry and Biophysics.* 373: 135-146.
Case et al., (1998). *Journal of Cereal Science* 27: 301-314.
Cheng et al., (1997). *Plant Physiol* 115: 971-980.
Craig et al., (1998). *Plant Cell* 10: 413-426.
Denyer et al., (1995). *Planta* 196: 256-265.
Denyer et al., (1996). *Plant Physiology* 112: 779-785.
Ewen and Pusztai (1999). *Lancet* 354: 1353-1354.
Feldman. pp 3-56 in The World Wheat Book, A history of wheat breeding. Eds Bonjean and Angus, Lavoisier Publishing, Paris.
Ferguson. 1994. pp 55-77 in "Speciality Corns" eds, CRC Press Inc.
Fisher et al., (1993). *Plant Physiol* 102:1045-1046.
Fisher et al., (1996). *Plant Physiol* 110: 611-619.
Fuwa et al., (1999). *Starch/Starke.* 51: 147-151.
Gao et al., (1997). *Plant Physiol* 114: 69-78.
Gao et al., (1998). *Plant Cell* 10: 399-412.
Giroux and Hannah. (1994). *Molecular and General Genetics* 243: 400-408.
Green et al., (1997). *Plant Physiology* 114: 203-212.
He et al., (1994). *Plant Cell Reports* 14: 192-196.
Hedman and Boyer, (1982). *Biochemical Genetics* 20: 483-492.
Hess et al., (1990). *Plant Science* 72: 233-244.
James et al., (1995). *Plant Cell* 7: 417-429.
Jobling et al., (1999). *Plant Journal* 18: 163-171.
Komari et al., (1996). *Plant Journal* 10: 165-174.
Konik-Rose et al (2001) *Starch* 53: 14-20.
Krueger et al., (1987). *Cereal Chemistry* 64: 187-190.
Kubo et al., (1999). *Plant physiology.* 121: 399-409.
Li et al., (1999a). *Plant physiology.* 120: 1147-1155.
Li et al., (1999b). *Theoretical and Applied Genetics* 98: 1208-1216.
Li et al., (2000). *Plant Physiology* 123: 613-624.

Li et al., (2003). *Funct Integr Genomics* 3: 76-85.
Libessart et al., (1995). *Plant Cell* 7: 1117-1127.
McCreery and Helentjaris (1994). Methods in Molecular Biology, Vol. 28: Protocols for nucleic acid analysis by non-radioactive probes, 67-71, Humana Press Inc., Totawa, N.J.
Mizuno et al., (1993). *Journal of Biological Chemistry* 268: 19084-19091.
Mizuno et al., (1992). *Journal of Biochemistry* 112: 643-651.
Morell et al., (1997). *Plant Physiology* 113: 201-208.
Morell et al., (1998). *Electrophoresis* 19: 2603-2611.
Morell et al., (2003). *Plant J.* 34: 173-185.
Morrison and Laignelet (1983). *Journal of Cereal Science* 1: 9-20.
Mullins et al., (1999). *European Journal of Plant Pathology* 105: 465-475.
Myers et al., (2000). *Plant Physiology* 122: 989-997.
Nakamura (2002). *Plant Cell Physiology* 43: 718-725.
Nakamura and Yamanouchi (1992). *Plant Physiol* 99: 1265-1266.
Nair et al., (1997). *Plant Sci* 122: 153-163.
Nehra et al., (1994). *Plant J.* 5: 285-297.
Ng et al., (1997) *Cereal Chemistry* 74: 288-292.
Nishi et al., (2001). *Plant Physiology* 127: 459-472.
Rahman et al., (1995). *Australian Journal of Plant Physiology* 22: 793-803.
Rahman et al., (1997). *Genome* 40: 465-474.
Rahman et al., (1999). *Theor Appl Genet.* 98: 156-163.
Rahman et al., (2000). *J Cereal Sci* 31: 91-110.
Rahman et al., (2001). *Plant Physiol* 125: 1314-1324.
Repellin et al., (1997). *Plant Gene Reg* 97-094
Schulman and Kammiovirta. (1991). *Starch* 43: 387-389.
Senior (1998). *Biotechnology and Genetic Engineering Reviews* 15: 79-119.
Shannon and Garwood, (1984). In *Starch: Chemistry and Technology*, Whistler et al., eds, Academic Press, Orlando, Fla., pp 25-86.
Shure et al., (1983). *Cell* 35: 225-233.
Sidebottom et al., (1998). *Journal of Cereal Science* 27: 279-287.
Slade et al. (2005). *Nat Biotech.* 23: 75-81.
Stacey and Isaac (1994). Methods in Molecular Biology, Vol. 28: Protocols for nucleic acid analysis by non-radioactive probes, pp 9-15, Humana Press Inc., Totawa, N.J.
Sun et al., (1997). *The New Phytologist* 137: 215-215.
Sun et al., (1998). *Plant Physiol* 118: 37-49.
Takeda et al., (1993a). *Carbohydrate Research* 240: 253-262.
Takeda et al., (1993b). *Carbohydrate Research* 246: 273-281.
Thomas and Atwell 1999 Starches Eagen Press, St Paul, Minn., USA pp: 13-24.
Thorbjomsen et al., (1996). *Plant Journal* 10: 243-250.
Vasil et al., (1992). *Bio/Technology* 10: 667-674.
Vasil et al., (1993). *Bio/Technology* 11: 1553-1558.
Wang et al., (1998). *Journal of Experimental Botany* 49: 481-502.
Weeks et al., (1993). *Plant Physiol* 102: 1077-1084.
Wegener et al., 1994. *Mol. Gen Genet.* 245: 465-470.
Weir et al., (2001). *Aust J Plant Physiol* 28: 807-818.
Yamamori and Endo, (1996). *Theoretical and Applied Genetics* 93: 275-281.
Yamamori et al., (2000). *Theor. Appl. Genet.* 101: 21-29
Young. (1984). in Whistler et al. (eds), Academic Press, Orlando, Fla., chap 8.
Zhao and Sharp, (1998). *Plant Breeding* 117: 488-490.
Zikiryaeva and Kasimov. (1972). *Uzbekrkii Biologicheskii Zhurnal* 6:18-20.
Zwar and Chandler, (1995). *Planta* 197: 39-48.

---

The invention claimed is:

1. A process for producing a food or beverage, comprising the steps of obtaining wheat grain having a proportion of amylose in its starch of at least 40% (w/w), at least 1% of the starch being resistant starch, and a reduced level of starch branching enzyme IIa (SBEIIa) relative to wild-type wheat grain, optionally processing the grain to produce flour, wholemeal, semolina or starch, and mixing the grain, flour, wholemeal, semolina or starch with another ingredient, thereby producing the food or beverage.

2. The process of claim 1, wherein the proportion of amylose in the starch of the grain is at least 45% (w/w).

3. The process of claim 1, wherein the starch of the grain has a chain length distribution in its amylopectin which exhibits a reduced proportion of the DP 4-12 chain length fraction relative to the amylopectin of wild-type wheat grain when measured after isoamylase debranching of the amylopectin.

4. The process of claim 1, wherein the starch of the grain has an increased gelatinisation temperature relative to starch of wild-type wheat grain, as measured by differential scanning calorimetry.

5. The process of claim 1, wherein said grain comprises a reduced level of starch branching enzyme IIb (SBEIIb) protein, enzyme activity or both relative to wild-type grain.

6. The process of claim 1, wherein the starch of the grain comprises at least 2% (w/w) resistant starch.

7. The process of claim 1, wherein the wheat grain is of the species *Triticum aestivum* ssp. *aestivum* or *Triticum turgidum* L. ssp. *durum*.

8. The process of claim 1, wherein the grain which is mixed with another ingredient is whole grain.

9. The process of claim 1, wherein the grain which is mixed with another ingredient is milled, ground, pearled, rolled, kibbled, par-boiled or cracked grain.

10. The process of claim 1 which is a process for producing a food, wherein the food is selected from the group consisting of bread, cake, biscuits, breakfast cereal, noodles, sauce, soup, pasta, pancake mix and cake mix.

11. The process of claim 1 which is a process for producing bread, wherein the grain, flour, wholemeal, semolina or starch is added during preparation of the bread and is blended with wild-type wheat starch in the form of grain, flour or wholemeal, and wherein at least 10% of the total starch in the bread is in the grain, flour, wholemeal, semolina or starch.

12. The process of claim 1 further comprising the step of heating or baking the grain or flour, wholemeal or starch obtained from the grain to at least 60° C. for at least ten minutes one or more times after the mixing step.

13. The process of claim 1, wherein the amylopectin of the grain comprises 42.27% DP 13-24 chain length fraction when measured by fluorophore assisted carbohydrate electrophoresis after isoamylase debranching of the amylopectin.

14. The process of claim 1 further comprising the step of packaging the food or beverage so that it is ready for sale.

15. A food or beverage comprising wheat grain having a proportion of amylose in its starch of at least 40% (w/w), at least 1% of the starch being resistant starch, and a reduced level of starch branching enzyme IIa (SBEIIa) relative to wild-type wheat grain, or flour, wholemeal, or semolina produced from the grain, and another ingredient.

* * * * *

SEQUENCE LISTING

```
<160> NUMBER OF SEQ ID NOS: 11

<210> SEQ ID NO 1
<211> LENGTH: 11476
<212> TYPE: DNA
<213> ORGANISM: Aegilops tauschii
<220> FEATURE:
<221> NAME/KEY: misc_feature
<222> LOCATION: (1722)..(10458)
<223> OTHER INFORMATION: n = not known
      This sequence represents wSBEII-D1 gene

<400> SEQUENCE: 1
agaaacacct ccattttaga ttttttttt gttcttttcg gacggtgggt cgtggagaga      60
ttagcgtcta gttttcttaa aagaacaggc catttaggcc ctgctttaca aaaggctcaa    120
ccagtccaaa acgtctgcta ggatcaccag ctgcaaagtt aagcgcgaga ccaccaaaac    180
aggcgcattc gaactggaca gacgctcacg caggagccca gcaccacagg cttgagcctg    240
acagcggacg tgagtgcgtg acacatgggg tcatctatgg gcgtcggagc aaggaagaga    300
gacgcacatg aacaccatga tgatgctatc aggcctgatg gagggagcaa ccatgcacct    360
tttcccctct ggaaattcat agctcacact ttttttaat ggaagcaaga gttggcaaac     420
acatgcattt tcaaacaagg aaaattaatt ctcaaccac catgacatgc aattctcaaa     480
ccatgcaccg acgagtccat gcgaggtgga aacgaagaac tgaaaatcaa catcccagtt    540
gtcgagtcga gaagaggatg acactgaaag tatgcgtatt acgatttcat ttacatacat    600
```

-continued

```
gtacaaatac ataatgtacc ctacaatttg ttttttggag cagagtggtg tggtcttttt      660
tttttacacg aaaatgccat agctggcccg catgcgtgca gatcggatga tcggtcggag      720
acgacggaca atcagacact caccaactgc ttttgtctgg gacacaataa atgttttgt       780 aaacaaaata aatacttata aacgagggta ctagaggccg ctaacggcat ggccaggtaa      840
acgcgctccc agccgttggt ttgcgatctc gtcctcccgc acgcagcgtc gcctccaccg      900
tccgtccgtc gctgccacct ctgctgtgcg cgcgcacgaa gggaggaaga acgaacgccg      960
cacacacact cacacacggc acactccccg tgggtcccct ttccggcttg cgtctatct      1020 cctctccccc gcccatcccc atgcactgca ccgtacccgc cagcttccac ccccgccgca     1080
cacgttgctc ccccttctca tcgcttctca attaatatct ccatcactcg ggttccgcgc     1140
tgcatttcgg ccggcgggtt gagtgagatc tgggcgactg gctgactcaa tcactacgcg     1200
gggatggcga cgttcgcggt gtccggcgcg actctcggtg tggcgcgggc cggcgtcgga     1260
gtggcgcggg ccggctcgga gcggaggggc ggggcggact tgccgtcgct gctcctcagg     1320
aagaaggact cctctcgtac gcctcgctct ctcgaatctc ccccgtctgg ctttggctcc     1380
ccttctctct cctctgcgcg cgcatggcct gttcgatgct gttccccaat tgatctccat     1440
gagtgagaga gatagctgga ttaggcgatc gcgcttcctg aacctgtatt ttttcccccg     1500
cggggaaatg cgttagtgtc acccaggccc tggtgttacc acggctttga tcattcctcg     1560
tttcattctg atatatattt tctcattctt tttcttcctg ttcttgctgt aactgcaagt     1620
tgtggcgttt tttcactatt gtagtcatcc ttgcatttg caggcgccgt cctgagccgc      1680
gcggcctctc cagggaaggt cctggtgcct gacggcgaga gngacgactt ggcaagtccg     1740
gcgcaacctg aagaattaca ggtacacaca ctcgtgccgg taaatcttca tacaatcgtt     1800
attcacttac caaatgccgg atgaaaccaa ccacggatgc gtcaggtttc gagcttcttc     1860
tatcagcatt gtgcagtact gcactgcctt gttcattttg ttagccttgg ccccgtgctg     1920
gctcttgggc cactgaaaaa atcagatgga tgtgcattct agcaagaact tcacaacata     1980
atgcaccgtt tggggtttcg tcagtctgct ctacaattgc tatttttcgt gctgtagata     2040
cctgaagata tcgaggagca aacggcgaaa gtgaacatga caggggggac tgcagagaaa     2100
cttcaatctt cagaaccgac tcagggcatt gtggaaacaa tcactgatgg tgtaaccaaa     2160
ggagttaagg aactagtcgt gggggagaaa ccgcgagttg tcccaaaacc aggagatggg     2220
cagaaaatat acgagattga cccaacactg aaagattttc ggagccatct tgactaccgg     2280
taatgcctac ccgctgcttt cgctcatttt gaattaaggt cctttcatca tgcaaatttg     2340
gggaacatca aagagacaaa gactagggac caccatttca tacagatccc ttcgtggtct     2400
gagaatatgc tgggaagtaa atgtataatt gatggctaca atttgctcaa aattgcaata     2460
cgaataactg tctccgatca ttacaattaa agagtggcaa actgatgaaa atgtggtgga     2520
tgggttatag atttactttt gctaattcct ctaccaaatt cctagggggg aaatctacca     2580
gttgggaaac ttagtttctt atctttgtgg ccttttgtt ttggggaaaa cacattgcta      2640
aattcgaatg attttgggta tacctcgtg gattcaacag atacagcgaa tacaagagaa      2700
ttcgtgctgc tattgaccaa catgaaggtg gattggaagc attttctcgt ggttatgaaa     2760
agcttggatt tacccgcagg taaatttaaa gctttattat tatgaaacgc ctccactagt     2820
ctaattgcat atcttataag aaaatttata attcctgttt tccctctct ttttccagt       2880 gctgaaggta tcgtctaatt gcatatctta taagaaaatt tatattcctg ttttccccta     2940
ttttccagtg ctgaaggtat cacttaccga gaatgggctc cctggagcgc atgttatgtt     3000
```

```
cttttaagtt ccttaacgag acaccttcca atttattgtt aatggtcact attcaccaac    3060
tagcttactg gacttacaaa ttagcttact gaatactgac cagttactat aaatttatga    3120
tctggctttt gcaccctgtt acagtctgca gcattagtag gtgacttcaa caattggaat    3180
ccaaatgcag atactatgac cagagtatgt ctacagcttg gcaattttcc acctttgctt    3240
cataactact gatacatcta tttgtattta tttagctgtt tgcacattcc ttaaagttga    3300
gcctcaacta catcatatca aaatggtata atttgtcagt gtcttaagct tcagcccaaa    3360
gattctactg aatttagtcc atcttttga gattgaaaat gagtatatta aggatgaatg    3420
aatacgtgca acactcccat ctgcattatg tgtgcttttc catctacaat gagcatattt    3480
ccatgctatc agtgaaggtt tgctcctatt gatgcagata tttgatatgg tcttttcagg    3540
atgattatgg tgtttgggag attttcctcc ctaacaacgc tgatggatcc tcagctattc    3600
ctcatggctc acgtgtaaag gtaagctggc caattattta gtcgaggatg tagcattttc    3660
gaactctgcc tactaagggt ccctttcct ctctgttttt tagatacgga tggatactcc    3720
atccggtgtg aaggattcaa tttctgcttg gatcaagttc tctgtgcagg ctccaggtga    3780
aatacctttc aatggcatat attatgatcc acctgaagag gtaagtatcg atctacatta    3840
cattattaaa tgaaatttcc agtgttacag tttttaata cccacttctt actgacatgt    3900
gagtcaagac aatactttg aatttggaag tgacatatgc attaattcac cttctaaggg    3960
ctaaggggca accaaccttg gtgatgtgtg tatgcttgtg tgtgacataa gatcttatag    4020
ctcttttatg tgttctctgt tggttaggat attccatttt ggccttttgt gaccatttac    4080
taaggatatt tacatgcaaa tgcaggagaa gtatgtcttc caacatctca actaaacgac    4140
cagagtcact aaggatttat gaatcacaca ttggaatgag cagcccggta tgtcaataag    4200
ttatttcacc tgtttctggt ctgatggttt attctatgga ttttctagtt ctgttatgta    4260
ctgttaacat attacatggt gcattcactt gacaacctcg atttattttt ctaatgtctt    4320
catattggca agtgcaaaac tttgcttcct ctttgtctgc ttgttctttt gtcttctgta    4380
agatttccat tgcatttgga ggcagtgggc atgtgaaagt catatctatt ttttttttgt    4440
cagagcatag ttatatgaat tccattgttg ttgcaatagc tcggtataat gtaaccatgt    4500
tactagctta agatttccca cttaggatgt aagaaatatt gcattggagc gtctccagca    4560
agccatttcc taccttatta atgagagaga dacaaggggg gggggggggg ggggttccc    4620 ttcattattc tgcgagcgat tcaaaaactt ccattgttct gaggtgtacg tactgcaggg    4680
atctcccatt atgaagagga tatagttaat tctttgtaac ctacttggaa acttgagtct    4740
tgaggcatcg ctaatatata ctatcatcac aatacttaga ggatgcatct gaanatttta    4800
gtgtgatctt gcacaggaac cgaagataaa ttcatatgct aattttaggg atgaggtgtt    4860
gccaagaatt aaaaggcttg gatacaatgc agtgcagata atggcaatcc aggagcattc    4920
atactatgca agctttgggt attcacacaa tccatttttt tctgtataca cntcttcacc    4980
catttggagc tattacatcc taatgcttca tgcacataaa atatttggat ataatccttt    5040
attagatata tagtacaact acacttagta ttctgannaa naagatcatt ttattgttgt    5100
tggcttgttc caggtaccat gttactaatt ttttgcacc aagtagccgt tttggaactc    5160
cagaggactt aaaatccttg atcgatagag cacatgagct tggtttgctt gttcttatgg    5220
atattgttca taggtaatta gtccaattta atttagctg ttttactgtt tatctggtat    5280
tctaaaggga aattcaggca attatgatac attgtcaaaa gctaagagtg gcgaaagtga    5340
aatgtcaaaa tctagagtgg cataaggaaa attggcaaaa actagagtgg caaaaataaa    5400
```

```
attttcccat cctaaatggc agggccctat cgccgaatat ttttccattc tatataattg    5460
tgctacgtga cttcttttt ctcagatgta ttaaaccagt tggacatgaa atgtatttgg    5520
tacatgtagt aaactgacag ttccatagaa tatcgttttg taatggcaac acaatttgat    5580
gccatagatg tggattgaga agttcagatg ctatcaatag aattaatcaa ctggccatgt    5640
actcgtggca ctacatatag tttgcaagtt ggaaaactga cagcaatacc tcactgataa    5700
gtggccaggc cccacttgcc agcttcatac tagatgttac ttccctgttg aattcatttg    5760
aacatattac ttaaagttct tcatttgtcc taagtcaaac ttctttaagt ttgaccaagt    5820
ctattggaaa atatatcaac atctacaaca ccaaattact ttgatcagat taacaatttt    5880 tatttatta tattagcaca tctttgatgt tgtagatatc agcacatttt tctatagact    5940
tggtcaaata tagagaagtt tgacttagga caaatctaga acttcaatca atttggatca    6000
gagggaacat caaataatat agatagatgt caacacttca acaaaaaaat cagaccttgt    6060
caccatatat gcatcagacc atctgttgc tttagccact tgctttcata tttatgtgtt    6120
tgtacctaat ctacttttcc ttctacttgg tttggttgat tctatttcag ttgcattgct    6180
tcatcaatga ttttgtgtac cctgcagtca ttcgtcaaat aatacccttg acggtttgaa    6240
tggtttcgat ggcactgata cacattactt ccacggtggt ccacgcggcc atcattggat    6300
gtgggattct cgtctattca actatgggag ttgggaagta tgtagctctg acttctgtca    6360
ccatatttgg ctaactgttc ctgttaatct gttcttacac atgttgatat tctattctta    6420
tgcaggtatt gagattctta ctgtcaaacg cgagatggtg gcttgaagaa tataagtttg    6480
atggatttcg atttgatggg gtgacctcca tgatgtatac tcaccatgga ttacaagtaa    6540
gtcatcaagt ggtttcagta actttttag ggcactgaaa caattgctat gcatcataac    6600
atgtatcatg atcaggactt tgtgctacgga gtcttagata gttccctagt atgcttgtac    6660
aattttacct gatgagatca tggaagattg gaagtgatta ttatttattt tctttctaag    6720
tttgtttctt gttctagatg acatttactg ggaactatgg cgaatatttt ggatttgcta    6780
ctgatgttga tgcggtagtt tacttgatgc tggtcaacga tctaattcat ggactttatc    6840
ctgatgctgt atccattggt gaagatgtaa gtgcttacag tatttatgat ttttaactag    6900
ttaagtagtt ttattttggg gatcagtctg ttacactttt tgttaggggt aaaatctctc    6960
ttttcataac aatgctaatt tataccttgt atgataatgc atcacttang taatttgaaa    7020
agtgcaaggg cattcaagct tacgagcata tttttgatg gctgtaattt atttgatagt    7080
atgcttgttt gggtttttca ataagtggga gtgtgtgact aatgttgtat tatttattta    7140
attgcggaag aaatgggcaa ccttgtcaat tgcttcagaa ggctaacttt gattccataa    7200
acgctttgga aatgagaggc tattcccaag gacatgaatt atacttcagt gtgttctgta    7260
catgtatttg taatagtggt ttaacttaaa ttcctgcact gctatggaat ctcactgtat    7320
gttgtnagtg tacacatcca caaacaagta atcctgagct ttcaactcat gagaaaatan    7380
gangtccgct tctgccagca ttaactgttc acagttctaa tttgtgtaac tgtgaaattg    7440
ttcaggtcag tggaatgcct acattttgca tccctgttcc agatggtggt gttggttttg    7500
actaccgcct gcatatggct gtagcagata aatggattga actcctcaag taagtgcagg    7560
aatattggtg attacatgcg cacaatgatc tagattacat tttctaaatg gtaaaaagga    7620
aaatatgtat gtgaatatct agacatttgc ctgttatcag cttgaatacg agaagtcaaa    7680
tacatgattt aaatagcaaa tctcggaaat gtaatggcta gtgtctttat gctgggcagt    7740
gtacattgcg ctgtagcagg ccagtcaaca cagttagcaa tattttcaga aacaatatta    7800
```

```
tttatatccg tatatganga aagttagtat ataaactgtg gtcattaatt gtgttcacct   7860
tttgtcctgt ttaaggatgg gcagtaggta ataaatttag ccagataaaa taaatcgtta   7920
ttaggtttac aaaaggaata tacagggtca tgtagcatat ctagttgtaa ttaatgaaaa   7980
ggctgacaaa aggctcggta aaaaaaactt tatgatgatc cagatagata tgcaggaacg   8040
cgactaaagc tcaaatactt attgctacta cacagctgcc aatctgtcat gatctgtgtt   8100
ctgctttgtg ctatttagat ttaaatacta actcgataca ttggcaataa taaacttaac   8160
tattcaacca atttggtgga taccaganat ttctgccctc ttgttagtaa tgatgtgctc   8220
cctgctgctg ttctctgccg ttacaaaagc tgttttcagt tttttgcatc attattttg    8280
tgtgtgagta gtttaagcat gttttttgaa gctgtgagct gttggtactt aatacattct   8340
tggaagtgtc caaatatgct gcagtgtaat ttagcatttc tttaacacag gcaaagtgac   8400
gaatcttgga aaatgggcga tattgtgcac accctaacaa atagaaggtg gcttgagaag   8460
tgtgtaactt atgcagaaag tcatgatcaa gcactagttg gtgacaagac tattgcattc   8520
tggttgatgg ataaggtact agctgttact tttggacaaa agaattactc cctcccgttc   8580
ctaaatataa gtctttgtag agattccact atggaccaca tagtatatag atgcattta    8640
gagtgtagat tcactcattt tgcttcgtat gtagtccata gtgaaatctc tacagagact   8700
tatatttagg aacggaggga gtacataatt gatttgtctc atcagattgc tagtgttttc   8760
ttgtgataaa gattggctgc ctcacccatc accagctatt tcccaactgt tacttgagca   8820
gaatttgctg aaaacgtacc atgtggtact gtggcggctt gtgaactttg acagttatgt   8880
tgcaattttc tgttcttatt tatttgattg cttatgttac cgttcatttg ctcattcctt   8940
tccgagacca gccaaagtca cgtgttagct gtgtgatctg ttatctgaat cttgagcaaa   9000
ttttattaat aggctaaaat ccaacgaatt atttgcttga atttaaatat acagacgtat   9060
agtcacctgg ctctttctta gatgattacc atagtgcctg aaggctgaaa tagttttggt   9120
gtttcttgga tgccgcctaa aggagtgatt tttattggat agattcctgg ccgagtcttc   9180
gttacaacat aacattttgg agatatgctt agtaacagct ctgggaagtt tggtcacaag   9240
tctgcatcta cacgctcctt gaggttttat tatggcgcca tctttgtaac tagtggcacc   9300
tgtaaggaaa cacattcaaa aggaaacggt cacatcattc taatcaggac caccatacta   9360
agagcaagat tctgttccaa tttatgagt ttttgggact ccaaagggaa caaaagtgtc    9420
tcatattgtg cttataacta cagttgtttt tataccagtg tagttttatt ccaggacagt   9480
tgatacttgg tactgtgctg taaattattt atccgacata aacagcatg aacatatcaa    9540
gctctctttg tgcaggatat gtatgatttc atggctctgg ataggcttca actcttcgca   9600
ttgatcgtgg catagcatta cataaaatga tcaggcttgt caccatgggt ttaggtggtg   9660
aaggctatct taacttcatg ggaaatgagt ttgggcatcc tggtcagtct ttacaacatt   9720
attgcattct gcatgattgt gatttactgt aatttgaacc atgctttct ttcacattgt    9780
atgtattatg taatctgttg cttccaagga ggaagttaac ttctatttac ttggcagaat   9840
ggatagattt tccaagaggc ccacaaactc ttccaaccgg caaagttctc ccctggaaat   9900
aacaatagtt atgataaatg ccgccgtaga tttgatcttg taagttttag ctgtgctatt   9960
acattccctc actagatctt tattggccat ttatttcttg atgaaatcat aatgtttgtt  10020
aggaaagatc aacattgctt ttgtagtttt gtagacgtta acataagtat gtgttgagag  10080
ttgttgatca ttaaaaatat catgattttt tgcagggaga tgcagatttt cttagatatc  10140
gtggtatgca agagttcgat caggcaatgc agcatcttga ggaaaaatat ggggtatgtc  10200
```

-continued

```
actggtttgt ctttgttgca taacaagtca cagtttaacg tcagtctctt caagtggtaa    10260
aaaaagtgta gaattaattc ctgtaatgag atgaaaactg tgcaaaggcg gagctggaat    10320
tgcttttcac caaaactatt ttcttaagtg cttgtgtatt gatacatata ccagcactga    10380
caatgtaact gcagtttatg acatctgagc accagtatgt ttcacggaaa catgaggaag    10440
ataaggtgat catcctcnaa aagaggagat ttggtatttg ttttcaactt ccactggagc    10500
aatagctttt ttgactaccg tgttgggtgt tccaagcctg ggaagtacaa ggtatgcttg    10560
ccttttcatt gtccacccct caccagtagg gttagtgggg gcttctacaa cttttaattc    10620
cacatggata gagtttgttg gtcgtgcagc tatcaatata aagaataggg taatttgtaa    10680
agaaaagaat ttgctcgagc tgttgtagcc ataggaaggt tgttcttaac agccccgaag    10740
cacataccat tcattcatat tatctactta agtgtttgtt tcaatcttta tgctcagttg    10800
gactcggtct aatactagaa ctattttccg aatctaccct aaccatccta gcagttttag    10860
agcagcccca tttggacaat tggctgggtt tttgttagtt gtgacagttt ctgctatttc    10920
ttaatcaggt ggccttggac tctgacgatg cactcttttgg tggattcagc aggcttgatc    10980
atgatgtcga ctacttcaca accgtaagtc tgggctcaag cgtcacttga ctcgtcttga    11040
ctcaactgct tacaaatctg aatcaacttc ccaattgctg atgcccttgc aggaacatcc    11100
gcatgacaac aggccgcgct ctttctcggt gtacactccg agcagaactg cggtcgtgta    11160
tgcccttaca gagtaagaac cagcagcggc ttgttacaag gcaaagagag aactccagag    11220
agctcgtgga tcgtgagcga agcgacgggc aacggcgcga ggctgctcca agcgccatga    11280
ctgggagggg atcgtgcctc ttccccagat gccaggagga gcagatggat aggtagcttg    11340
ttggtgagcg ctcgaaagaa aatggacggg cctgggtgtt tgttgtgctg cactgaaccc    11400
tcctcctatc ttgcacattc ccggttgttt ttgtacatat aactaataat tgcccgtgcg    11460
ctcaacgtga aaatcc                                                    11476
```

<210> SEQ ID NO 2
<211> LENGTH: 6520
<212> TYPE: DNA
<213> ORGANISM: Triticum aestivum
<220> FEATURE:
<221> NAME/KEY: misc_feature
<222> LOCATION: (4606)..(6215)
<223> OTHER INFORMATION: n = not known
    This sequence represents partial wSBEIIb gene

<400> SEQUENCE: 2

```
aagctttgta gccttgcacg ggctcccaa caaactgcct cactcgattg tcaaaaaagt       60
aaaaatgatt gtagaaaaaa aaactgactc actcgtcact accctaccgt cctacatgac      120
acctggccgc aagacgacgc cgtcctcctg ccgcgcgcgt ccgcgatcac accaccgcaa      180
aaaccaaaac ctcttcgccg gtgcgtccca cgctaccatc catgcagccg tccgcccgcg      240
cgcgcgttgc ccgcaccacc cgctggcggc caccacgccc ccactctcgc gtgaaggctc      300
cgtccgcttc ctcctagttc cactctctct ccgtgctagc agtatatagc atccgccctc      360 cgcccccctcc caatcttaga acacccctcc ctttgcctcc tcatttcgct cgcgtgggtt     420
taagcaggag acgaggcggg gtcagttggg cagttaggtt ggatccgatc cggctgcggc     480
ggcggcgacg ggatggctgc gccggcattc gcagtttccg cggcggggct ggcccggccg    540
tcggctcctc gatccggcgg ggcagagcgg agggggcgcg gggtggagct gcagtcgcca     600
tcgctgctct tcggccgcaa caagggcacc cgttcacccc gtaattattt gcgccacctt     660
tctcactcac attctctcgt gtattctgtc gtgctcgccc ttcgccgacg acgcgtgccg     720
```

```
attccgtatc gggctgcggt gttcagcgat cttacgtcgg ttccctcctg gtgtggtgat    780
gtctgtaggt gccgtcggcg tcggaggttc tggatggcgc gtggtcatgc gcgcgggggg    840
gccgtccggg gaggtgatga tccctgacgg cggtagtggc ggaacaccgc cttccatcga    900
cggtcccgtt cagttcgatt ctgatgatct gaaggtagtt ttttttttgc atcgatctga    960
aggtacttga catatactac tgtattaccc tgagtaaata ctgccaccat attttttatgg  1020
ttcgcttgaa atacctgttt acttgctacg gttttcactt tcattgagac gtcggacgaa   1080
attcactgaa ttcctataat ttggtagaca ccgaaatata tactactcct tccgtcccat   1140
aatataagag cgttttttggc accttatatt atagggcgga gggagtacct tttaggtcaa  1200
aatattgtgg tagtttcaat tgtatacaag aattcaaata ttttttttaa aaaaaaatca   1260
actaattggt tgagtttcaa gtgaagcgtt ttggtccttt ggctgagatg taaaccgaaa   1320
tcactgaaat tcatagtagc cgaaacttta atagaactga aactcaaaat ctgctatccg   1380
gcgaaattct aaagatttgc ttatttcaca cgtaggttgc agtacaccct cttcctaatt   1440
tattggggaa ggggtattat tatcttgtta gtacctgcct gcatgacaat tgaaatctaa   1500
gacaaaacac catatgcgag gcctacacac ggtaggttgg tttacaacta tgtgtgccac   1560
agttcgtctg aacttttttgt ccttcacatc gtgttaggtt ccattcattg atgatgaaac   1620
aagcctacag gatggaggtg aagatagtat ttggtcttca gagacaaatc aggttagtga   1680
agaaattgat gctgaagaca cgagcagaat ggacaaagaa tcatctacga gggagaaatt   1740
acgcattctg ccaccaccgg gaaatggaca gcaaatatac gagattgacc caacgctccg   1800
agactttaag taccatcttg agtatcggta tgcttcgctt ctattgtgtg cactttaaaa   1860
acaatttaca gtcttttgata agatgtgaat ggctgcttgc tgtgacacga aactcttgaa   1920
gttcgtagtc actcttgtgt gttcatggtt ctgaggtaac atggtaaccg aacaaaaata   1980
ggaaagtggc aagcactgca atgtgagcta ctgataacca cccattgtaa ttgggtacac   2040
tgattaatat atatgtcttc atgggctcta tttttttttca atatctatgc caattgaaca   2100
acaatgcttt gtggacgggt gttcttttac cctcttcttc tatcaataga tgatatgcat   2160
actcatgcgt atcctacaaa aaattgaaca acaatgccac tttccccgt gttgcttttg    2220
taaggatgaa acacatatgt ccagatcaaa ctatactagc agtctaactg tgccttaatg   2280
gatcaaaaac agatatagcc tatacaggag aatacgttca gacattgatg aacacgaagg   2340
aggcatggat gtatttttccc gcggttacga gaagttggag tttatgcgca ggtgaaattt    2400
cttgactaaa taactatgta tctacctttt ctttgtactc tatcaacatt cctcttccca   2460
tgcagcgctg aaggtatcac ttaccgagaa tgggctcctg gagcagatgt acgttcttct   2520
aaccatctga tcgtttacct gactatacta attctatctt tcaactaatt gtgaataatt   2580
actgctcatc agctatccta aggttgggga ttttgcacct cccagatgaa cagcatatta   2640
agtcgcacaa ctagcattat taagaactaa ctcctgcttc caattgcagt ctgcagcatt   2700
agttggcgac ttcaacaatt gggatccaaa tgcagaccat atgagcaaag tatgcatgta   2760
gtttcacaaa tatatcatat tttctttgta gattttttttt tttagatcgg cttatctatt   2820
acgttgagct gtaaatatag ttggaagtgt ttaggagtat taaattcact ggactctatt   2880
cttcacttg cctgttgcac gagcccatta ctagatatca atgttgatga tgcttttgtt   2940
gtatgaggtc gaagtgaaac atgcatgtta cccttttata taagtaaggt tgcacatgta   3000
tttttttatga tctaaacatt atttactgat tttgttcttg caagacacta agcagtttta  3060
cataataatg gcgttggagc aggccgactg cacatctgaa ctgtagctcc atgtggttga   3120
```

```
tatagattac aaatgctcat attcaatgta actgttttca gaatgacctt ggtgtttggg      3180
agatttttct gccaaacaat gcagatggtt cgccaccaat tcctcacggc tcacgggtga      3240
aggttgtttt cttctccttg ccaacggtgt taggctcagg aacatgtcct gtattactca      3300
gaagctcttt tgaacatcta ggtgagaatg gatactccat ctgggataaa ggattcaatt      3360
cctgcttgga tcaagtactc cgtgcagact ccaggagata taccatacaa tggaatatat      3420
tatgatcctc ccgaagaggt attttacttc atcttctgtg cttttagatt tcagatattt      3480
ttattagaag aaaattatga tttttttccct cacgaacctt cccaattgct atttcaagct      3540
gtcctactta tttgctgctg gcatcttatt tttctattct ctaaccagtt atgaaattcc      3600
ttacatgcat atgcaggaga agtatgtatt caagcatcct caacctaaac gaccaaaatc      3660
attgcggata tatgaaacac atgttggcat gagtagcccg gtatttcatc tttaccatgt      3720
attccataaa tgaagttagc tatatgcagt tcaaatttat ttacaggttg ttacaatggt      3780
atttttgtgt tggtgcccctt ctttcgtttt ataagtaaaa aacttatcat aaatttattt      3840
gttatgccgc ttggttaata caatctgaaa aatgtaactg tggacaatct agaactagat      3900
aatacaaatc tgaaaaaaca tgctggaata gtgtcatttc agtcaactag gatgttttga      3960
atgctcaaga gaagtactag tgtgtagcat caaaagctgg tgtccatttg ttcaaatgtt      4020
taattaacac tatagtgaaa acaagtaatt gcacaaagaa acaagtaatt gcccaagttc      4080
atatgttttt tcactatatt acatgtttca tcaacaattt aattaacctc attccttaca      4140
aacatttgta tttacatttg ttcctacata tatagttatt ttatatatca actttataaa      4200
tcatgactgt tataattaaa accgatggta tatcaacgat tgagataatt tggcatatgt      4260
ggatgaattt tgtggcttgt tatgctcttg ttttaataac ataataaata gattatgctt      4320
gttggtagcc ttttttacatt aacacatggg caattacttg tttctttgtg caaccaggaa      4380
ccaaagatcg acacatatgc aaacttcagg gatgaggtgc ttccaagaat taaaagactt      4440
ggatacaatg cagtgcaaat aatggcaatc caagagcact catactatgg aagctttggg      4500
tagttctctg ggtcgatttc tggttctttt agttatcttt tgtccataga acatatttca      4560
actttagcaa ctatactatt atattaactt ttcagctatt gtcttnctt tcttatgtg        4620 agagactgct gcntcttgct acttcctgtg ttctcattca gagtanacat cttatganta      4680
gacaactcta tgtngacatt ccggaagtat ncactggctg attcggtcta aaataacata      4740
ctgctcagat agccacataa cagtacgatt acacacataa tgaccatgtt tgcatagagt      4800
ggcggtagta tgttcctcac catactagca taatgacttg ttatataaga gtatatcata      4860
ttaacttctt ttccaatgac atggaagctg taacaacttt caaatcattt ttgtcttttta     4920 agtgctgctt ttttcctgtt tgacaattaa tacaatacca cttttatgtg tttttacttc      4980
tattgcaggt accatgttac caatttcttt gcaccaagta gccgttttgg gtccccagaa      5040
gatttaaaat ctttgattga tagagctcac gagcttggct tggttgtcct catggatgtt      5100
gttcacaggt acttaatgta atttgaggtt ggcgtgttaa gttcacatta atcttaattc      5160
tttatttcaa ttcctatggc ctctctccta gattggaaca gtaaaagcat catccagttt      5220
gtataaattg ctaaaagaac attttacatg ttaagtattt tcaattacta tgaaacatat      5280
aaatttacat acttattgat tttacgacag aagtaccgat ctcacaagat gaacaattgg      5340
ttgatcacat atcatttcat actacaatac aagaaaatga atagagaacg agttaatatt      5400
agccttggta aaatcagcaa cttgtttgga aataaagtat agtgatgcca gtgcaaanaa      5460
caaggcatca agttggtttc agctcccacg gtcggtgcta gctgtcaagg gtaatttgca      5520
```

```
cgtagtcgca catagatttg tgtgggagtg gaaagtaacc acagattgtc cgaggaacac    5580
gggacacacg tcttagccac aggtttgggc tccccttgat gcgggtagta gctttactcc    5640
ttatatgaaa ttatctcaag atagatttca atttggggtt acacttanga actcancaag    5700
ttaaggatca actcnctgag ttctatacga ctgatctttg accgagatat cttgatcagg    5760
ctaagtanca aaatccaggc cttgagatgt tgaacatgtc cttcattttg ggctgggtgc    5820
ccttgggcat aaggtgtngt ccttccttca tgtgcttctt gcagcgtatg acataaacnt    5880
cctctgagtt ggtanatgca cggttcccctt tgaggaaatc aggggtagtc gcatctnggg   5940
aaagttggtc acccangcat ggatcctcng cgcacaccgg gcaaacacgg tgaaaccact    6000
tctcctcgac actagctaac ttgacattca agcaaactaa gaatataact ttatntctaa    6060
atgaaccgga caccctcctt gtgcctgcac ctacagagta caatgccagt tttggactga    6120
actcttgtgt tcatgtatgt gctaatnaca taggttctaa ccatgattct aaatagcgcg    6180
ttataactcc actatagtaa tgctatagcg tttanaagat cccgcactaa gggaccttag    6240
tccaaataca tgatcaaaca ttttacatag cgcgctatag ctatttaaaa ctatggtcac    6300
ccgctaagag gcataactcg ctatttaaaa ctatggttct aacttttaat ctattttatg    6360
tcttggtcca aagccccttt ttgttctata gctttacctt tgggttgaga tcacccttaa    6420
cccattggta atcctggttg atttactcca tcctttcttg cgtagcttta cttttggttt    6480
tttgtttctc acagtcacgc gtcaaataat accttggacg                         6520

<210> SEQ ID NO 3
<211> LENGTH: 2832
<212> TYPE: DNA
<213> ORGANISM: Triticum aestivum
<220> FEATURE:
<223> OTHER INFORMATION: This sequence represents wSBEIIb gene

<400> SEQUENCE: 3
cgtgggttta agcaggagac gaggcggggt cagttgggca gttaggttgg atccgatccg      60
gctgcggcgg cggcgacggg atggctgcgc cggcattcgc agtttccgcg gcggggctgg     120
cccggccgtc ggctcctcga tccggcgggg cagagcggag ggggcgcggg gtggagctgc     180
agtcgccatc gctgctcttc ggccgcaaca agggcacccg ttcacccccgt gccgtcggcg    240 tcggaggttc tggatggcgc gtggtcatgc gcgcgggggg gccgtccggg gaggtgatga     300
tccctgacgg cggtagtggc ggaacaccgc cttccatcga cggtcccgtt cagttcgatt     360
ctgatgatct gaaggttcca ttcattgatg atgaaacaag cctacaggat ggaggtgaag     420
atagtatttg gtcttcagag acaaatcagg ttagtgaaga aattgatgct gaagacacga     480
gcagaatgga caaagaatca tctacgaggg agaaattacg cattctgcca ccaccgggaa     540
atggacagca aatatacgag attgacccaa cgctccgaga cttttaagtac catcttgagt     600 atcgatatag cctatacagg agaatacgtt cagacattga tgaacacgaa ggaggcatgg     660
atgtattttc ccgcggttac gagaagtttg gatttatgcg cagcgctgaa ggtatcactt     720
accgagaatg ggctcctgga gcagattctg cagcattagt tggcgacttc aacaattggg     780
atccaaatgc agaccatatg agcaaaaatg accttggtgt ttgggagatt tttctgccaa     840
acaatgcaga tggttcgcca ccaattcctc acggctcacg ggtgaaggtg cgaatgggta     900
ctccatctgg gacaaaggat tcaattcctg cttggatcaa gtactccgtg cagactccag     960
gagatatacc atacaatgga atatattatg atcctcccga agaggagaag tatgtattca    1020 agcatccctca acctaaacga ccaaaatcat tgcggatata tgaaacacat gttggcatga    1080
```

```
gtagcccgga accaaagatc aacacatatg caaacttcag ggatgaggtg cttccaagaa    1140
ttaaaagact tggatacaat gcagtgcaaa taatggcaat ccaagagcac tcatactatg    1200
gaagctttgg gtaccatgtt accaatttct ttgcaccaag tagccgtttt gggtccccag    1260
aagatttaaa atctttgatt gatagagctc acgagcttgg cttggttgtc ctcatggatg    1320
ttgttcacag tcacgcgtca ataatacctt tggacgggtt gaatggtttt gatggcacgg    1380
atacacatta cttccatggc ggttcacggg gccatcactg gatgtgggat tcccgtgtgt    1440
ttaactatgg gaataaggaa gttataaggt ttctactttc caatgcaaga tggtggctag    1500
aggagtataa gtttgatggt ttccgattcg atggcgcgac ctccatgatg tatacccatc    1560
atggattaca agtaacccttt acaggaagct accatgaata ttttggcttt gccactgatg    1620
tagatgcggt cgtttacttg atgctgatga atgatctaat tcatgggttt tatcctgaag    1680
ccgtaactat cggtgaagat gttagtggaa tgcctacatt tgcccttcct gttcaagttg    1740
gtggggttgg ttttgactat cgcttacata tggctgttgc ccgcaaatgg attgaacttc    1800
tcaaaggaaa cgatgaagct tgggagatgg gtaatattgt gcacacacta acaaacagaa    1860
ggtggctgga aaagtgtgtt acttatgctg aaagtcacga tcaagcactt gttggagaca    1920
agactattgc attctggttg atggacaagg atatgtatga tttcatggcg ctgaacggac    1980
cttcgacgcc taatattgat cgtggaatag cactgcataa aatgattaga cttatcacaa    2040
tgggtctagg aggagagggt tatcttaact ttatgggaaa tgagttcggg catcctgaat    2100
ggatagactt tccaagaggc ccacaagtac ttccaagtgg taagttcatc ccaggaaaca    2160
acaacagtta cgacaaatgc cgtcgaagat ttgacctggg tgatgcagaa tttcttaggt    2220
atcatggtat gcagcagttt gatcaggcaa tgcagcatct tgaggaaaaa tatggttta    2280 tgacatcaga ccaccagtac gtatctcgga acatgaggga agataaggtg atcgtgtttg    2340
aaaaagggga cttggtattt gtgttcaact tccactggag tagtagctat ttcgactacc    2400
gggtcggctg tttaaagcct gggaagtaca aggtggtctt agactcggac gctggactct    2460
ttggtggatt tggtaggatc catcacactg cagagcactt cacttctgac tgccaacatg    2520
acaacaggcc ccattcattc tcagtgtaca ctcctagcag aacctgtgtt gtctatgctc    2580
caatgaacta acagcaaagt gcagcatacg cgtgcgcgct gttgttgcta gtagcaagaa    2640
aaatcgtatg gtcaatacaa ccaggtgcaa ggtttaataa ggattttgc ttcaacgagt    2700 cctggataga caagacaaca tgatgttgtg ctgtgtgctc ccaatcccca gggcgttgtg    2760
aagaaaacat gctcatctgt gttatttat ggatcagcga cgaaacctcc cccaaatacc    2820 ccttttttt tt                                                         2832
```

<210> SEQ ID NO 4
<211> LENGTH: 22
<212> TYPE: DNA
<213> ORGANISM: Artificial Sequence
<220> FEATURE:
<223> OTHER INFORMATION: Primer

<400> SEQUENCE: 4
cccgctgctt tcgctcattt tg                                             22

<210> SEQ ID NO 5
<211> LENGTH: 22
<212> TYPE: DNA
<213> ORGANISM: Artificial Sequence

```
<220> FEATURE:
<223> OTHER INFORMATION: Primer

<400> SEQUENCE: 5
gactaccgga gctcccacct tc                                            22

<210> SEQ ID NO 6
<211> LENGTH: 22
<212> TYPE: DNA
<213> ORGANISM: Artificial Sequence
<220> FEATURE:
<223> OTHER INFORMATION: Primer

<400> SEQUENCE: 6
agatgtgaat ggctgcttgc tg                                            22

<210> SEQ ID NO 7
<211> LENGTH: 22
<212> TYPE: DNA
<213> ORGANISM: Artificial Sequence
<220> FEATURE:
<223> OTHER INFORMATION: Primer

<400> SEQUENCE: 7
caggtcgacc atatgggaga gc                                            22

<210> SEQ ID NO 8
<211> LENGTH: 18
<212> TYPE: PRT
<213> ORGANISM: Artificial Sequence
<220> FEATURE:
<223> OTHER INFORMATION: Antigenic determinant

<400> SEQUENCE: 8

Thr Ser Leu Asn Leu Gln Lys Asp Glu Pro Asn Gly Arg Ala Ser
1               5                   10                  15

Leu Gly Cys
        18

<210> SEQ ID NO 9
<211> LENGTH: 12
<212> TYPE: PRT
<213> ORGANISM: Artificial Sequence
<220> FEATURE:
<223> OTHER INFORMATION: Antigenic determinant

<400> SEQUENCE: 9

Ala Gly Gly Pro Ser Gly Glu Val Met Ile Gly Cys
1               5                   10      12

<210> SEQ ID NO 10
<211> LENGTH: 27
<212> TYPE: DNA
<213> ORGANISM: Artificial Sequence
<220> FEATURE:
<223> OTHER INFORMATION: Primer

<400> SEQUENCE: 10
gcaaaagcca gatcataaat ttagagc                                       27

<210> SEQ ID NO 11
<211> LENGTH: 27
<212> TYPE: DNA
<213> ORGANISM: Artificial Sequence
```

-continued

```
<220> FEATURE:
<223> OTHER INFORMATION: Primer

<400> SEQUENCE: 11
cttccaattc attgttaatg gtcacac                                            27
```